(12) United States Patent
Parham et al.

(10) Patent No.: US 10,923,665 B2
(45) Date of Patent: Feb. 16, 2021

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Jonas Kroeber, Frankfurt am Main (DE); Dominik Joosten, Frankfurt am Main (DE); Aurélie Ludemann, Frankfurt am Main (DE); Christian Eickhoff, Mannheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/484,845

(22) PCT Filed: Feb. 12, 2018

(86) PCT No.: PCT/EP2018/053380
§ 371 (c)(1),
(2) Date: Aug. 9, 2019

(87) PCT Pub. No.: WO2018/149769
PCT Pub. Date: Aug. 23, 2018

(65) Prior Publication Data
US 2020/0044162 A1 Feb. 6, 2020

(30) Foreign Application Priority Data
Feb. 14, 2017 (EP) .................................... 17155945

(51) Int. Cl.
*C07D 471/04* (2006.01)
*H01L 51/50* (2006.01)
*H01L 51/00* (2006.01)
*C09K 11/02* (2006.01)

(52) U.S. Cl.
CPC ........ *H01L 51/0072* (2013.01); *C07D 471/04* (2013.01); *C09K 11/025* (2013.01); *H01L 51/0067* (2013.01); *H01L 51/0073* (2013.01); *H01L 51/5012* (2013.01); *H01L 51/5056* (2013.01); *H01L 51/5072* (2013.01); *H01L 51/5096* (2013.01)

(58) Field of Classification Search
CPC .. C07D 401/04; C07D 471/04; H01L 51/5012
USPC ............................................. 546/70; 313/504
See application file for complete search history.

(56) References Cited

U.S. PATENT DOCUMENTS 9,515,266 B2 12/2016 Jatsch et al.
9,818,948 B2 11/2017 Jatsch et al.

FOREIGN PATENT DOCUMENTS

WO WO-2013041176 A1 3/2013
WO WO-2013056776 A1 4/2013

OTHER PUBLICATIONS

Database CAPLUS, Cookson, R., et al., "Cyanoethylation of amines and arsines", Journal of the Chemical Society, (1949), pp. 67-72, XP002778927, Accession No. 1949: 46387.
International Search Report for PCT/EP2018/053380 dated Apr. 3, 2018.
Written Opinion of the International Searching Authority for PCT/EP2018/053380 dated Apr. 3, 2018.
Yan, Z., et al., "An efficient iron-promoted synthesis of 6H-indolo[2,3-b]quinolines and neocryptolepine derivatives", Organic and Biomolecular Chemistry, vol. 14, No. 19, (2016), pp. 4405-4408.
Shi, Z., et al., "CuI-catalyzed photochemical or thermal reactions of 3-(2-azidobenzylidene)-lactams. Application to the synthesis of fused indoles", Chem. Comm., 2010, 46, pp. 3973-3975.
"5-(1 H-Benzimidazol-2-yl)-5H-indolo[2,3-b]quinoxaline", Pubchem, PubChem CID 121232633, Dated Aug. 2, 2016.
"5-(3,5-Dibromophenyl)indolo[2,3-b]quinoline", Pubchem, Pubchem CID 123947488, dated Jan. 25, 2017.

*Primary Examiner* — Charanjit Aulakh
(74) *Attorney, Agent, or Firm* — Faegre Drinker Biddle & Reath LLP

(57) ABSTRACT

The present invention relates to compounds suitable for use in electronic devices, and to electronic devices, especially organic electroluminescent devices, comprising these compounds.

14 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/053380, filed Feb. 12, 2018, which claims benefit of European Application No. 17155945.3, filed Feb. 14, 2017, both of which are incorporated herein by reference in their entirety.

The present invention relates to materials for use in electronic devices, especially in organic electroluminescent devices, and to electronic devices, especially organic electroluminescent devices comprising these materials.

Emitting materials used in organic electroluminescent devices (OLEDs) are frequently organometallic complexes which exhibit phosphorescence rather than fluorescence. For quantum-mechanical reasons, up to four times the energy efficiency and power efficiency is possible using organometallic compounds as phosphorescent emitters. In general terms, however, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials can thus also lead to improvements in the OLED properties.

The problem addressed by the present invention is that of providing compounds suitable for use in an OLED, especially as matrix material for phosphorescent emitters, especially for red-phosphorescing emitters, but also as electron transport materials, hole blocker materials or exciton blocker materials. A further problem addressed by the present invention is that of providing further organic semiconductors for organic electroluminescent devices, in order thus to enable the person skilled in the art to have a greater possible choice of materials for the production of OLEDs.

It has been found that, surprisingly, particular compounds described in detail hereinafter solve this problem and are of good suitability for use in OLEDs. These OLEDs especially have a good lifetime, high efficiency and low operating voltage. The present invention therefore provides these compounds and electronic devices, especially organic electroluminescent devices, comprising such compounds.

The present invention provides a compound of formula (1)

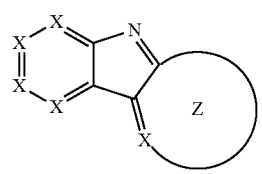

Formula (1)

where the symbols used are as follows:
Z is a group of the following formula (2):

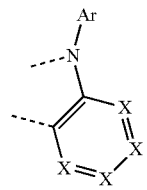

Formula (2)

where the dotted bonds indicate the linkage of this group to X and the carbon atom in formula (1);
X is the same or different at each instance and is CR or N;
Ar is an aromatic or heteroaromatic ring system which has 5 to 40 aromatic ring atoms and may be substituted by one or more R radicals;
R is the same or different at each instance and is H, D, F, Cl, Br, I, $N(Ar')_2$, $N(R^1)_2$, CN, $NO_2$, $OR^1$, SRS, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, $C=O$, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form a ring system;
Ar' is the same or different at each instance and is an aromatic or heteroaromatic ring system which has 5 to 40 aromatic ring atoms and may be substituted by one or more $R^1$ radicals;
$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $Si(R^2)_2$, $C=O$, $NR^2$, O, S or $CONR^2$, or an aromatic or heteroaromatic ring system which has 5 to 40 aromatic ring atoms and may be substituted in each case by one or more $R^2$ radicals; at the same time, two or more $R^1$ radicals together may form a ring system;
$R^2$ is the same or different at each instance and is H, D, F or an aliphatic, aromatic or heteroaromatic organic radical, especially a hydrocarbyl radical, having 1 to 20 carbon atoms, in which one or more hydrogen atoms may also be replaced by F;
where the following compounds are excluded from the invention:

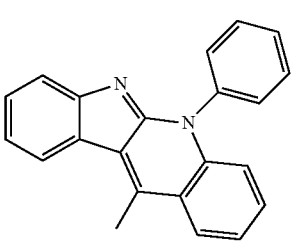

-continued

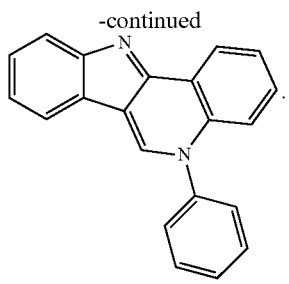

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms, preferably 6 to 40 carbon atoms, in the ring system. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferred aromatic or heteroaromatic ring systems are simple aryl or heteroaryl groups and groups in which two or more aryl or heteroaryl groups are joined directly to one another, and also fluorene or spirobifluorene.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethyl hexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, quinazoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

When two R or $R^1$ radicals together form a ring system, it may be mono- or polycyclic, and aliphatic, heteroaliphatic, aromatic or heteroaromatic. In this case, the radicals which together form a ring system are preferably adjacent, meaning that these radicals are bonded to the same carbon atom or to carbon atoms directly bonded to one another.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

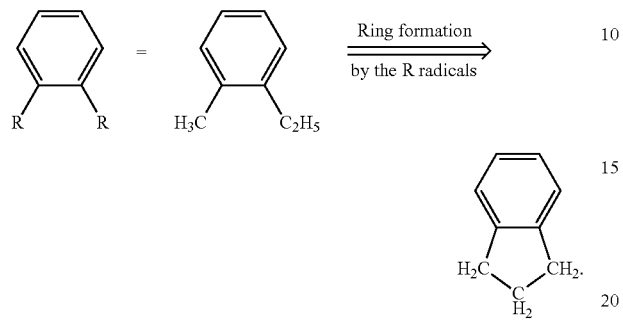

In addition, however, the abovementioned wording shall also be understood to mean that, if one of the two radicals is hydrogen, the second radical binds to the position to which the hydrogen atom was bonded, forming a ring. This shall be illustrated by the following scheme.

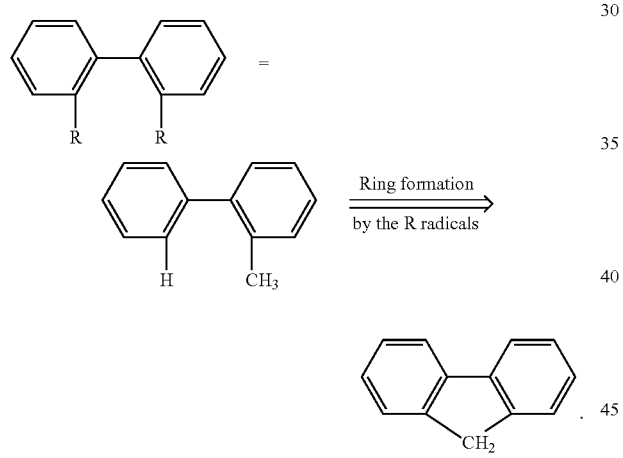

The formation of an aromatic ring system shall be illustrated by the following scheme:

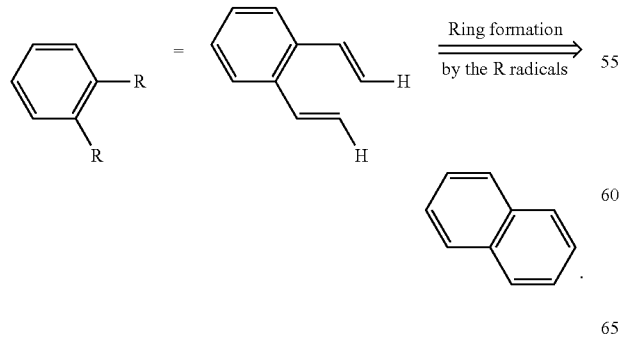

Two different isomers arise according to the alignment of the Z group.

These are represented hereinafter by the formulae (3) and (4)

Formula (3)

Formula (4)

where the symbols used have the definitions given above.

In a further preferred embodiment of the invention, in the formulae (1), (3) and (4), not more than one symbol X per cycle is N and the other symbols X are CR. In a particularly preferred embodiment of the invention, all symbols X in formulae (1), (3) and (4) are CR, or one symbol X is N and the remaining symbols X are CR.

Preferred embodiments of the formula (3) are the compounds of the following formulae (3a) to (3c), and preferred embodiments of the formula (4) are the compounds of the following formulae (4a) to (4d):

Formula (3a)

Formula (3b)

Formula (3c)

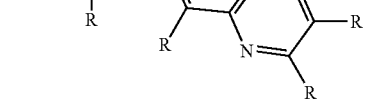

Formula (4a)

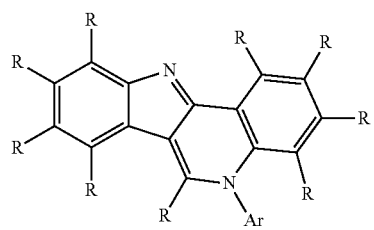

Formula (4b)

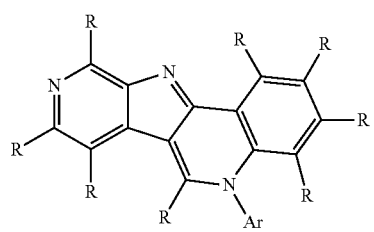

Formula (4c)

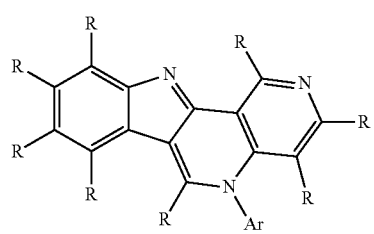

Formula (4d)

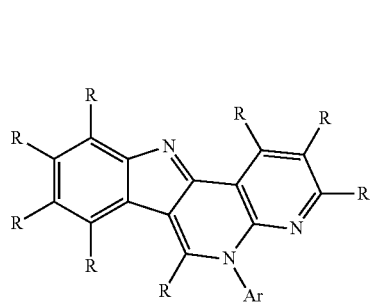

where the symbols used have the definitions given above.

Particular preference is given to the compounds of the formulae (3a) and (4a).

In a preferred embodiment of the invention, not more than three R radicals in total, more preferably not more than two R radicals, most preferably not more than one R radical, in the compound of the formula (1) or in the preferred structures detailed above are/is a group other than hydrogen.

In a particularly preferred embodiment of the invention, the compound of the formula (1) is selected from the compounds of the following formulae (3a-1) to (3a-12) and (4a-1) to (4a-4):

Formula (3a-1)

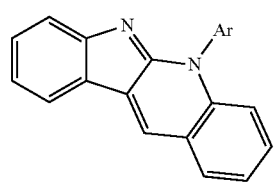

Formula (3a-2)

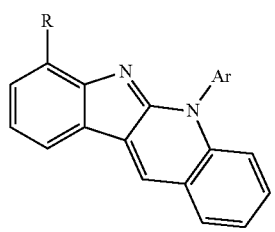

Formula (3a-3)

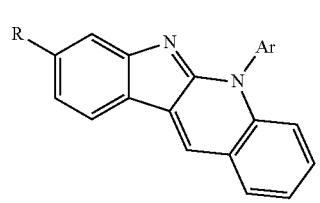

Formula (3a-4)

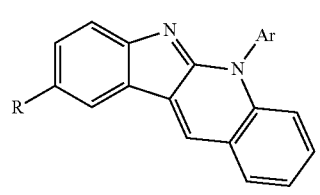

Formula (3a-5)

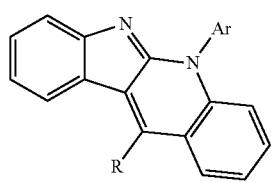

Formula (3a-6)

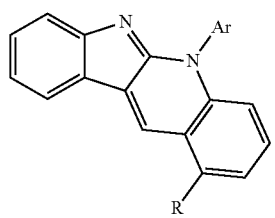

Formula (3a-7)

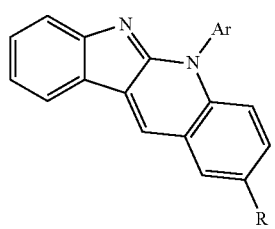

Formula (3a-8)

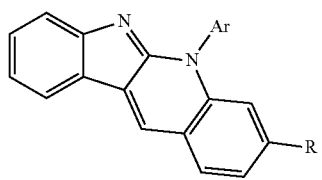

Formula (3a-9)
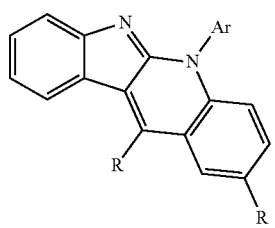

Formula (3a-10)
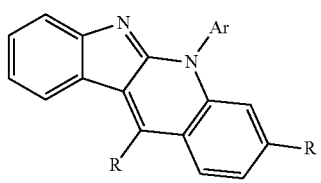

Formula (3a-11)
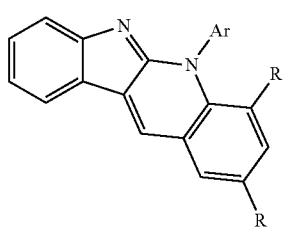

Formula (3a-12)
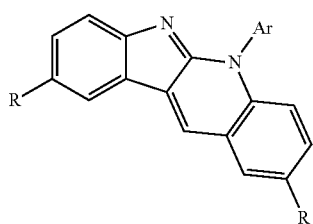

Formula (4a-1)
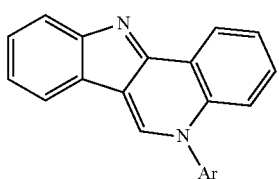

Formula (4a-2)
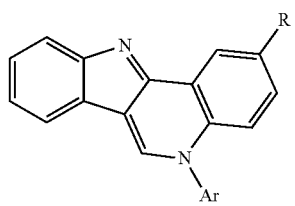

Formuka (4a-3)
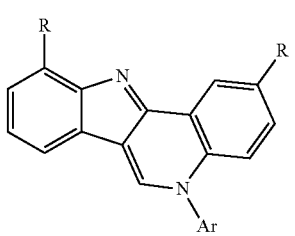

Formula (4a-4)
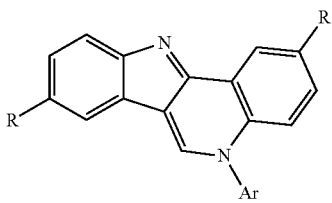

where the symbols used have the definitions given above and R is not hydrogen or deuterium.

In structures of the formulae (3b), (3c), (4b), (4c) and (4d), substituents R other than hydrogen are preferably bonded in the same positions as shown for the formulae (3a-1) to (3a-12) and (4a-1) to (4a-4).

There follows a description of preferred substituents Ar, R, Ar', $R^1$ and $R^2$ in the compounds of the invention. In a particularly preferred embodiment of the invention, the preferences specified hereinafter for Ar, R, Ar', $R^1$ and $R^2$ occur simultaneously and are applicable to all structures of the formulae (1), (3), (4) and the above-detailed preferred embodiments of these formulae.

In a preferred embodiment of the invention, Ar is an aromatic or heteroaromatic ring system which has 6 to 30 aromatic ring atoms and may be substituted by one or more R radicals. More preferably, Ar is an aromatic or heteroaromatic ring system which has 6 to 24 aromatic ring atoms, especially 6 to 13 aromatic ring atoms, and may be substituted by one or more preferably nonaromatic R radicals. When Ar is a heteroaryl group, especially triazine, pyrimidine or quinazoline, preference may also be given to aromatic or heteroaromatic substituents R on this heteroaryl group. It may further be preferable when Ar is substituted by an $N(Ar')_2$ group, such that the Ar substituent on the nitrogen atom in formula (1) or the preferred embodiments constitutes a triarylamine or triheteroarylamine group overall.

Suitable aromatic or heteroaromatic ring systems Ar are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals, preferably nonaromatic R radicals. When Ar is a heteroaryl group, especially triazine, pyrimidine or quinazoline, preference may also be given to aromatic or heteroaromatic R radicals on this heteroaryl group.

Ar here is preferably selected from the groups of the following formulae Ar-1 to Ar-76:

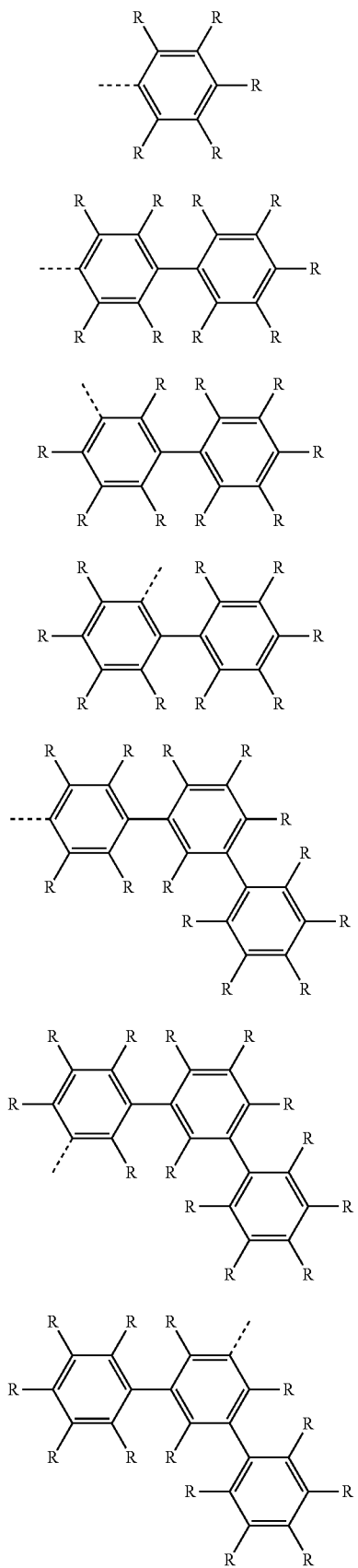
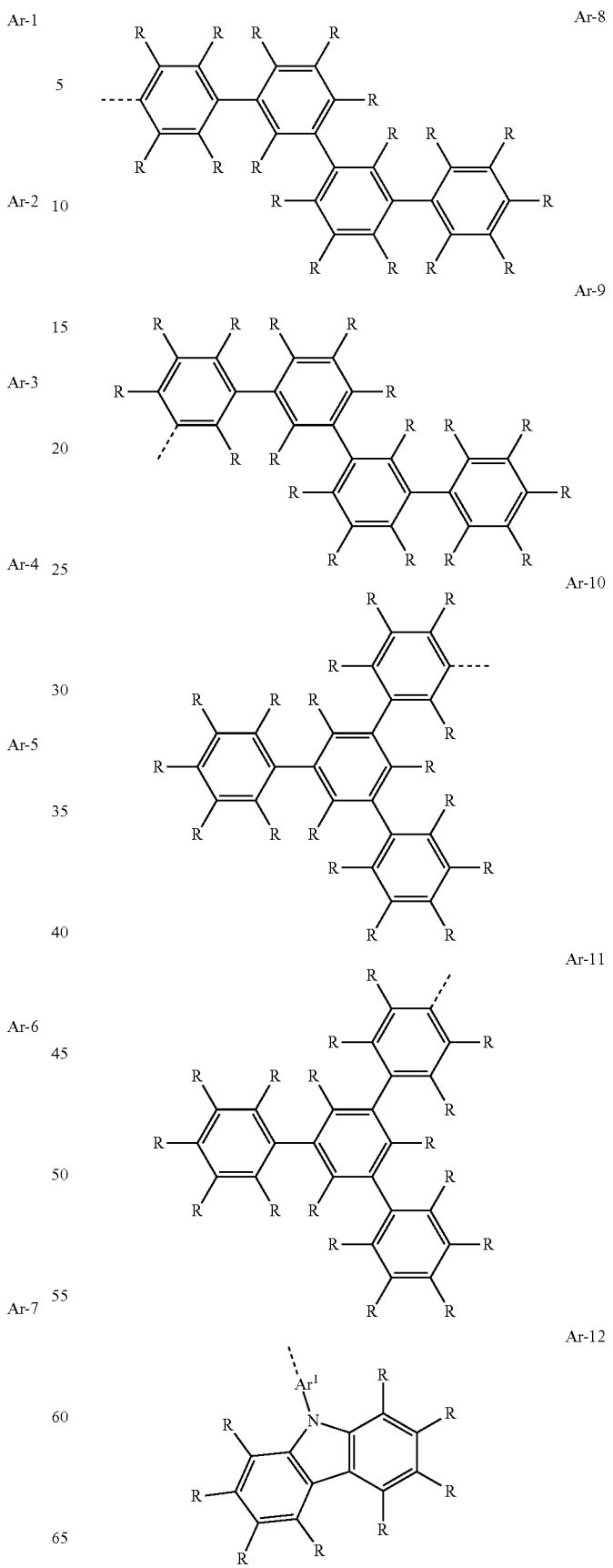

Ar-13
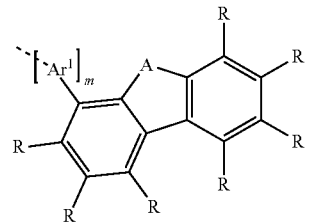
Ar-14
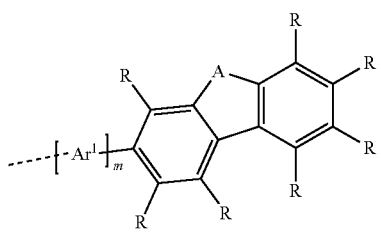
Ar-15
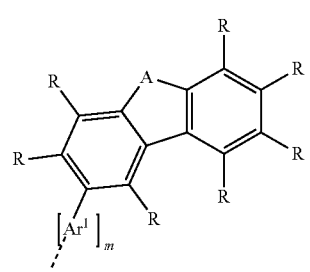
Ar-16
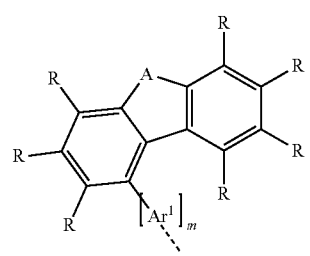
Ar-17
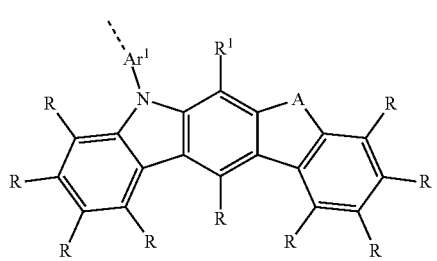
Ar-18
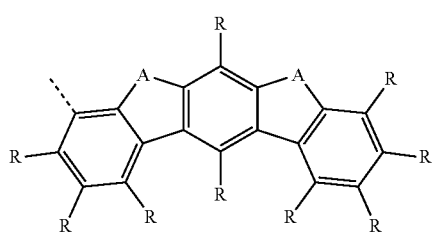
Ar-19
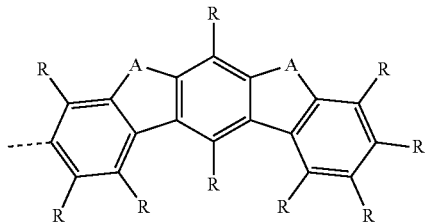
Ar-20
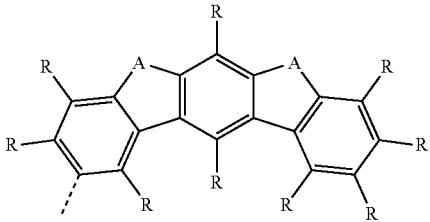
Ar-21
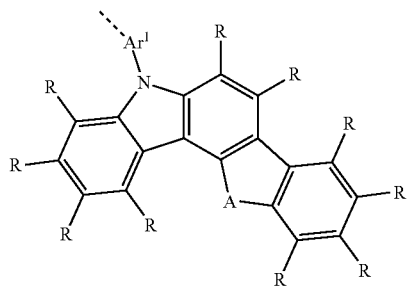
Ar-22
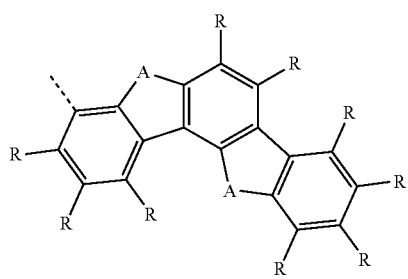
Ar-23
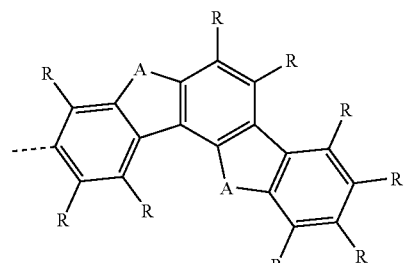
Ar-24
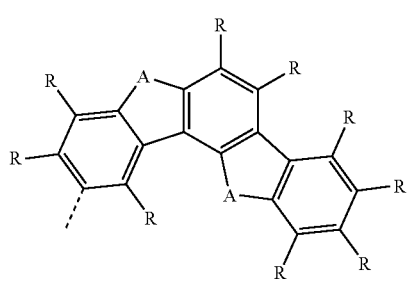

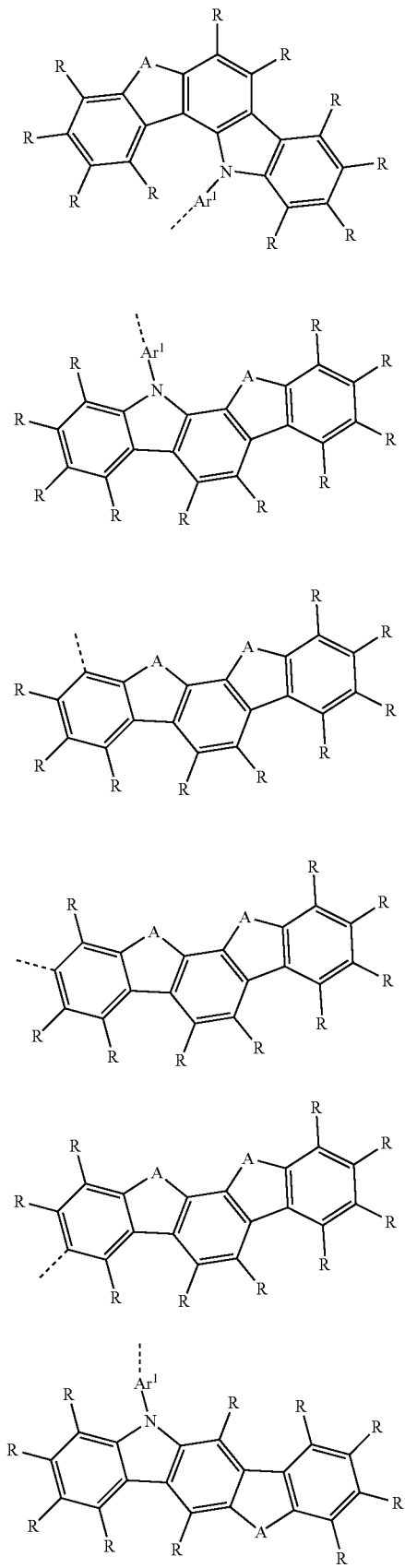
Ar-25
Ar-26
Ar-27
Ar-28
Ar-29
Ar-30
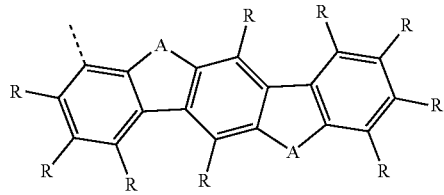
Ar-31
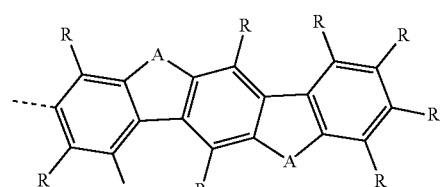
Ar-32
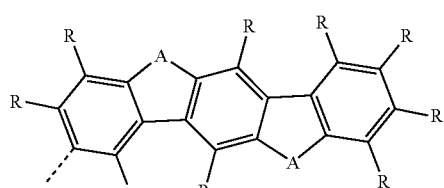
Ar-33
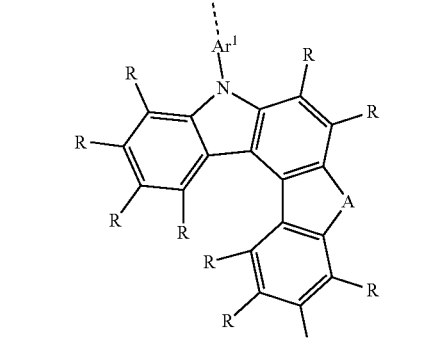
Ar-34
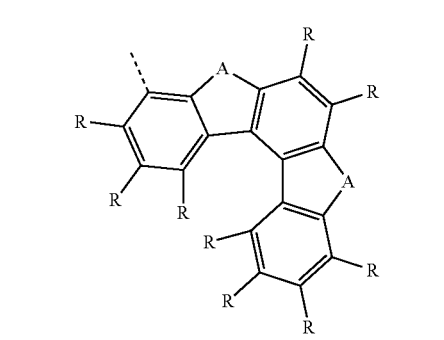
Ar-35
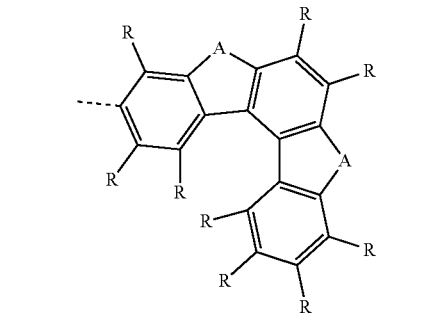
Ar-36

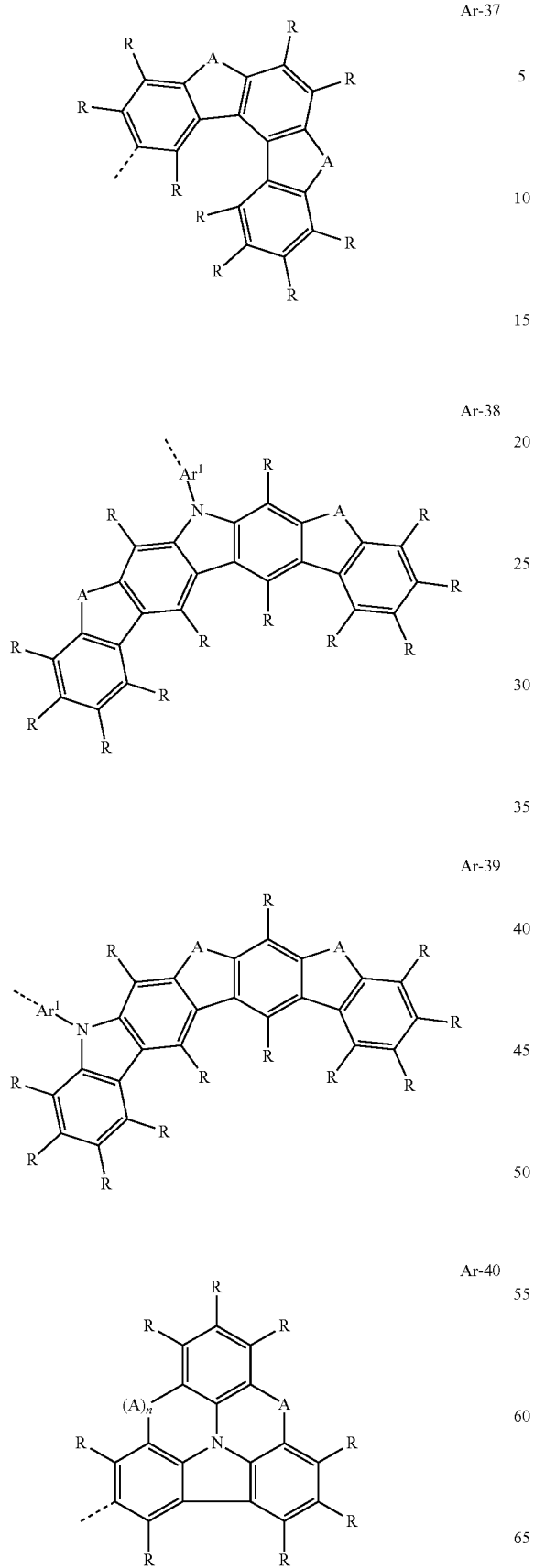
Ar-37
Ar-38
Ar-39
Ar-40
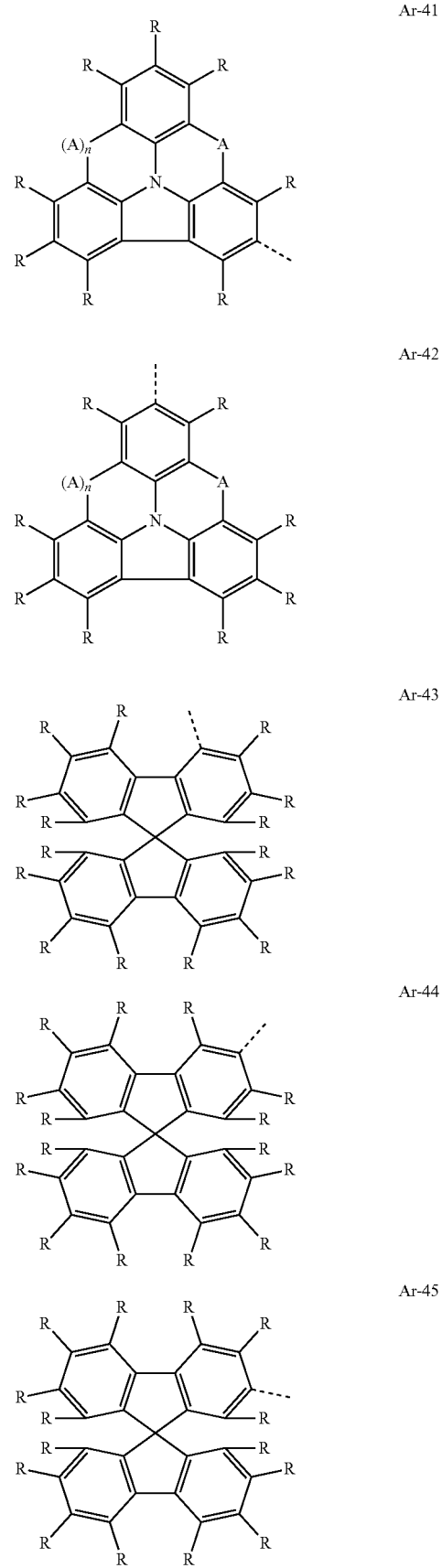
Ar-41
Ar-42
Ar-43
Ar-44
Ar-45

-continued
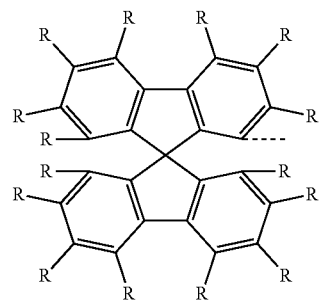
Ar-46
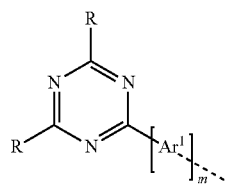
Ar-47
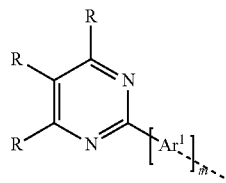
Ar-48
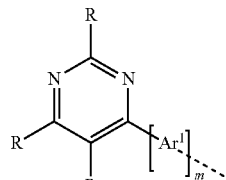
Ar-49
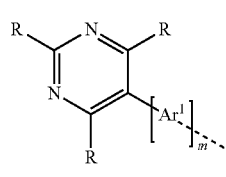
Ar-50
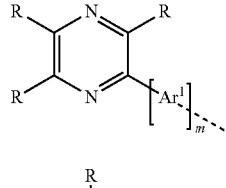
Ar-51
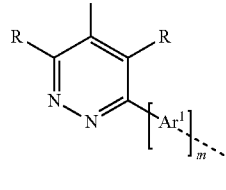
Ar-52
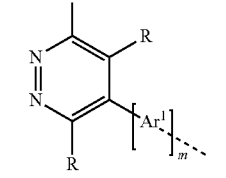
Ar-53
-continued
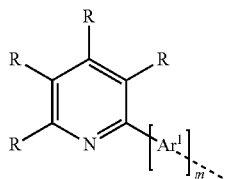
Ar-54
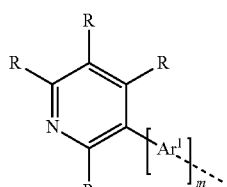
Ar-55
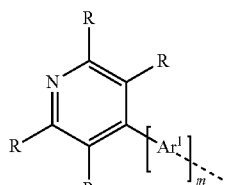
Ar-56
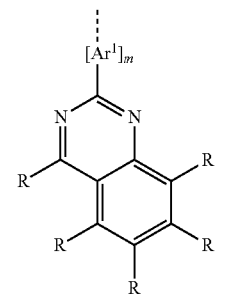
Ar-57
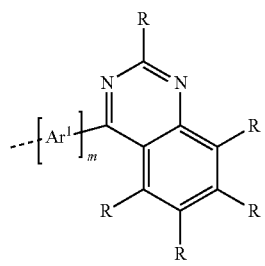
Ar-58
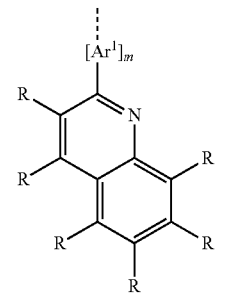
Ar-59

Ar-60 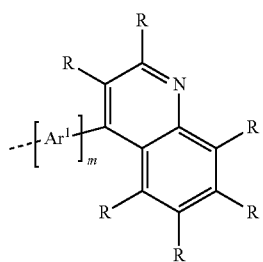
Ar-61 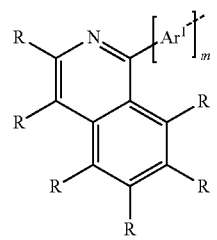
Ar-62 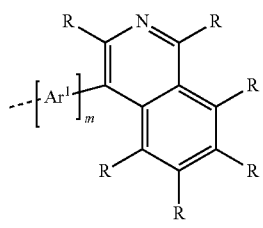
Ar-63 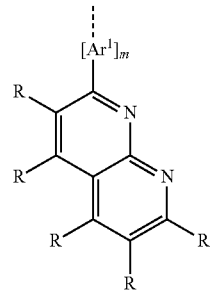
Ar-64 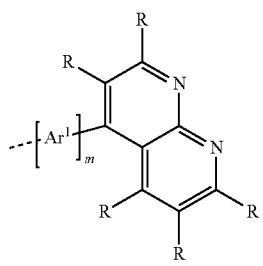
Ar-65 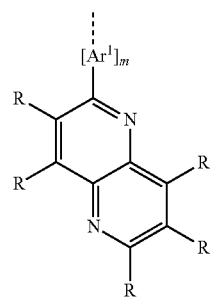
Ar-66 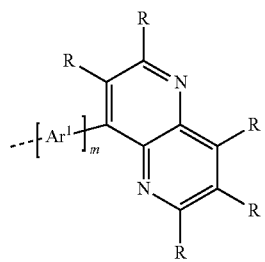
Ar-67 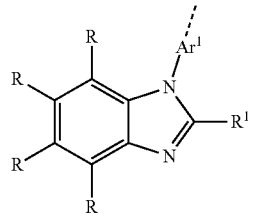
Ar-68 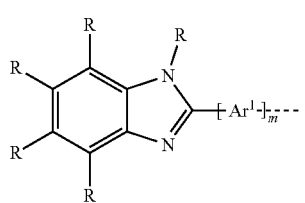
Ar-69 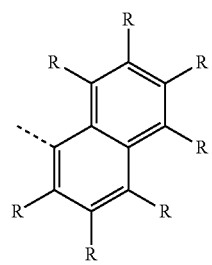
Ar-70 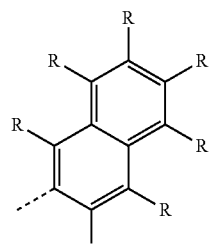
Ar-71 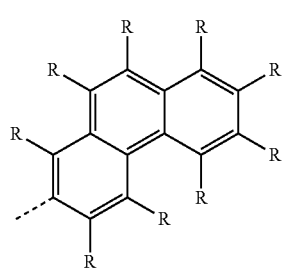

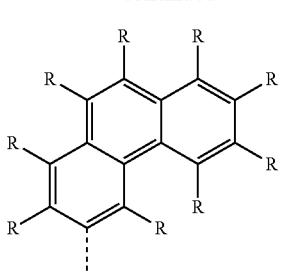
Ar-72

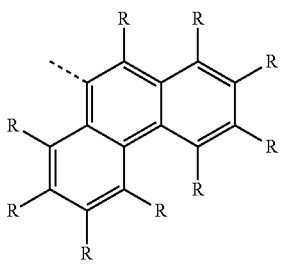
Ar-73

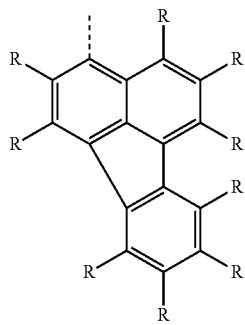
Ar-74

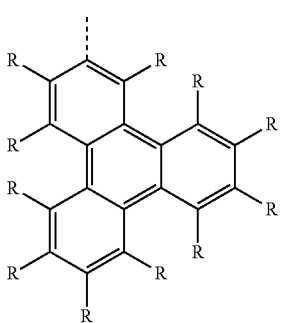
Ar-75

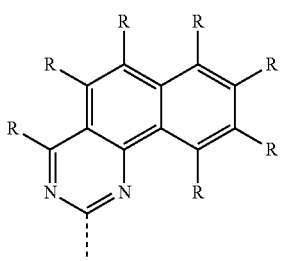
Ar-76 where R is as defined above, the dotted bond represents the bond to the nitrogen atom and, in addition:

Ar$^1$ is the same or different at each instance and is a divalent aromatic or heteroaromatic ring system which has 6 to 18 aromatic ring atoms, preferably 6 to 13 aromatic ring atoms, and may be substituted in each case by one or more R radicals;

A is the same or different at each instance and is C(R)$_2$, NR, O or S;

n is 0 or 1, where n=0 means that no A group is bonded at this position and R radicals are bonded to the corresponding carbon atoms instead;

m is 0 or 1, where m=0 means that the Ar$^1$ group is absent and that the corresponding aromatic or heteroaromatic group is bonded directly to the nitrogen atom.

In a preferred embodiment of the invention, R is the same or different at each instance and is selected from the group consisting of H, D, F, N(Ar')$_2$, CN, OR$^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R$^1$ radicals, but is preferably unsubstituted, and where one or more nonadjacent CH$_2$ groups may be replaced by O, or an aromatic or heteroaromatic ring system which has 6 to 30 aromatic ring atoms and may be substituted in each case by one or more R$^1$ radicals; at the same time, two R radicals together may also form a ring system, preferably an aliphatic ring system. More preferably, R is the same or different at each instance and is selected from the group consisting of H, N(Ar')$_2$, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more R$^1$ radicals, but is preferably unsubstituted, or an aromatic or heteroaromatic ring system which has 6 to 24 aromatic ring atoms and may be substituted in each case by one or more R$^1$ radicals, preferably nonaromatic R$^1$ radicals. Most preferably, R is the same or different at each instance and is selected from the group consisting of H or an aromatic or heteroaromatic ring system which has 6 to 24 aromatic ring atoms and may be substituted in each case by one or more R$^1$ radicals, preferably nonaromatic R$^1$ radicals. It may additionally be preferable that R is a triaryl- or -heteroarylamine group which may be substituted by one or more R$^1$ radicals. This group is one embodiment of an aromatic or heteroaromatic ring system, in which case two or more aryl or heteroaryl groups are joined to one another by a nitrogen atom. When R is a triaryl- or -heteroarylamine group, this group preferably has 18 to 30 aromatic ring atoms and may be substituted by one or more R$^1$ radicals, preferably nonaromatic R$^1$ radicals.

In a further preferred embodiment of the invention, Ar' is an aromatic or heteroaromatic ring system which has 6 to 30 aromatic ring atoms and may be substituted by one or more R$^1$ radicals. In a particularly preferred embodiment of the invention, Ar' is an aromatic or heteroaromatic ring system which has 6 to 24 aromatic ring atoms, especially 6 to 13 aromatic ring atoms, and may be substituted by one or more preferably nonaromatic R$^1$ radicals.

In a further preferred embodiment of the invention, R$^1$ is the same or different at each instance and is selected from the group consisting of H, D, F, CN, OR$^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R$^2$ radicals, and where one or more nonadjacent CH$_2$ groups may be replaced by O, or an aromatic or heteroaromatic ring system which has 6 to 30 aromatic ring atoms and may be substituted in each case by one or more R$^2$ radicals; at the same time, two or more R$^1$ radicals together may form an aliphatic ring system. In a particularly preferred embodiment of the invention, R$^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

Suitable aromatic or heteroaromatic ring systems R or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more $R^1$ radicals. When R or Ar' is a heteroaryl group, especially triazine, pyrimidine or quinazoline, preference may also be given to aromatic or heteroaromatic $R^1$ radicals on this heteroaryl group.

The R or Ar' groups here are preferably selected from the groups of the following formulae R-1 to R-76:

R-1
R-2
R-3

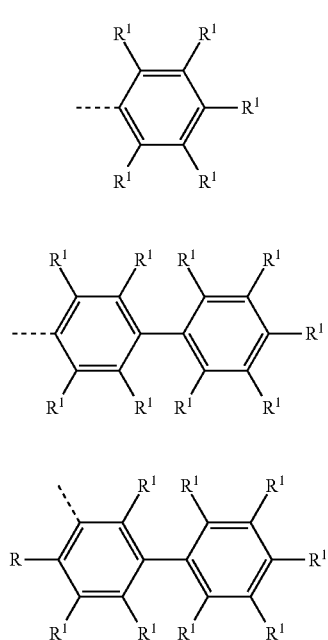

R-4
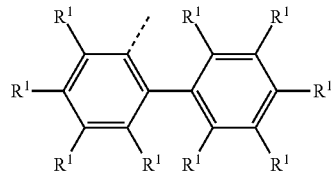

R-5
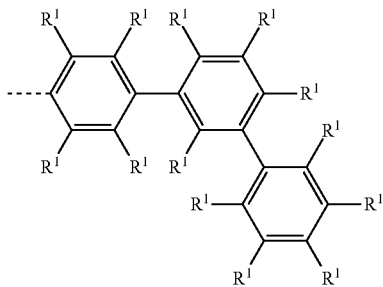

R-6
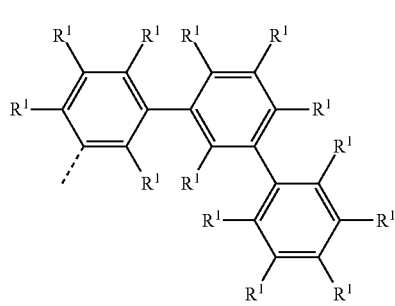

R-7
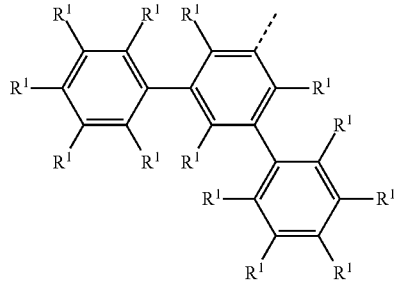

R-8
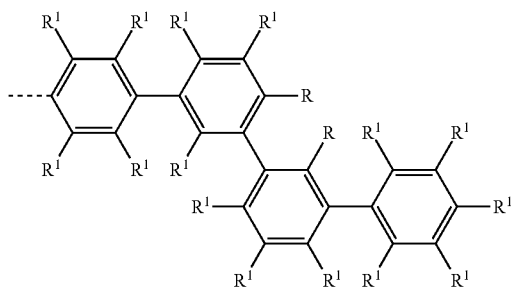

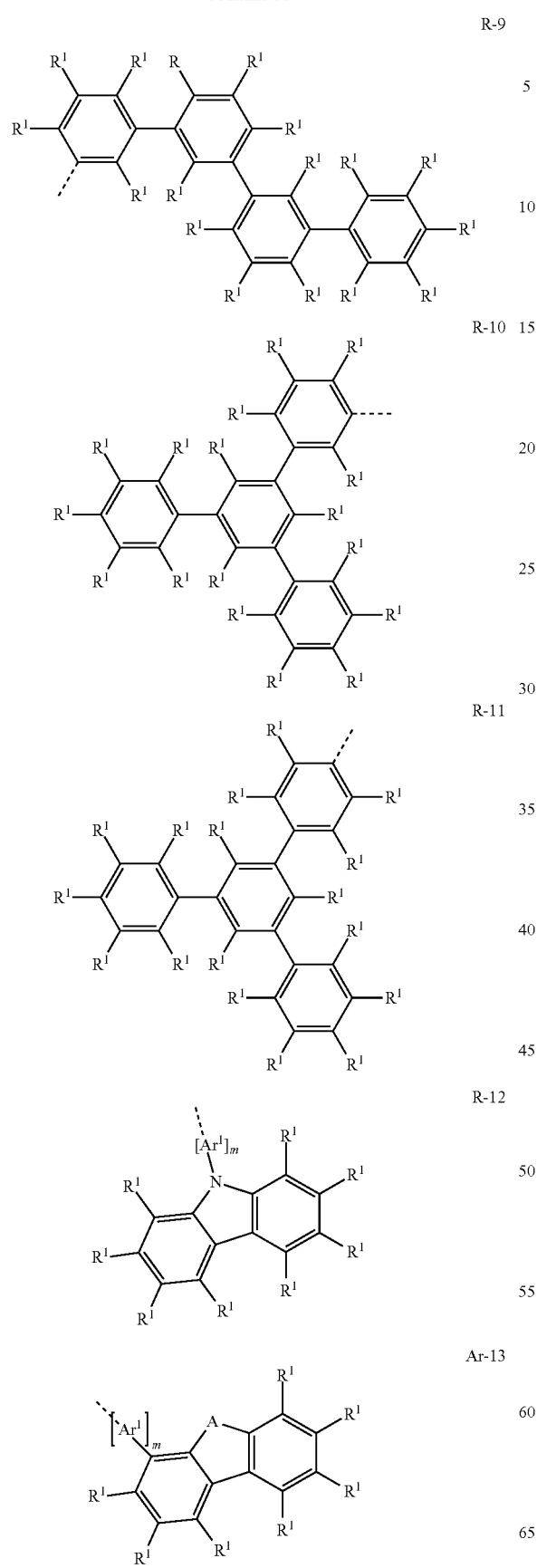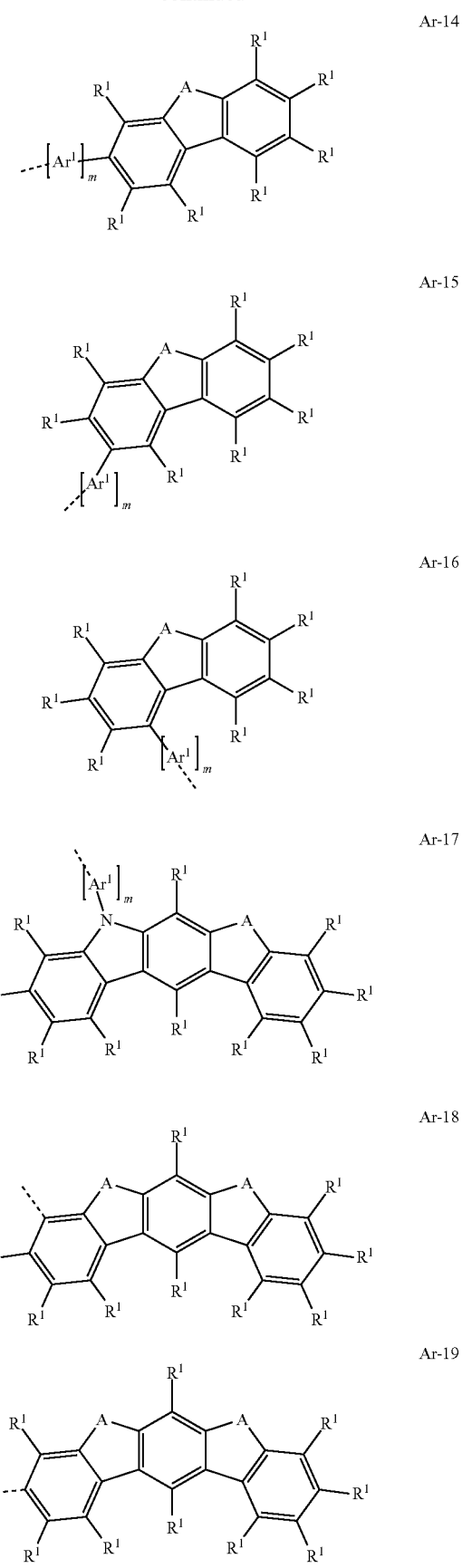

Ar-20 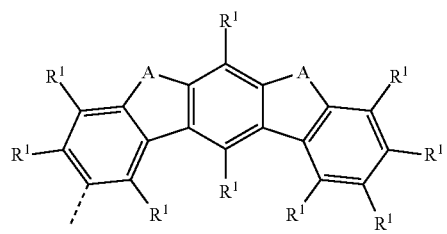
Ar-21 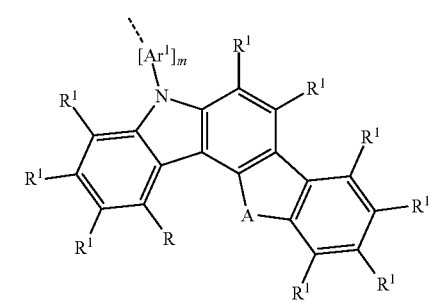
Ar-22 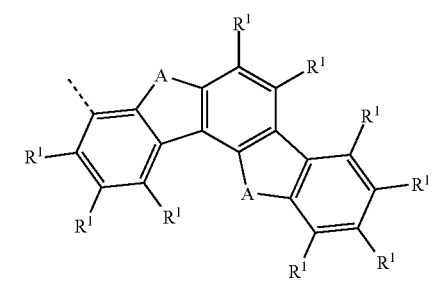
Ar-23 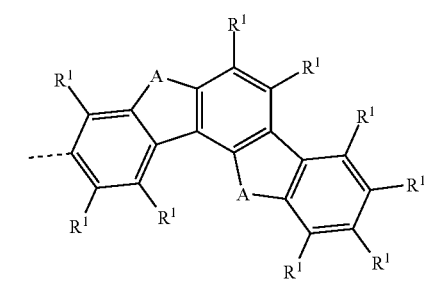
Ar-24 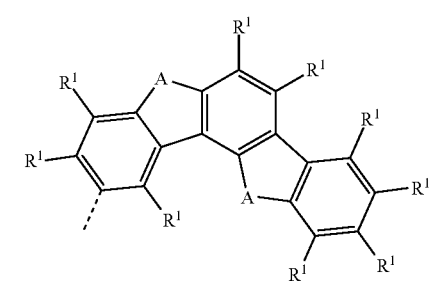
Ar-25 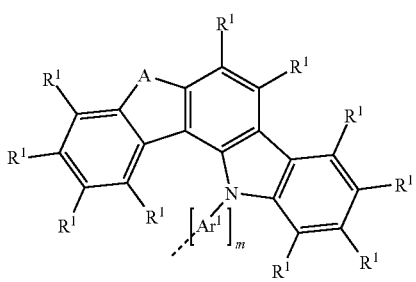
Ar-26 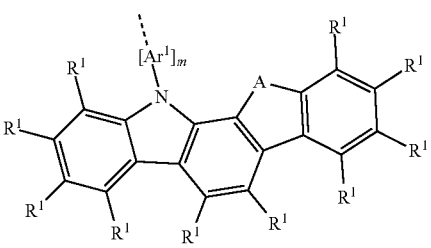
Ar-27 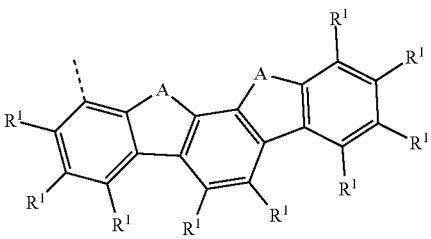
Ar-28 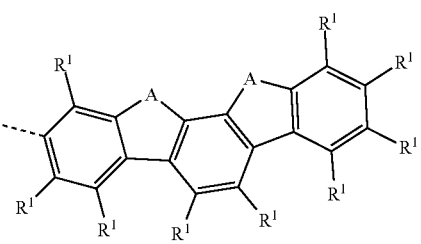
Ar-29 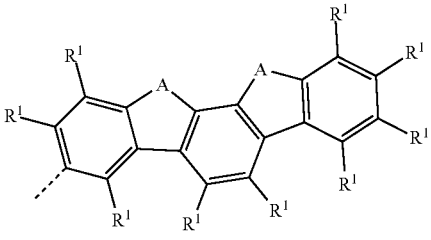
Ar-30 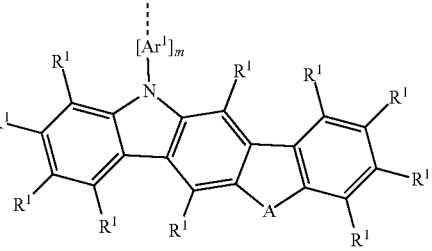

Ar-31
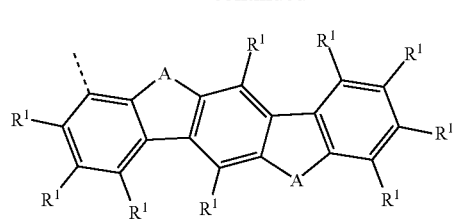
Ar-32
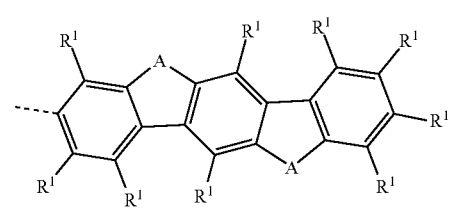
Ar-33
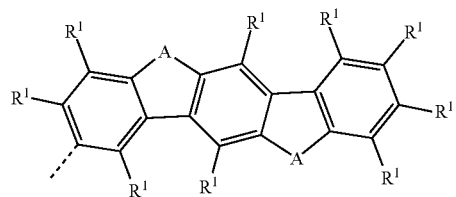
Ar-34
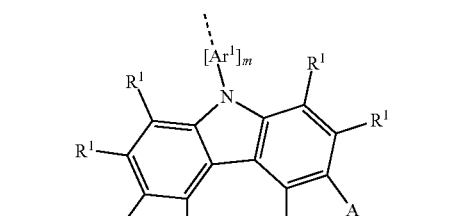
Ar-35
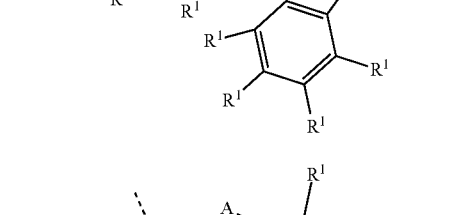
Ar-36
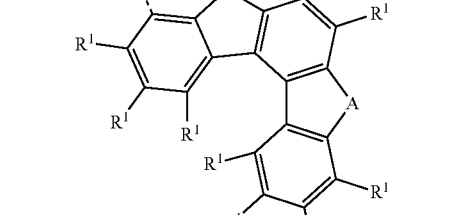
Ar-37
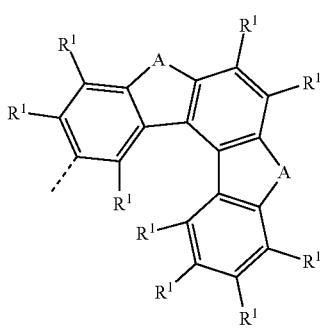
Ar-38
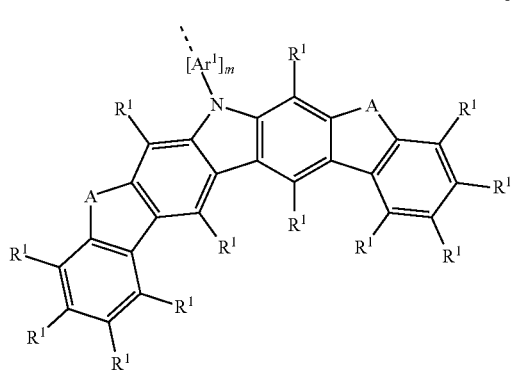
Ar-39
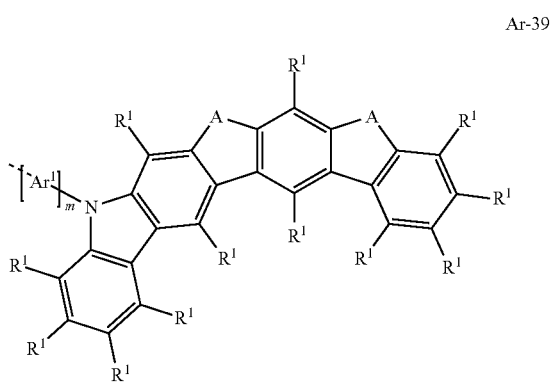
Ar-40
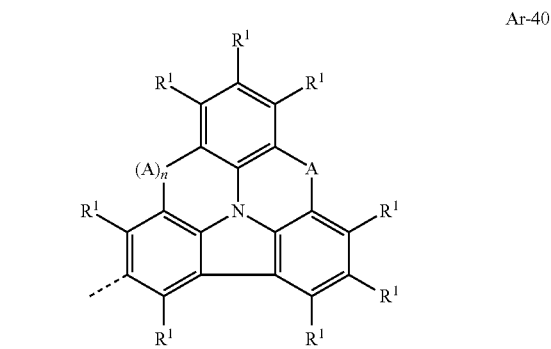

-continued
Ar-41
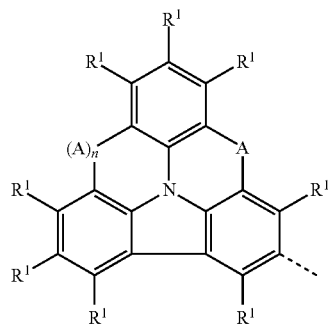
Ar-42
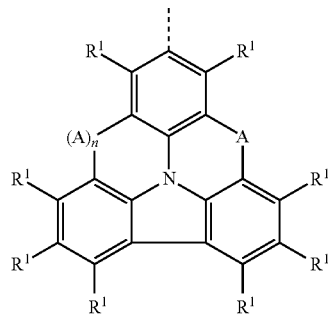
Ar-43
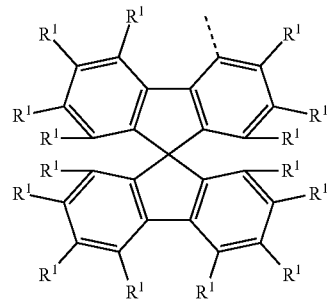
Ar-44
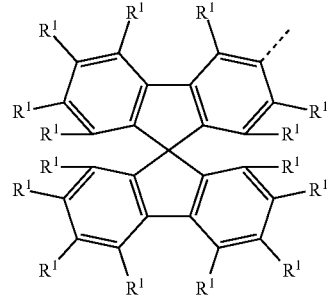
Ar-45
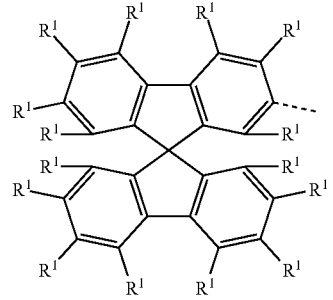
-continued
Ar-46
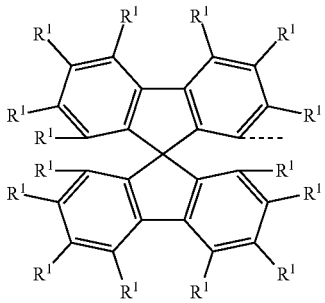
Ar-47
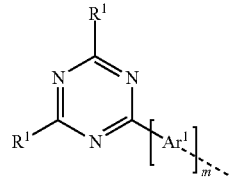
Ar-48
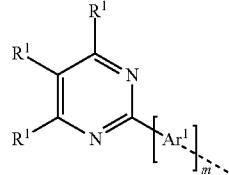
Ar-49
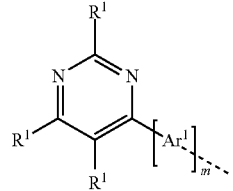
Ar-50
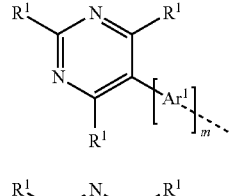
Ar-51
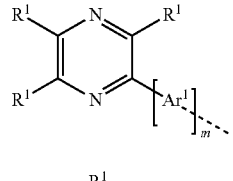
Ar-52
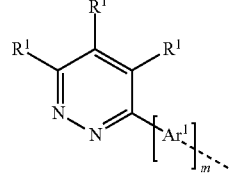
Ar-53
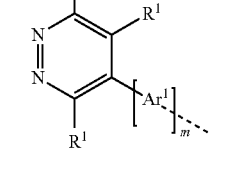

Ar-54
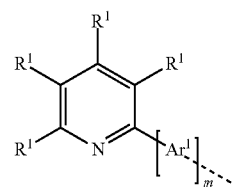
Ar-55
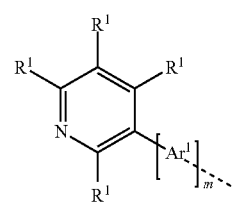
Ar-56
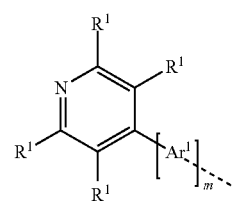
Ar-57
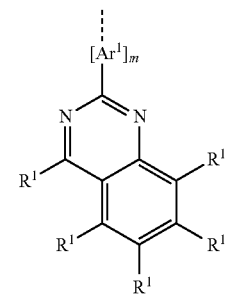
Ar-58
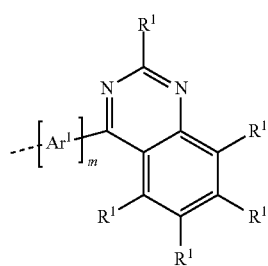
Ar-59
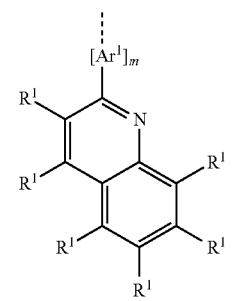
Ar-60
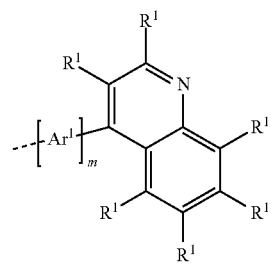
Ar-61
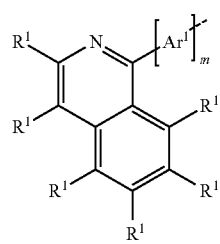
Ar-62
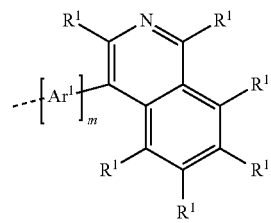
Ar-63
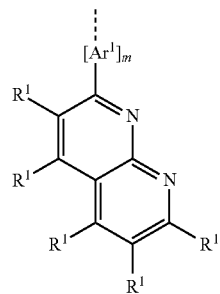
Ar-64
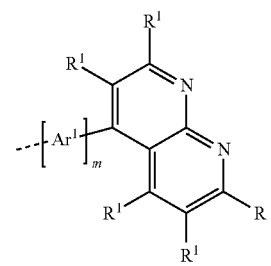
Ar-65
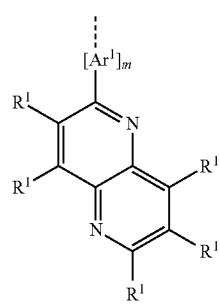

Ar-66 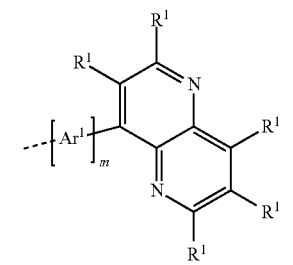

Ar-67 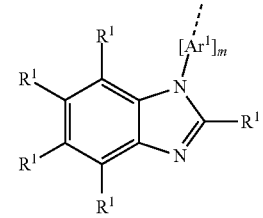

Ar-68 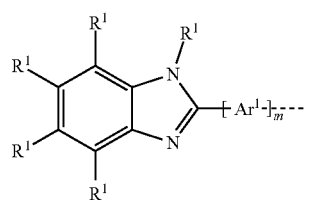

Ar-69 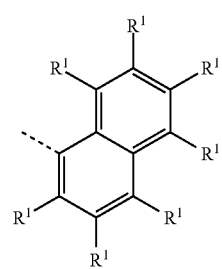

Ar-70 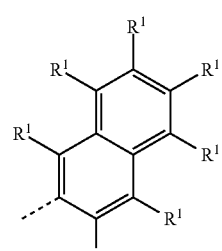

Ar-71 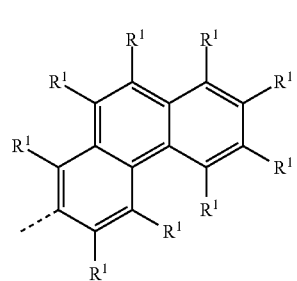

Ar-72 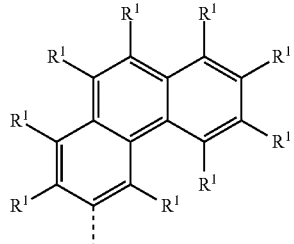

Ar-73 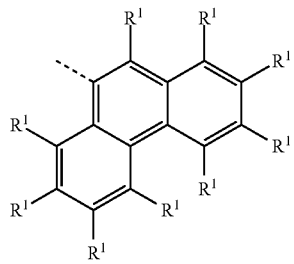

Ar-74 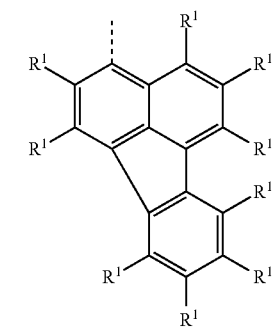

Ar-75 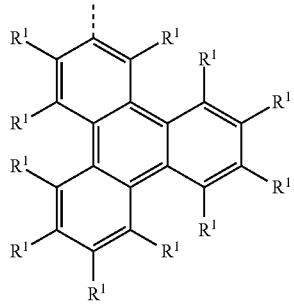

Ar-76 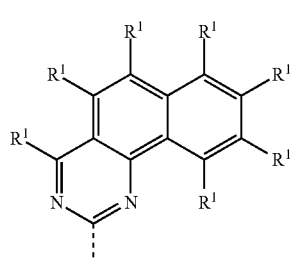

where $R^1$ has the definitions given above, the dotted bond represents the bond to a carbon atom of the base skeleton in formula (1) or in the preferred embodiments or to the nitrogen atom in the $N(Ar')_2$ group and, in addition:

$Ar^1$ is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

n is 0 or 1, where n=0 means that no A group is bonded at this position and $R^1$ radicals are bonded to the corresponding carbon atoms instead;

m is 0 or 1, where m=0 means that the $Ar^1$ group is absent and that the corresponding aromatic or heteroaromatic group is bonded directly to a carbon atom of the base skeleton in formula (1) or in the preferred embodiments, or to the nitrogen atom in the $N(Ar')_2$ group; with the proviso that m=1 for the structures (R-12), (R-17), (R-21), (R-25), (R-26), (R-30), (R-34), (R-38) and (R-39) when these groups are embodiments of Ar'.

When the abovementioned Ar-1 to Ar-76 groups for Ar or R-1 to R-76 groups for R or Ar' have two or more A groups, possible options for these include all combinations from the definition of A. Preferred embodiments in that case are those in which one A group is NR or $NR^1$ and the other A group is $C(R)_2$ or $C(R^1)_2$ or in which both A groups are NR or $NR^1$ or in which both A groups are O. In a particularly preferred embodiment of the invention, in Ar, R or Ar' groups having two or more A groups, at least one A group is $C(R)_2$ or $C(R^1)_2$ or is NR or $NR^1$.

When A is NR or $NR^1$, the substituent R or $R^1$ bonded to the nitrogen atom is preferably an aromatic or heteroaromatic ring system which has 5 to 24 aromatic ring atoms and may also be substituted by one or more $R^1$ or $R^2$ radicals. In a particularly preferred embodiment, this R or $R^1$ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more $R^1$ or $R^2$ radicals. Particular preference is given to phenyl, biphenyl, terphenyl and quaterphenyl having bonding patterns as listed above for Ar-1 to Ar-11 or R-1 to R-11, where these structures may be substituted by one or more $R^1$ or $R^2$ radicals, but are preferably unsubstituted.

When A is $C(R)_2$ or $C(R^1)_2$, the substituents R or $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system which has 5 to 24 aromatic ring atoms and may also be substituted by one or more $R^1$ or $R^2$ radicals. Most preferably, R or $R^1$ is a methyl group or a phenyl group. In this case, the R or $R^1$ radicals together may also form a ring system, which leads to a Spiro system.

Further suitable Ar, R or Ar' groups are groups of the formula —$Ar^4$—$N(Ar^2)(Ar^3)$ where Are, Ara and $Ar^4$ are the same or different at each instance and are an aromatic or heteroaromatic ring system which has 5 to 24 aromatic ring atoms and may be substituted in each case by one or more $R^1$ radicals. Ar results in such a group when the Ar group is substituted by an $N(Ar')_2$ group. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another via a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, especially 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more $R^1$ radicals. More preferably, $Ar^2$ and $Ar^3$ are the same or different at each instance and are an aromatic ring system which has 6 to 24 aromatic ring atoms and may be substituted by one or more $R^1$ radicals, especially selected from the groups consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

At the same time, the alkyl groups in compounds of the invention which are processed by vacuum evaporation preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the Ar, R, Ar', $R^1$ and $R^2$ radicals do not contain any fused aryl or heteroaryl groups in which two or more six-membered rings are fused directly to one another. An exception to this is formed by phenanthrene and triphenylene which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

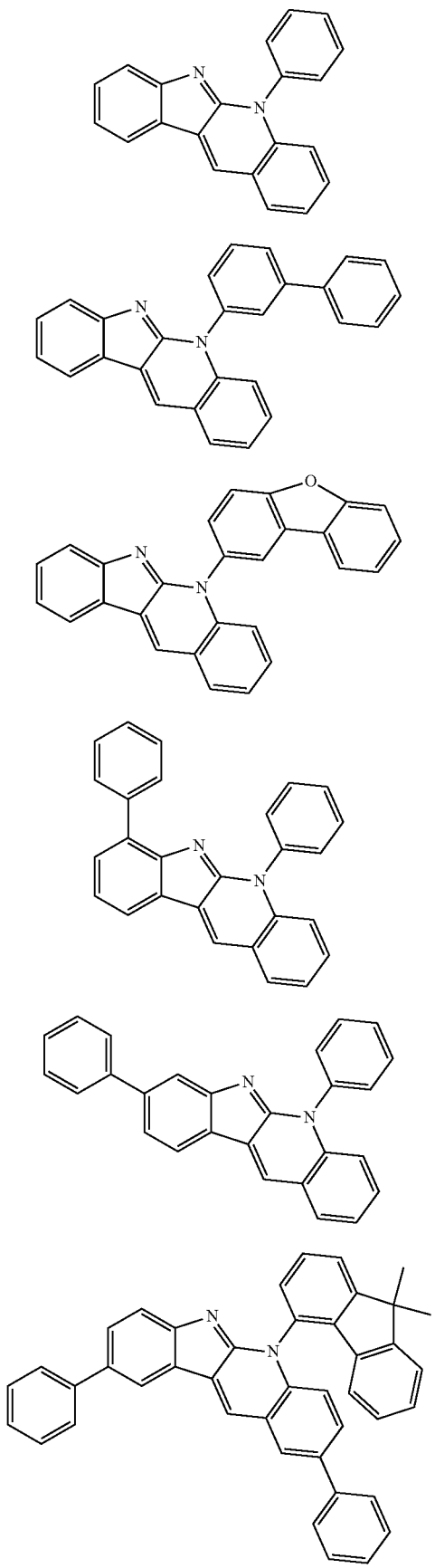
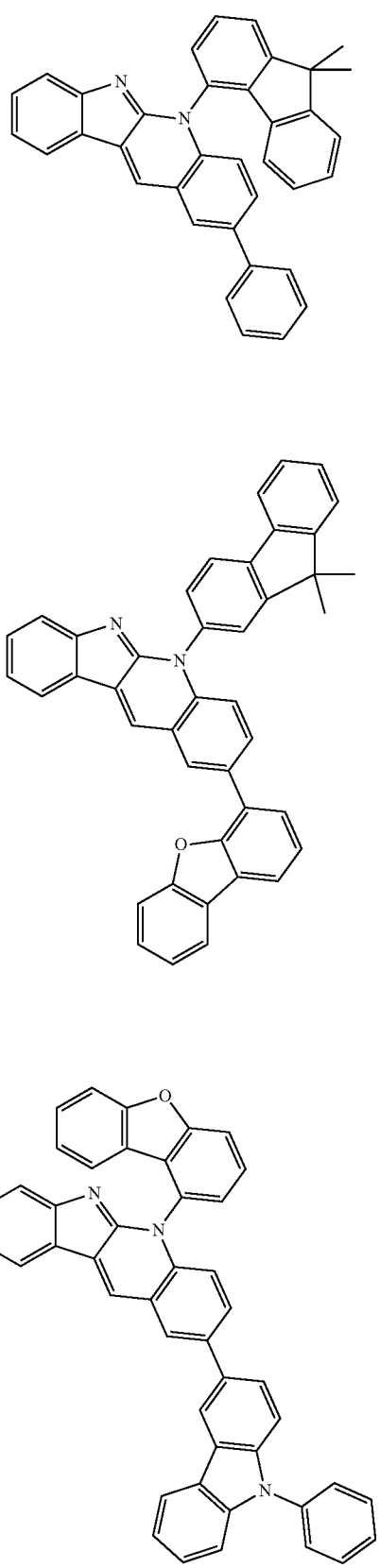

-continued
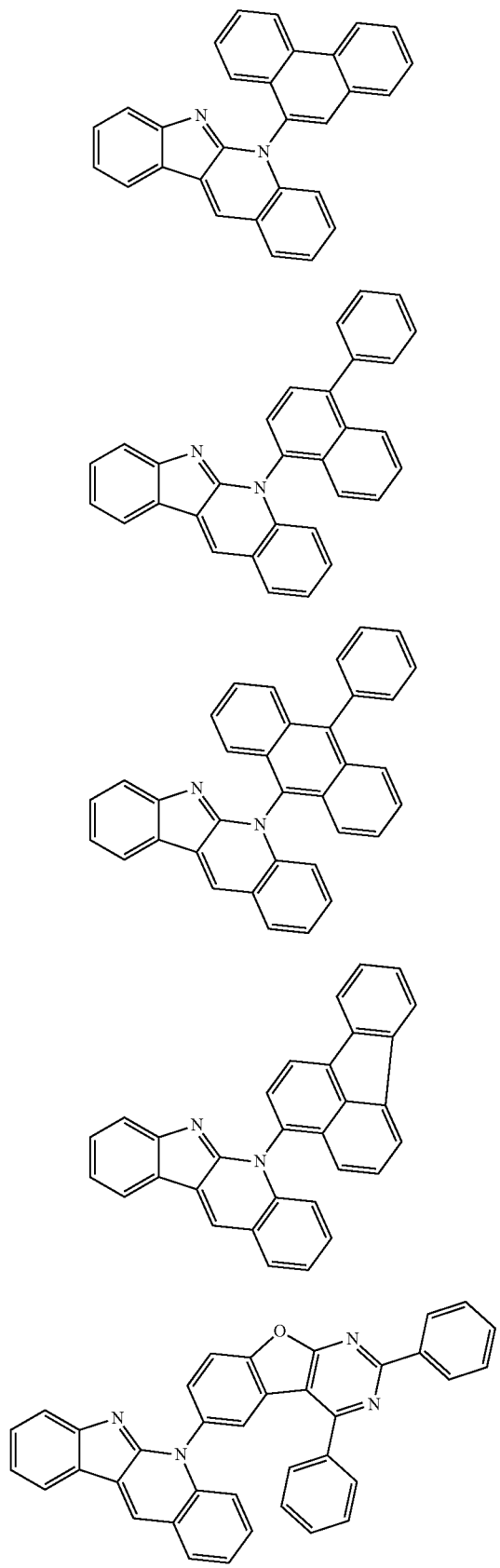
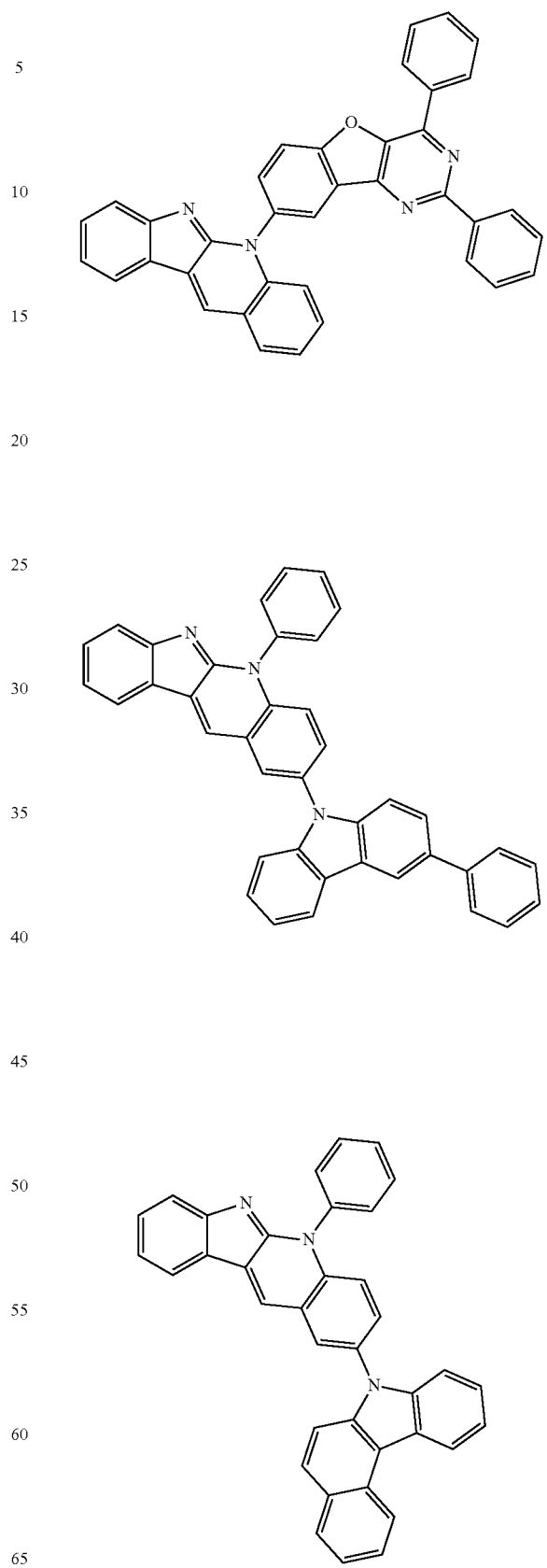

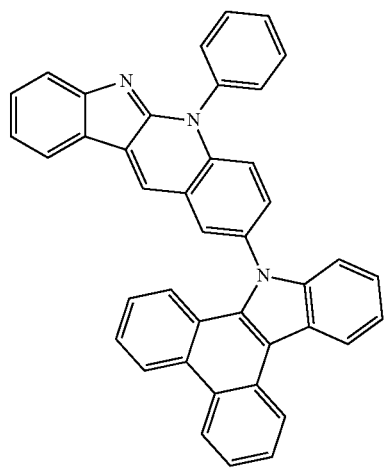 [SMILES: c1ccc(-n2c3nc4ccccc4c-3cc3cc(-n4c5ccccc5c5c6ccccc6c6ccccc6c54)ccc32)cc1]
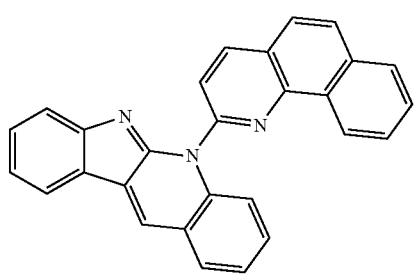 [SMILES: c1ccc2c(c1)ccc1ccc(-n3c4nc5ccccc5c-4cc4ccccc43)nc12]
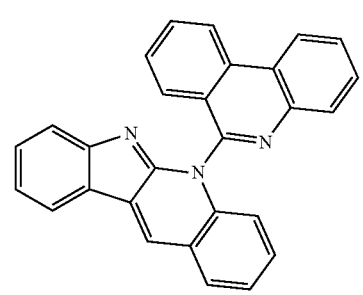 [SMILES: c1ccc2c(c1)cc1c3ccccc3nc-1n2-c1nc2ccccc2c2ccccc12]
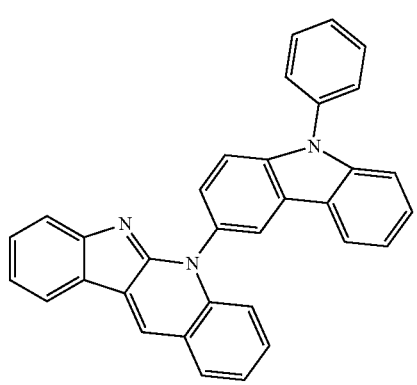 [SMILES: c1ccc(-n2c3ccccc3c3cc(-n4c5nc6ccccc6c-5cc5ccccc54)ccc32)cc1]
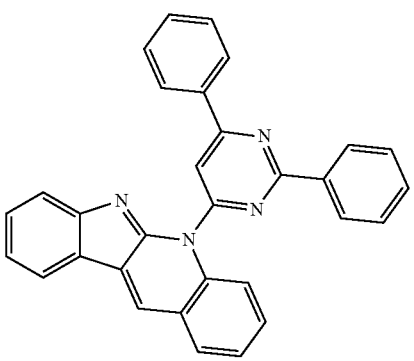 [SMILES: c1ccc(-c2cc(-n3c4nc5ccccc5c-4cc4ccccc43)nc(-c3ccccc3)n2)cc1]
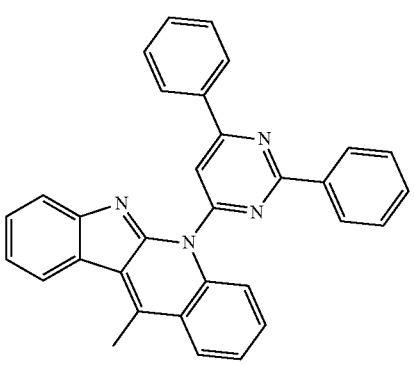 [SMILES: Cc1c2c3ccccc3nc-2n(-c2cc(-c3ccccc3)nc(-c3ccccc3)n2)c2ccccc12]
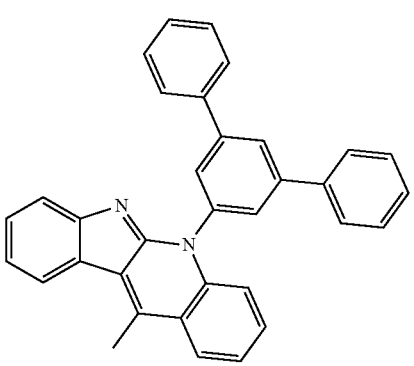 [SMILES: Cc1c2c3ccccc3nc-2n(-c2cc(-c3ccccc3)cc(-c3ccccc3)c2)c2ccccc12]

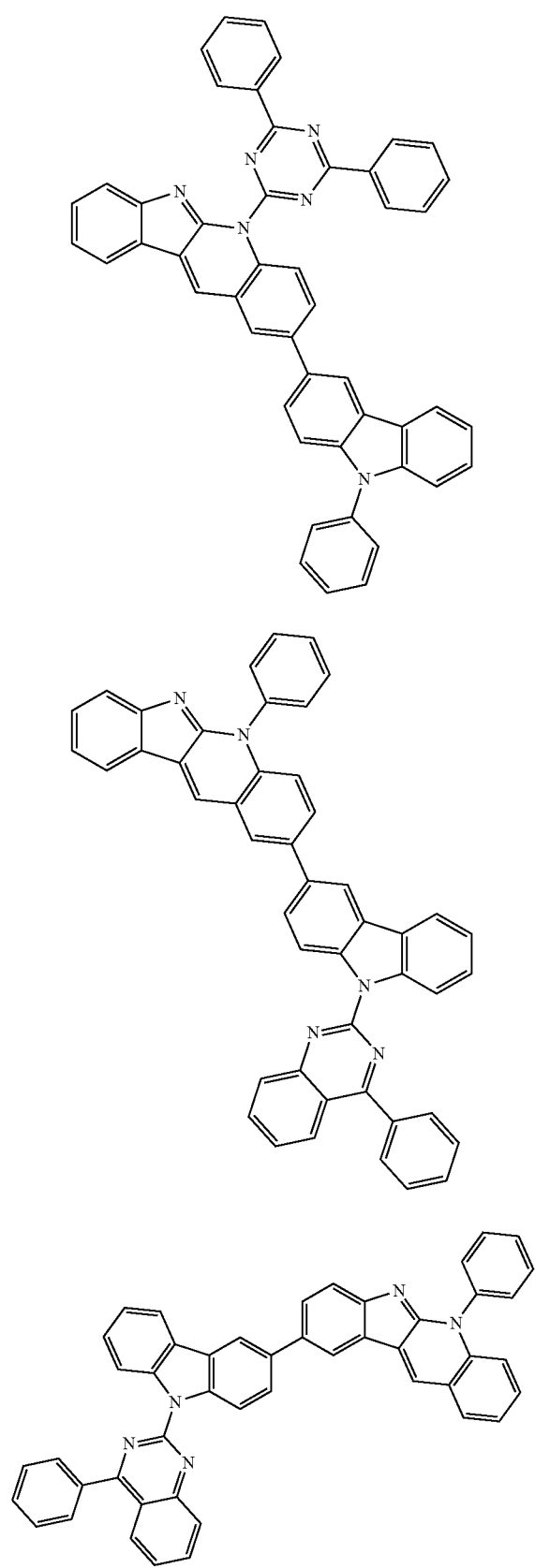
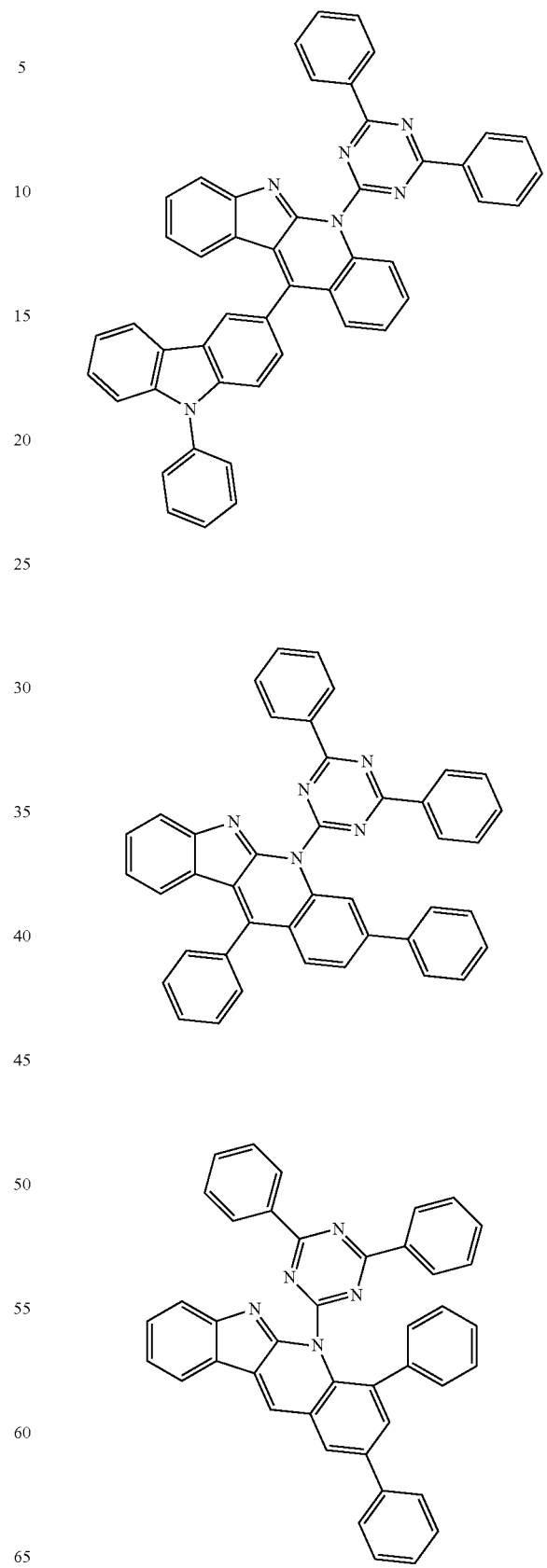

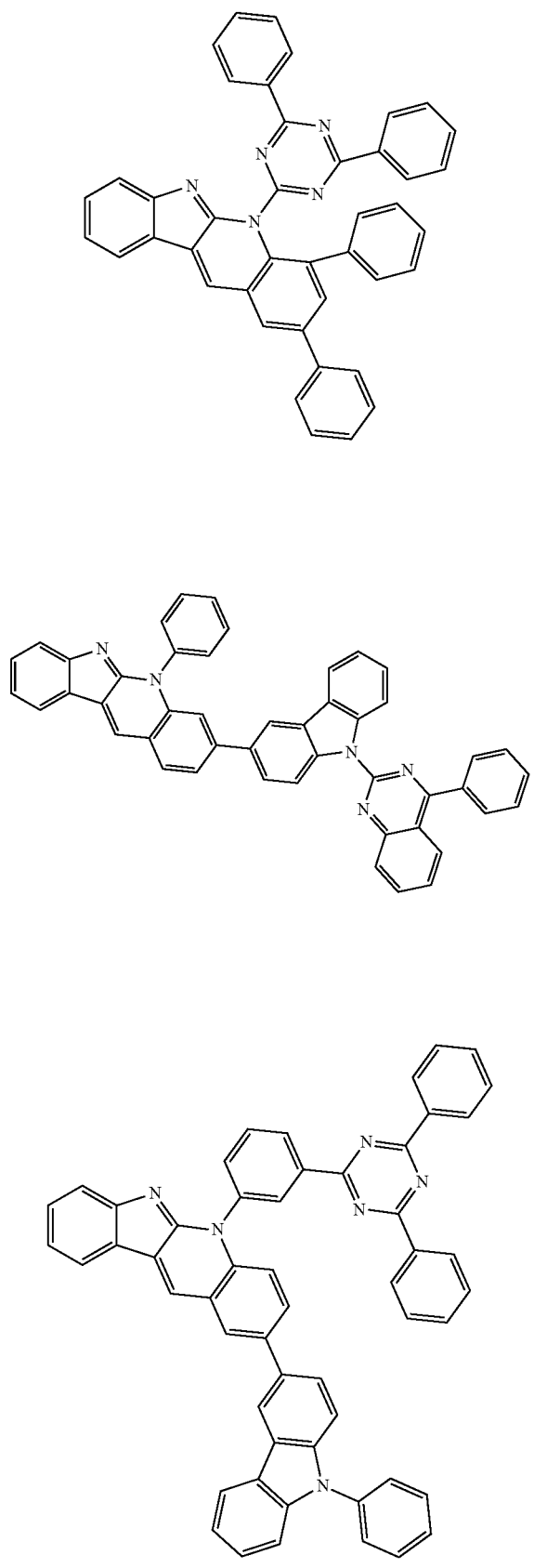
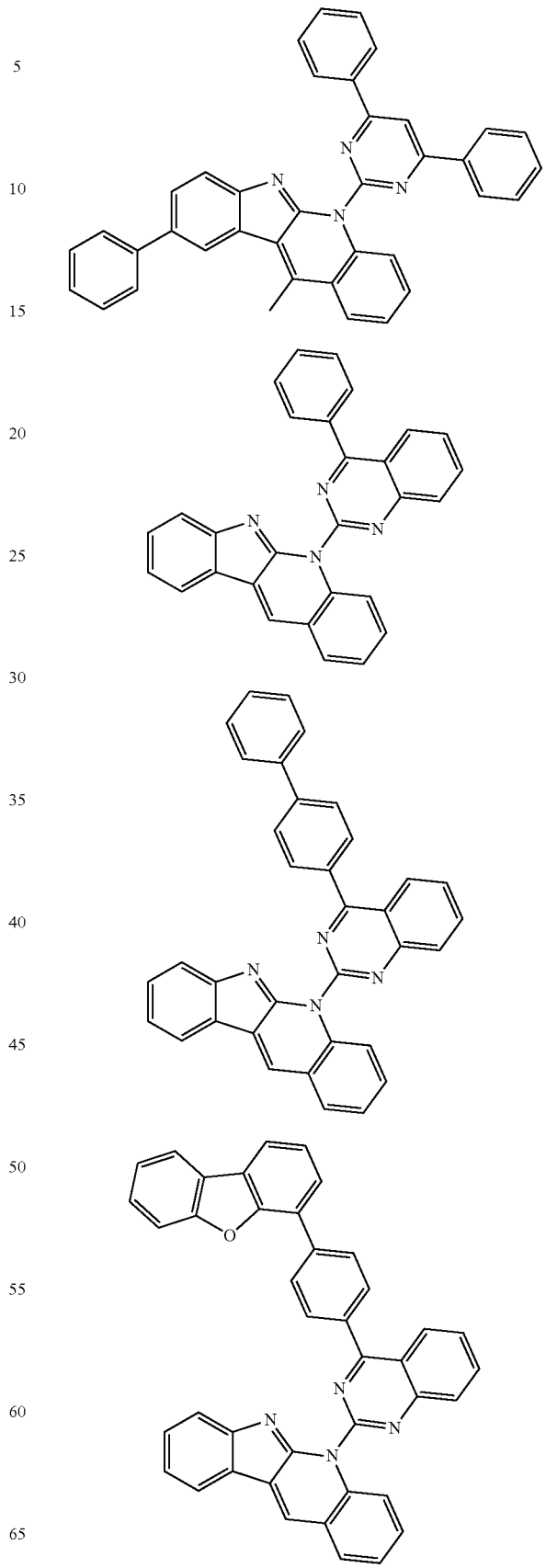

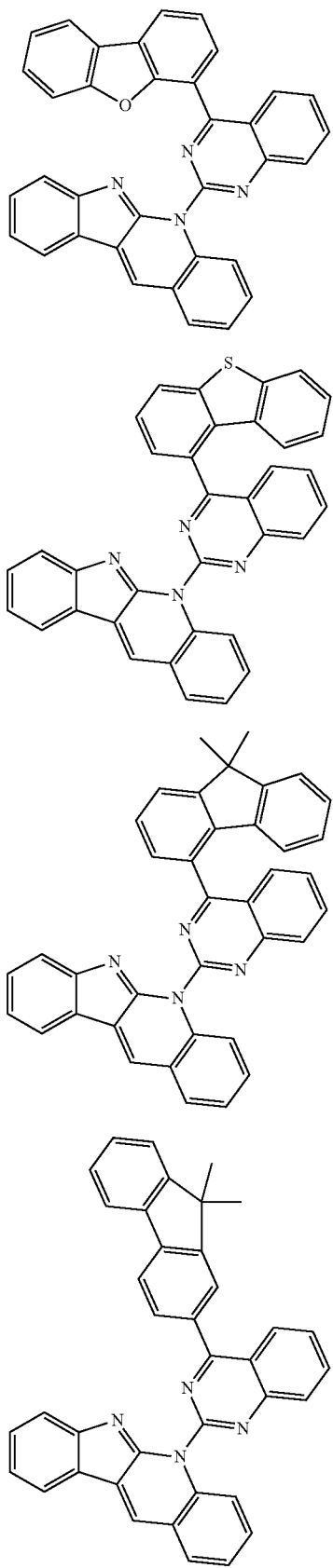
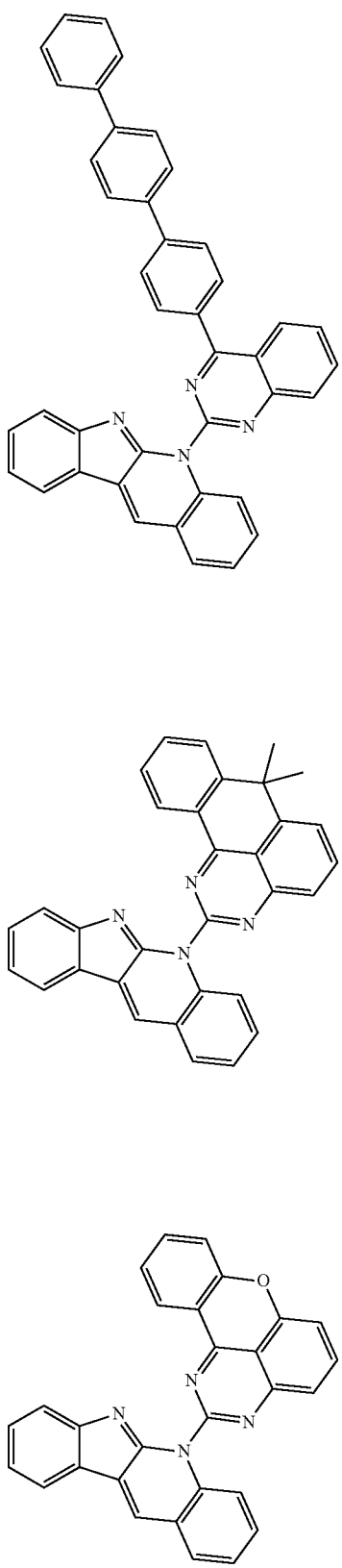

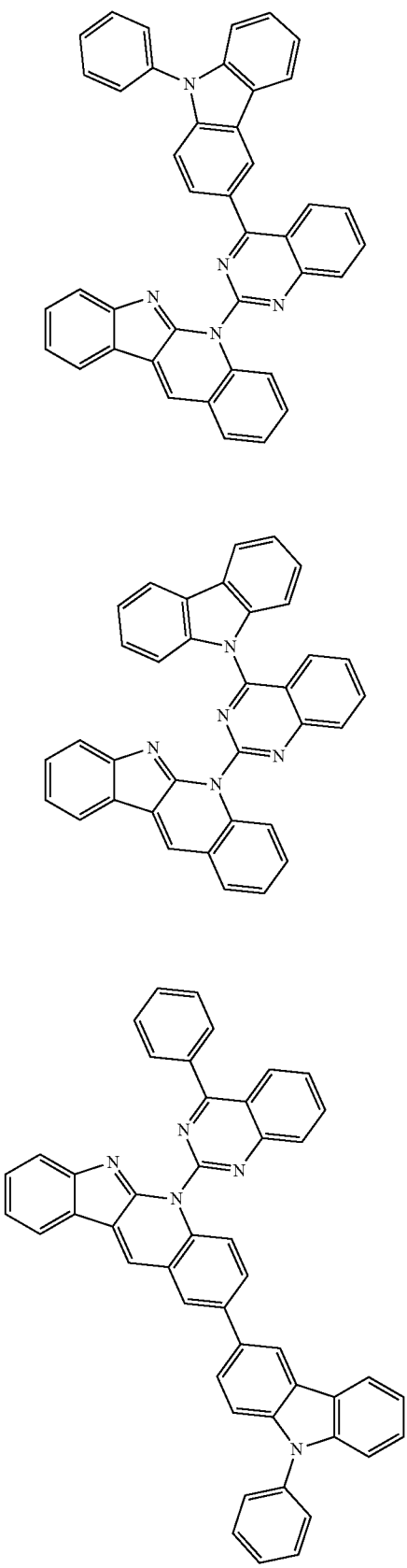
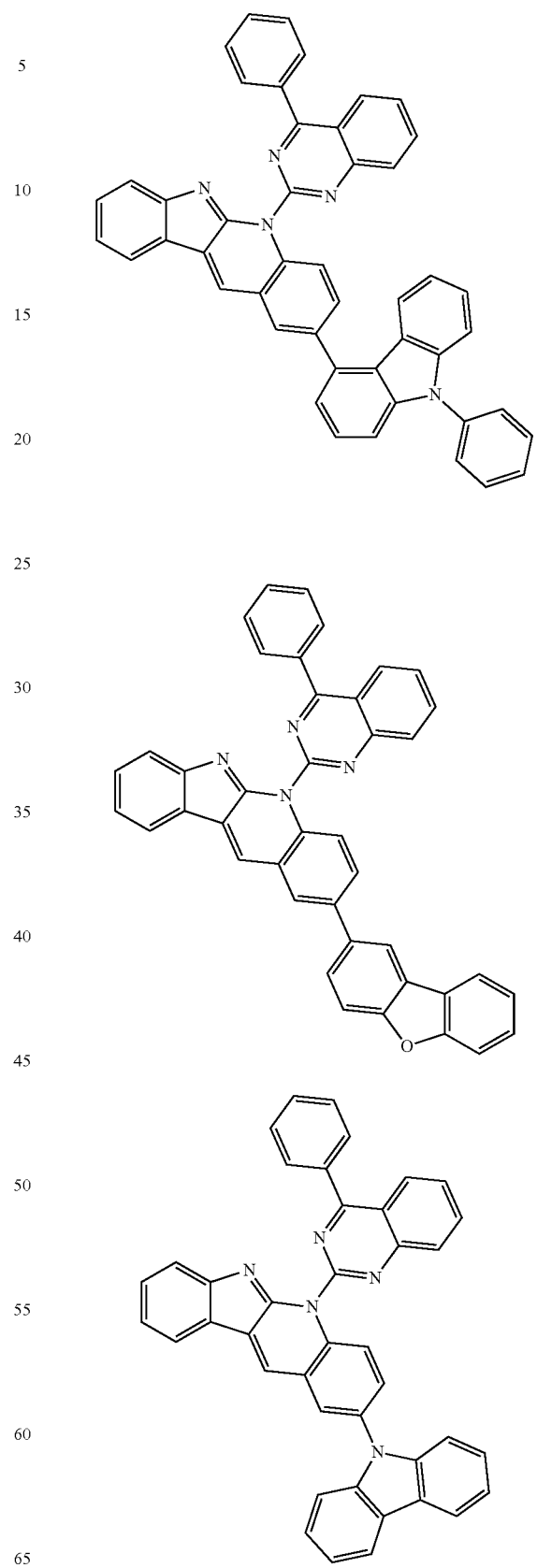

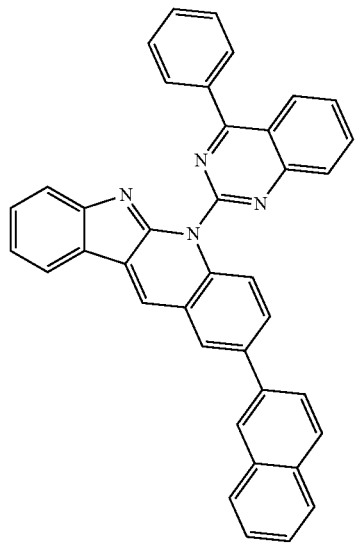 [SMILES: c1ccc(-c2nc(-n3c4nc5ccccc5c-4cc4cc(-c5ccc6ccccc6c5)ccc43)nc3ccccc23)cc1]
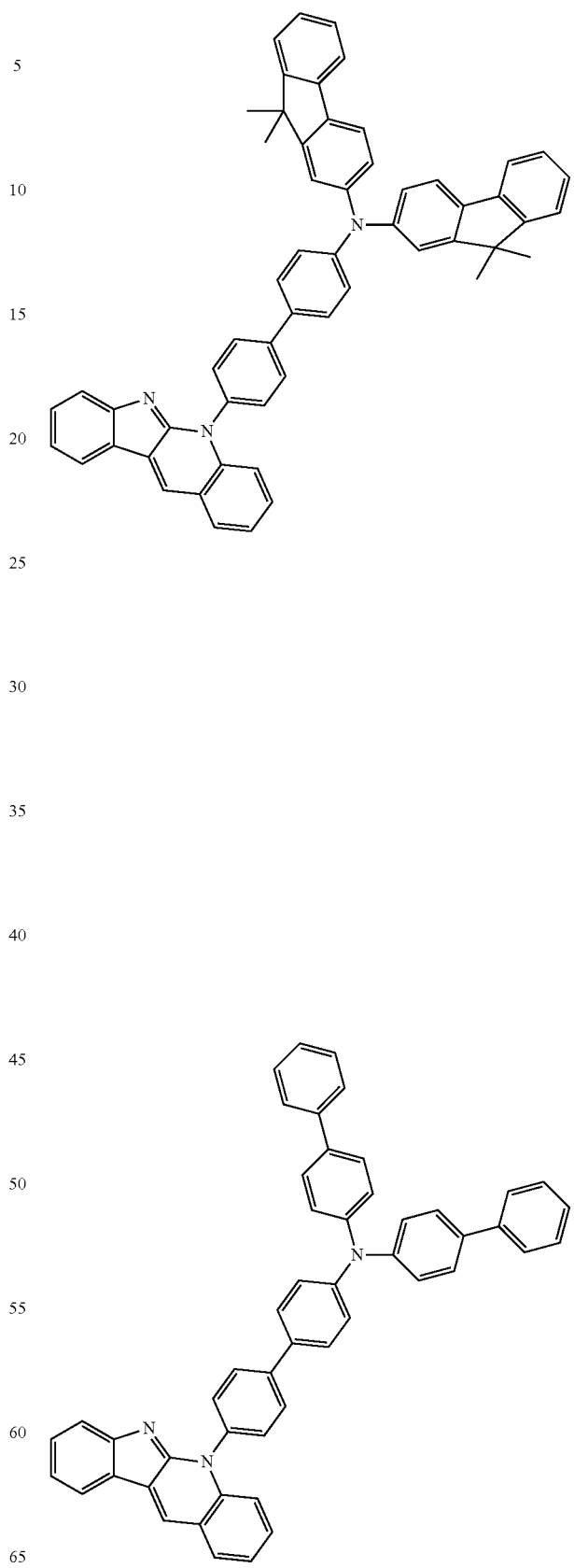

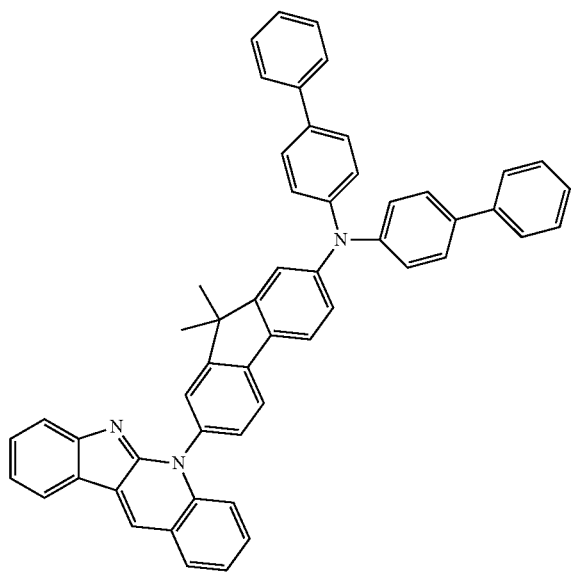 [SMILES: CC1(C)c2cc(N(c3ccc(-c4ccccc4)cc3)c3ccc(-c4ccccc4)cc3)ccc2-c2ccc(-n3c4nc5ccccc5c-4cc4ccccc43)cc21]
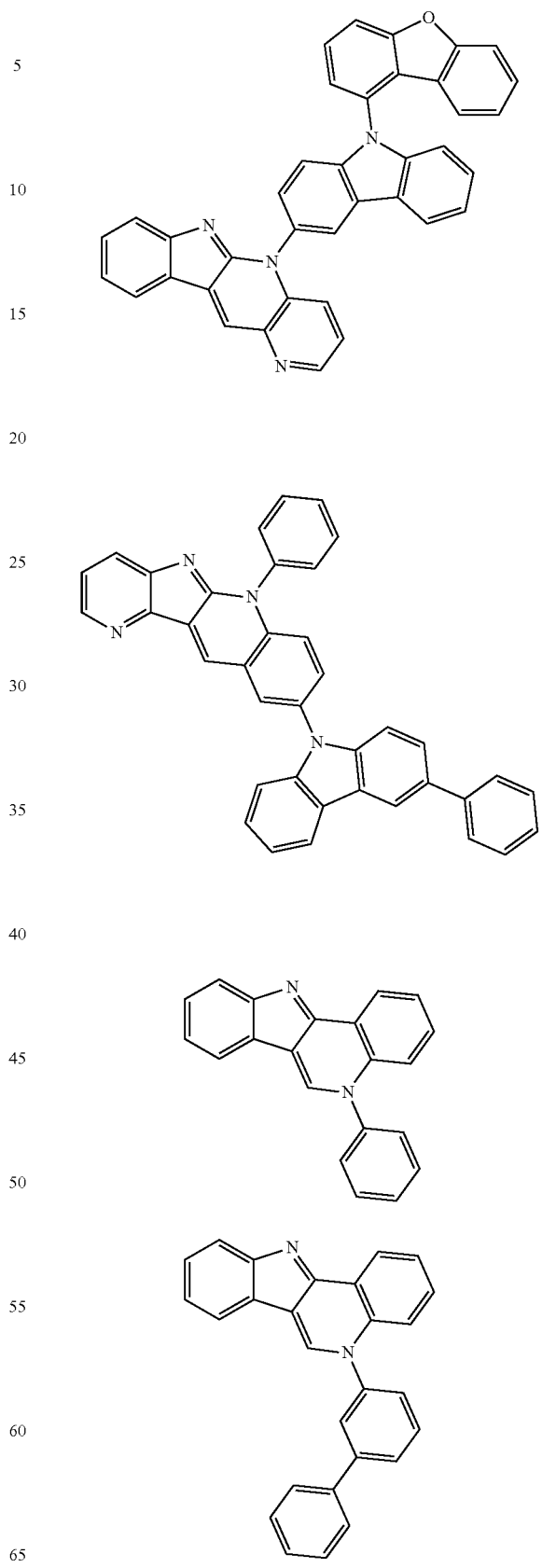

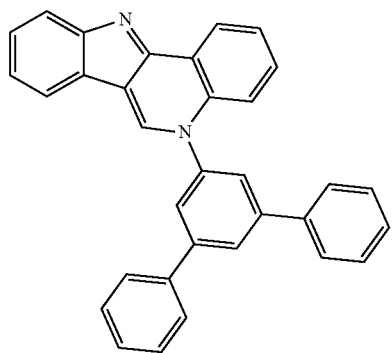 [SMILES: c1ccc(-c2cc(-c3ccccc3)cc(-n3cc4c5ccccc5nc-4c4ccccc43)c2)cc1]
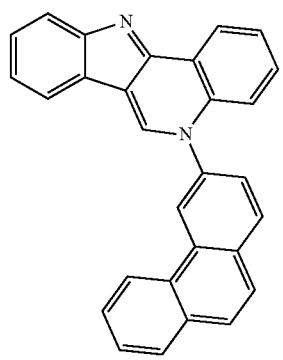 [SMILES: c1ccc2c(c1)ccc1ccc(-n3cc4c5ccccc5nc-4c4ccccc43)cc12]
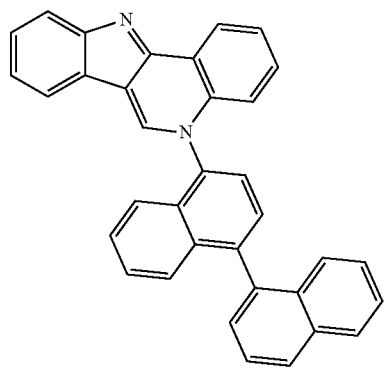 [SMILES: c1ccc2c(-c3ccc(-n4cc5c6ccccc6nc-5c5ccccc54)c4ccccc34)cccc2c1]
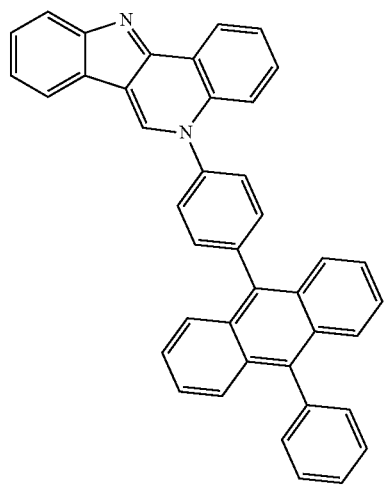 [SMILES: c1ccc(-c2c3ccccc3c(-c3ccc(-n4cc5c6ccccc6nc-5c5ccccc54)cc3)c3ccccc23)cc1]
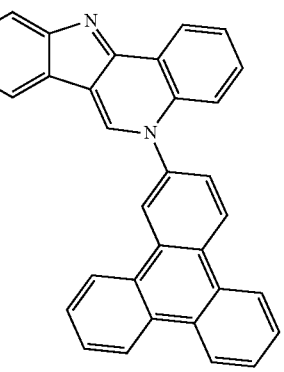
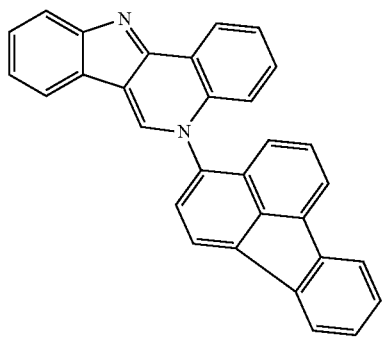 [SMILES: c1ccc2c(c1)-c1cccc3c(-n4cc5c6ccccc6nc-5c5ccccc54)ccc-2c13]
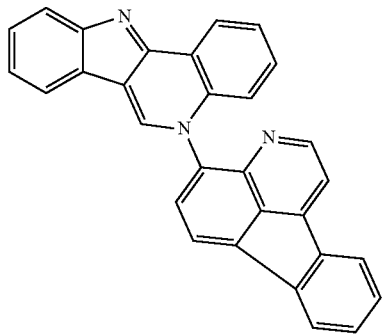 [SMILES: c1ccc2c(c1)-c1ccnc3c(-n4cc5c6ccccc6nc-5c5ccccc54)ccc-2c13]
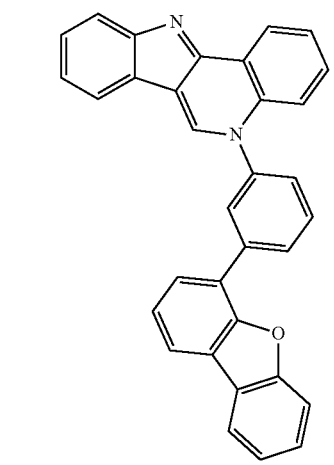 [SMILES: c1cc(-c2cccc3c2oc2ccccc23)cc(-n2cc3c4ccccc4nc-3c3ccccc32)c1]

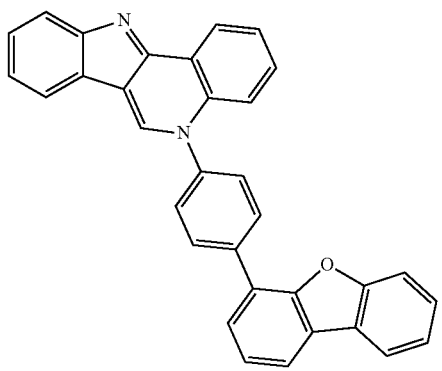 [SMILES: c1ccc2c3cn(-c4ccc(-c5cccc6c5oc5ccccc56)cc4)c4ccccc4c-3nc2c1]
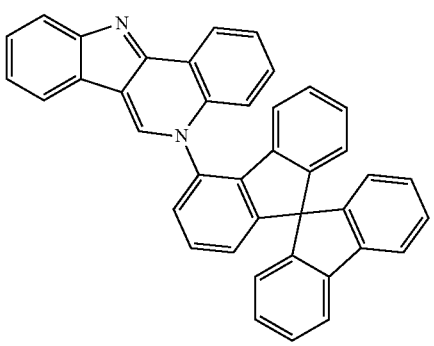
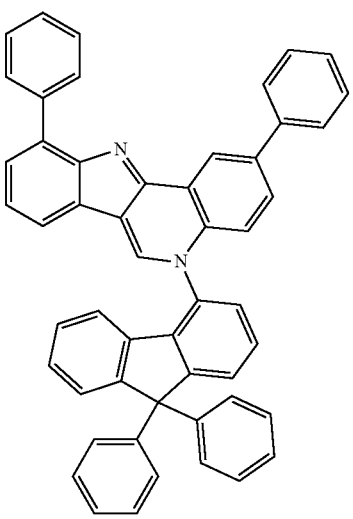
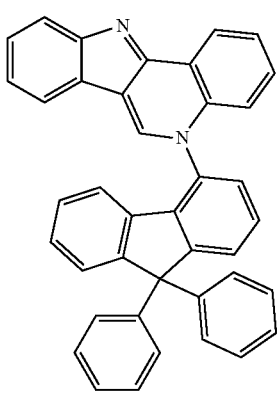 [SMILES: c1ccc(C2(c3ccccc3)c3ccccc3-c3c(-n4cc5c6ccccc6nc-5c5ccccc54)cccc32)cc1]
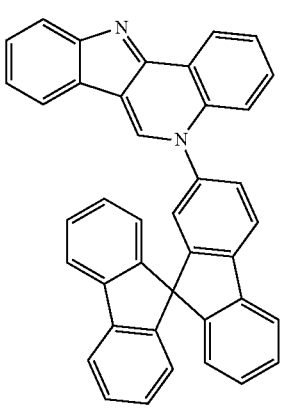 [SMILES: c1ccc2c(c1)-c1ccccc1C21c2ccccc2-c2ccc(-n3cc4c5ccccc5nc-4c4ccccc43)cc21]
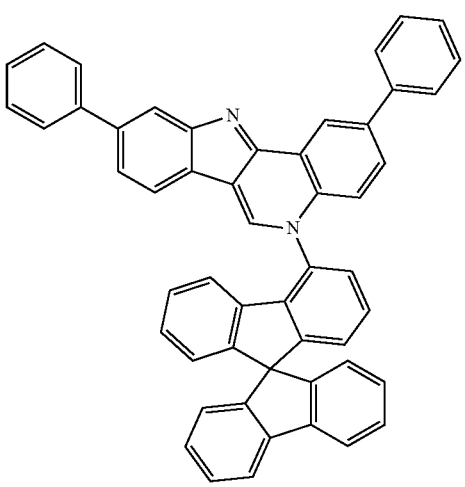 [SMILES: c1ccc(-c2ccc3c4cn(-c5cccc6c5-c5ccccc5C65c6ccccc6-c6ccccc65)c5ccc(-c6ccccc6)cc5c-4nc3c2)cc1]

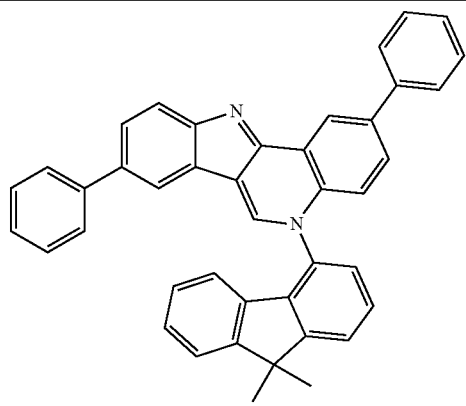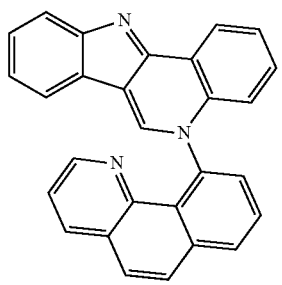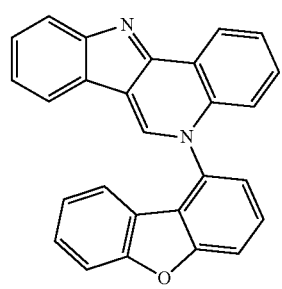 [SMILES: c1ccc2c3cn(-c4cccc5oc6ccccc6c45)c4ccccc4c-3nc2c1]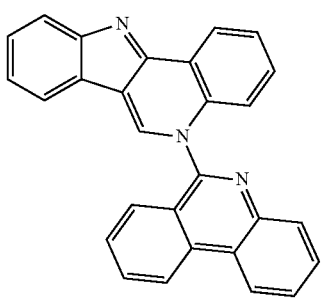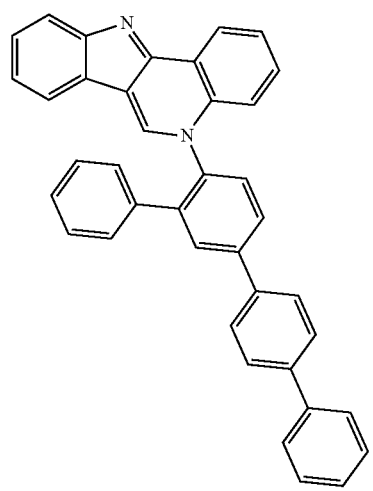 [SMILES: c1ccc(-c2ccc(-c3ccc(-n4cc5c6ccccc6nc-5c5ccccc54)c(-c4ccccc4)c3)cc2)cc1]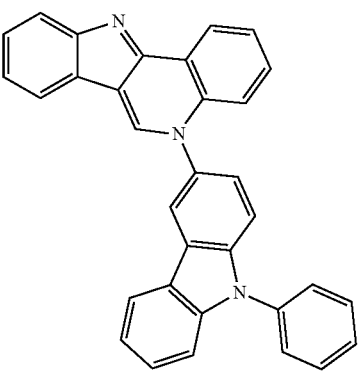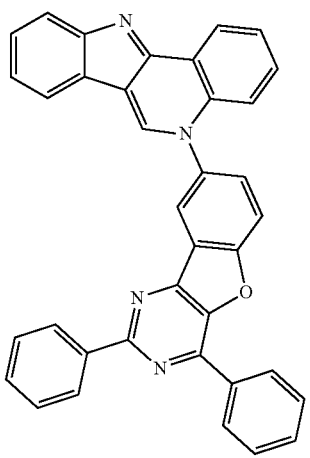 [SMILES: c1ccc(-c2nc(-c3ccccc3)c3oc4ccc(-n5cc6c7ccccc7nc-6c6ccccc65)cc4c3n2)cc1]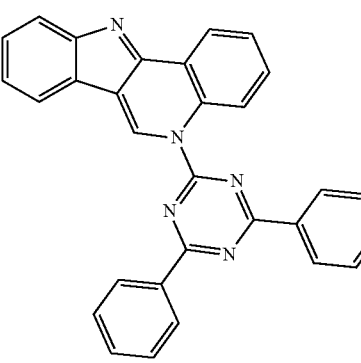

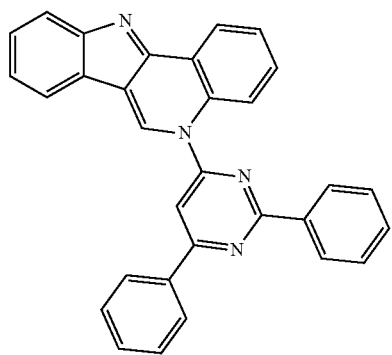
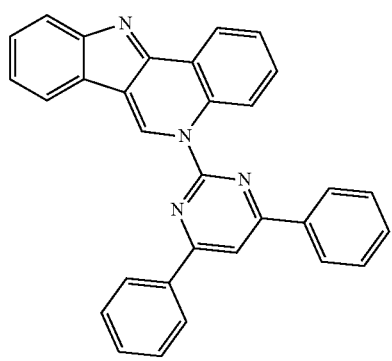 [SMILES: c1ccc(-c2nc(-c3ccccc3)nc(-n3cc4c5ccccc5nc-4c4ccccc43)n2)cc1]
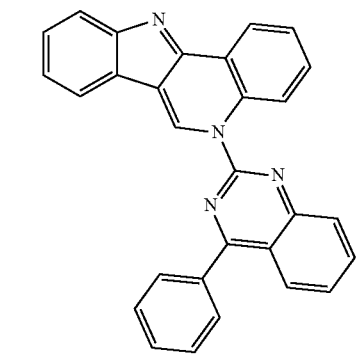 [SMILES: c1ccc(-c2nc(-n3cc4c5ccccc5nc-4c4ccccc43)nc3ccccc23)cc1]
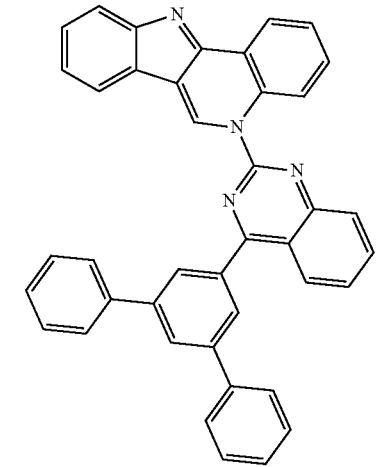 [SMILES: c1ccc(-c2cc(-c3ccccc3)cc(-c3nc(-n4cc5c6ccccc6nc-5c5ccccc54)nc4ccccc34)c2)cc1]
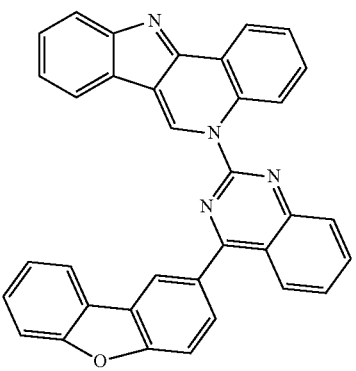 [SMILES: c1ccc2c3cn(-c4nc(-c5ccc6oc7ccccc7c6c5)c5ccccc5n4)c4ccccc4c-3nc2c1]
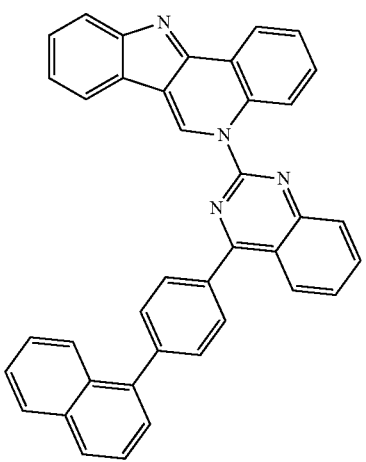 [SMILES: c1ccc2c(-c3ccc(-c4nc(-n5cc6c7ccccc7nc-6c6ccccc65)nc5ccccc45)cc3)cccc2c1]
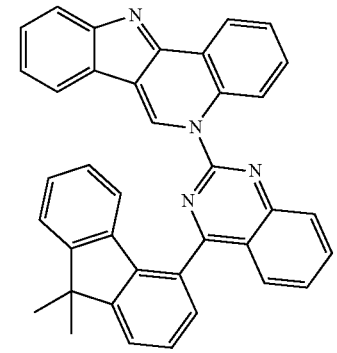 [SMILES: CC1(C)c2ccccc2-c2c(-c3nc(-n4cc5c6ccccc6nc-5c5ccccc54)nc4ccccc34)cccc21]
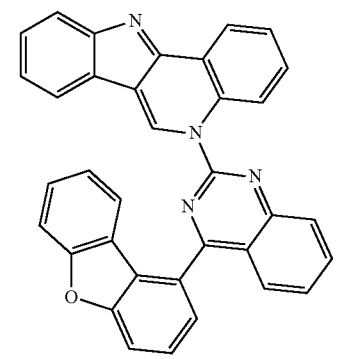 [SMILES: c1ccc2c3cn(-c4nc(-c5cccc6oc7ccccc7c56)c5ccccc5n4)c4ccccc4c-3nc2c1]

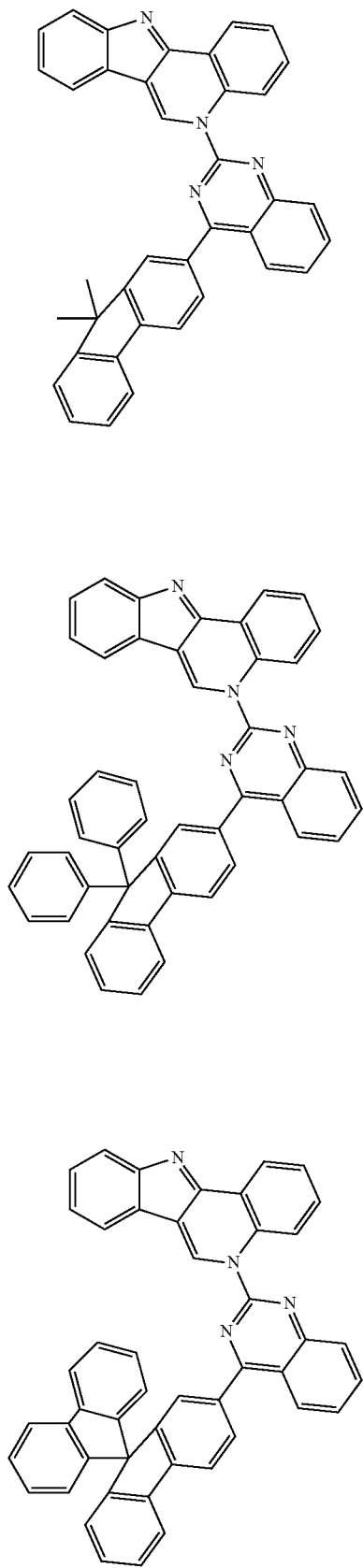
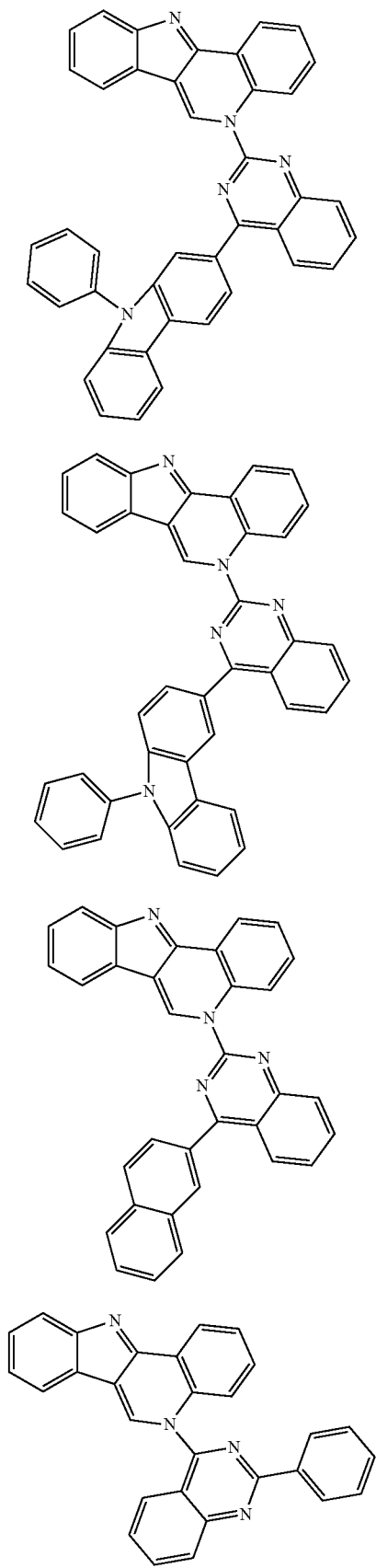

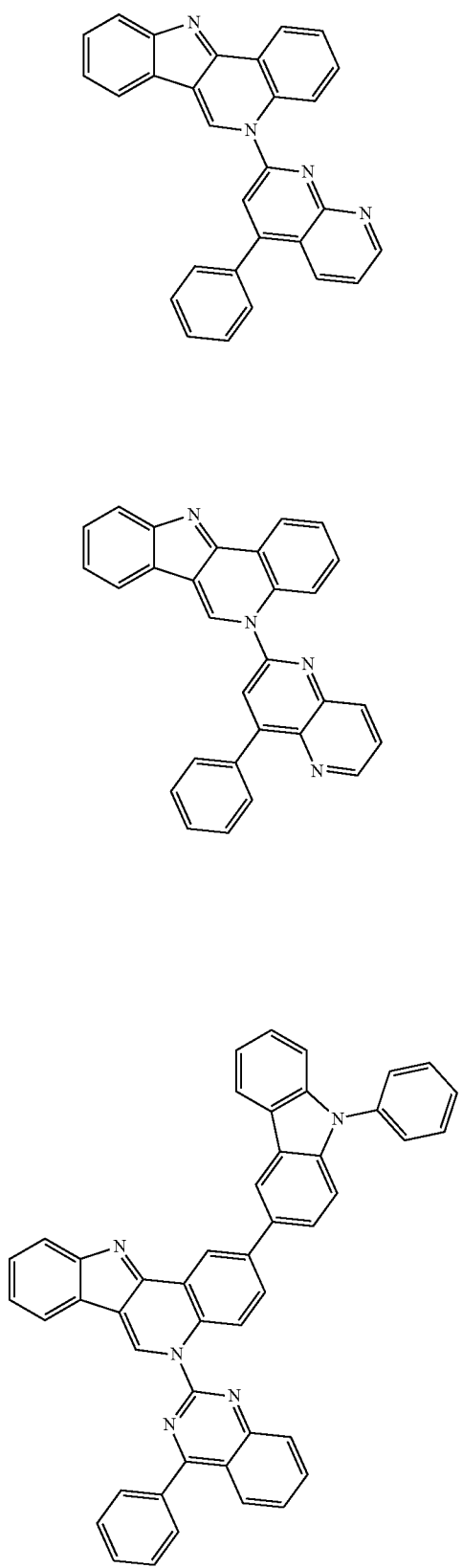
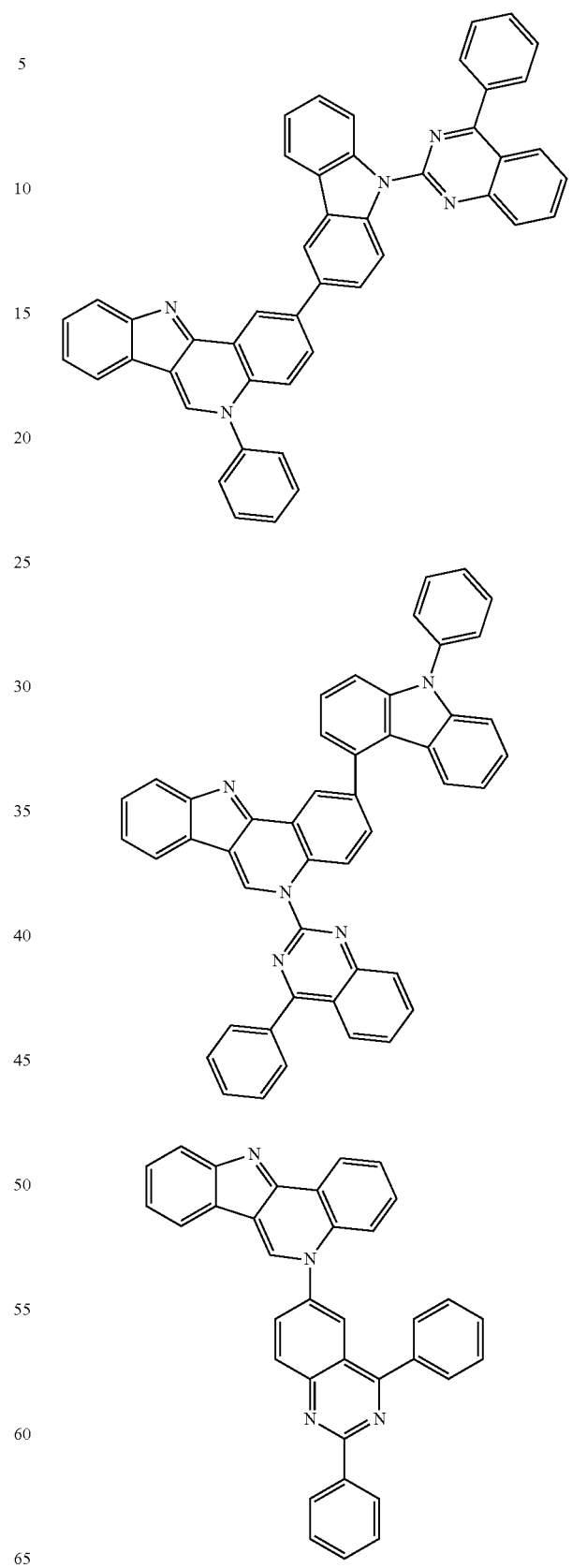

-continued
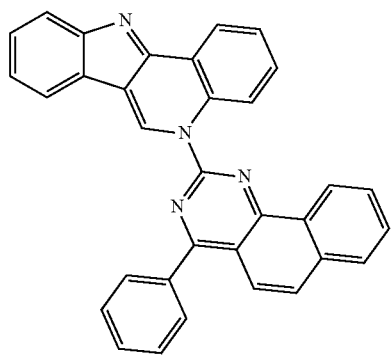 [SMILES: c1ccc(-c2nc(-n3cc4c5ccccc5nc-4c4ccccc43)nc3c2ccc2ccccc23)cc1]
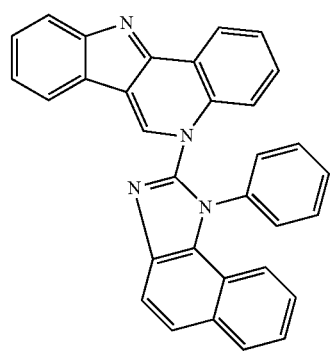 [SMILES: c1ccc(-n2c(-n3cc4c5ccccc5nc-4c4ccccc43)nc3ccc4ccccc4c32)cc1]
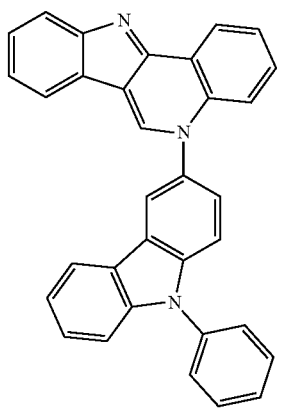 [SMILES: c1ccc(-n2c3ccccc3c3cc(-n4cc5c6ccccc6nc-5c5ccccc54)ccc32)cc1]
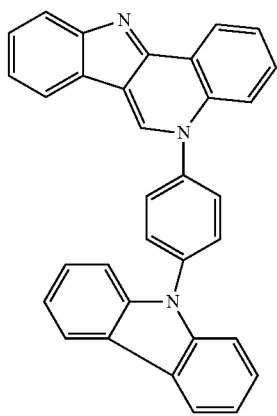 [SMILES: c1ccc2c3cn(-c4ccc(-n5c6ccccc6c6ccccc65)cc4)c4ccccc4c-3nc2c1]
-continued
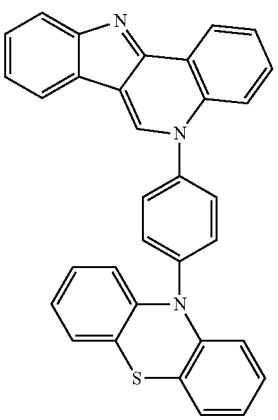 [SMILES: c1ccc2c(c1)Sc1ccccc1N2c1ccc(-n2cc3c4ccccc4nc-3c3ccccc32)cc1]
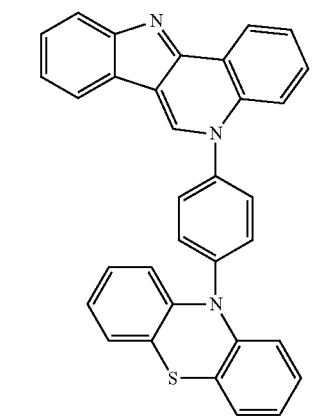
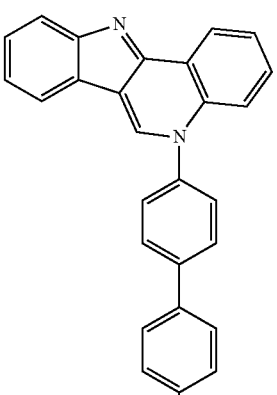
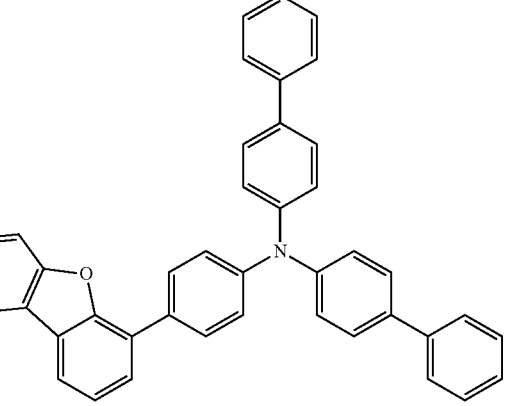

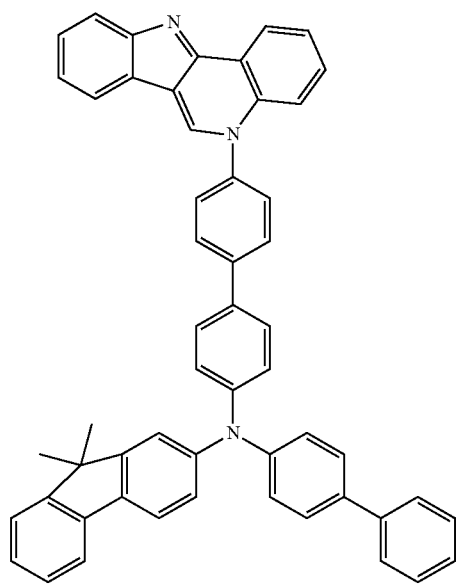 [SMILES: CC1(C)c2ccccc2-c2ccc(N(c3ccc(-c4ccccc4)cc3)c3ccc(-c4ccc(-n5cc6c7ccccc7nc-6c6ccccc65)cc4)cc3)cc21]
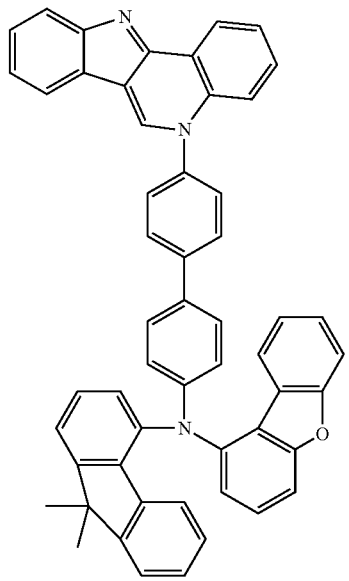 [SMILES: CC1(C)c2ccccc2-c2c(N(c3ccc(-c4ccc(-n5cc6c7ccccc7nc-6c6ccccc65)cc4)cc3)c3cccc4oc5ccccc5c34)cccc21]
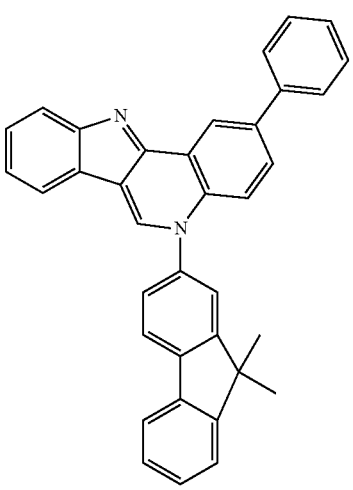 [SMILES: CC1(C)c2ccccc2-c2ccc(-n3cc4c5ccccc5nc-4c4cc(-c5ccccc5)ccc43)cc21]
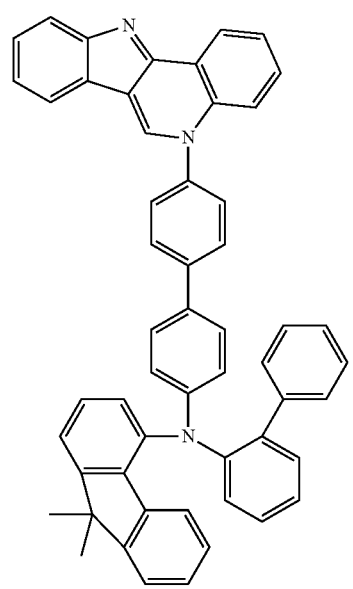
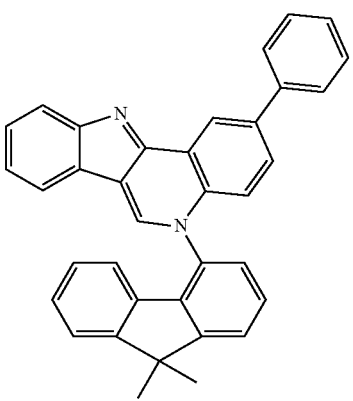 [SMILES: CC1(C)c2ccccc2-c2c(-n3cc4c5ccccc5nc-4c4cc(-c5ccccc5)ccc43)cccc21]

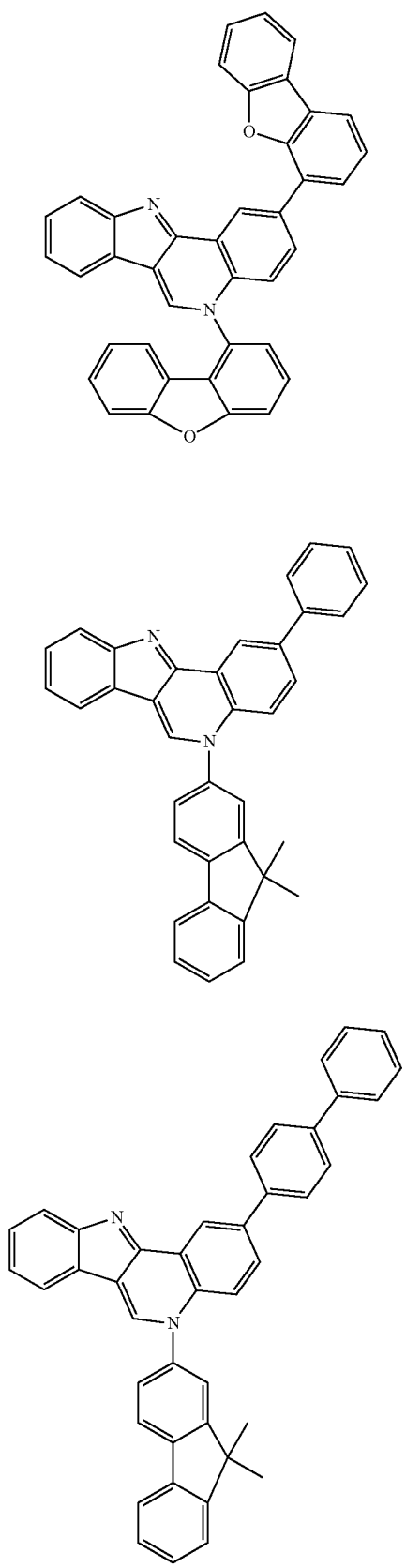
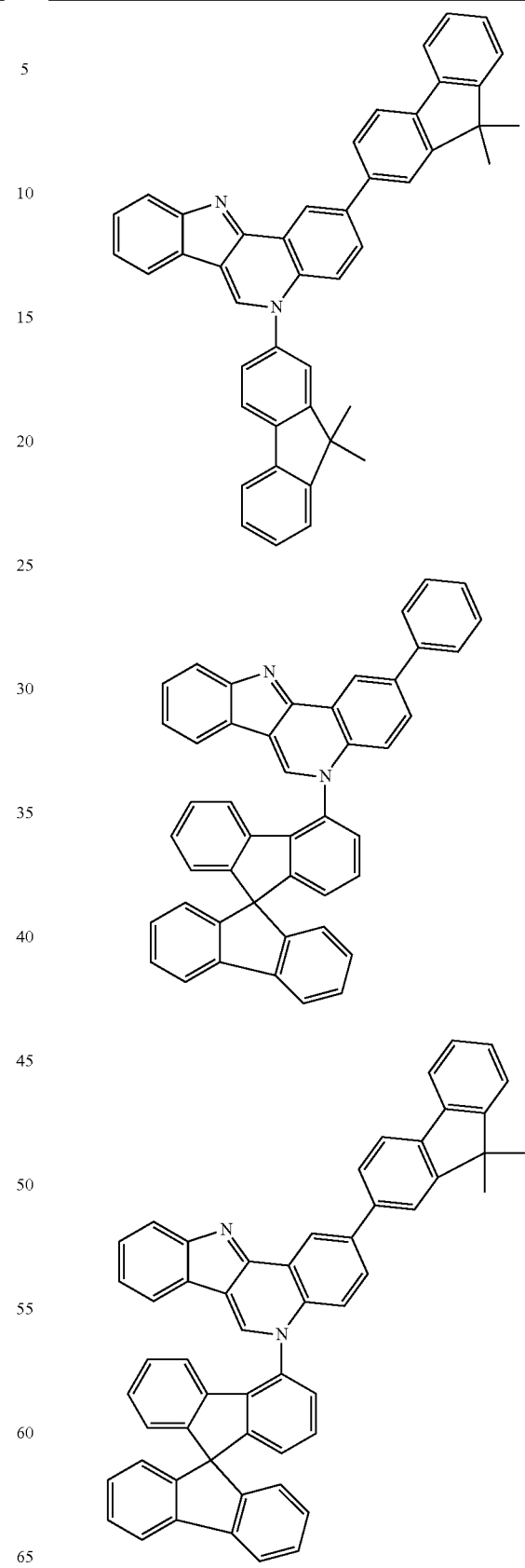

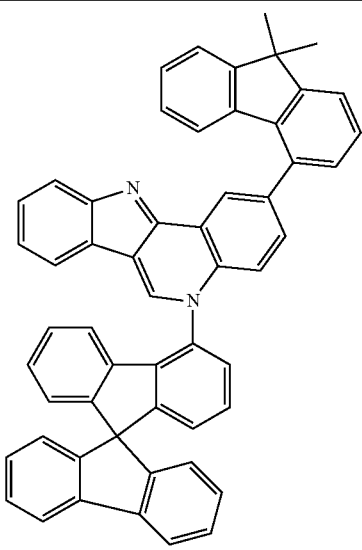

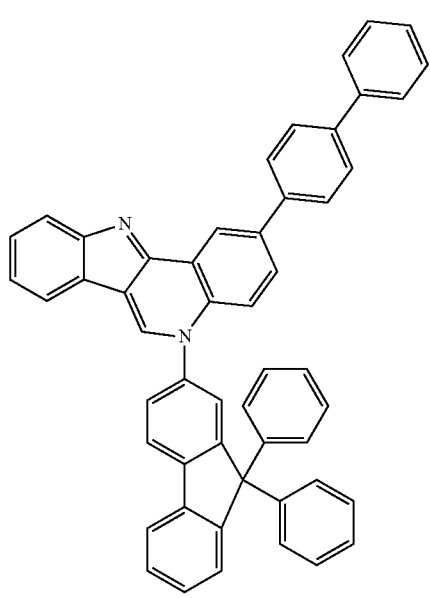 [SMILES: c1ccc(-c2ccc(-c3ccc4c(c3)c3nc5ccccc5c-3cn4-c3ccc4c(c3)C(c3ccccc3)(c3ccccc3)c3ccccc3-4)cc2)cc1]

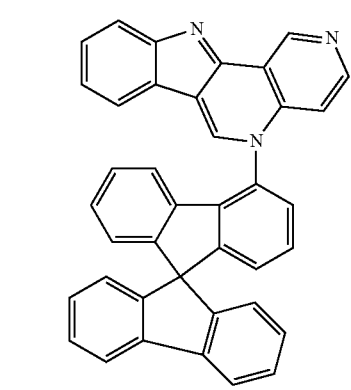 [SMILES: c1ccc2c(c1)-c1ccccc1C21c2ccccc2-c2c(-n3cc4c5ccccc5nc-4c4cnccc43)cccc21]

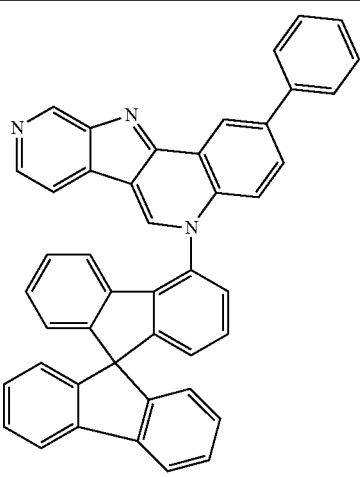

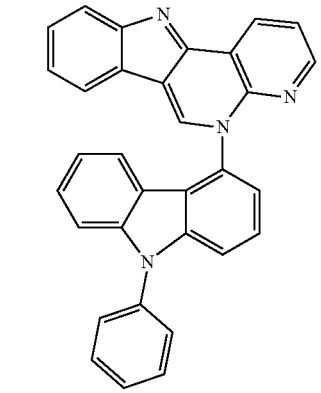 [SMILES: c1ccc(-n2c3ccccc3c3c(-n4cc5c6ccccc6nc-5c5cccnc54)cccc32)cc1]

The synthesis of the base structures of the compounds of the invention is known from the literature. For example, compounds of the formula (3) may be synthesized as shown in Scheme 1, proceeding from an optionally substituted bromoiodoquinoline. This is reacted in a Buchwald or Ullmann coupling with an optionally substituted aniline. Cyclization under palladium catalysis results in the synthesis of the base skeleton of the compounds of the formula (3). In a last step, by a Buchwald or Ullmann coupling with an aryl or heteroaryl bromide or iodide, the Ar group is introduced.

Scheme 1 (the literature references relate to the syntheses of the reactants and the corresponding general reactions):

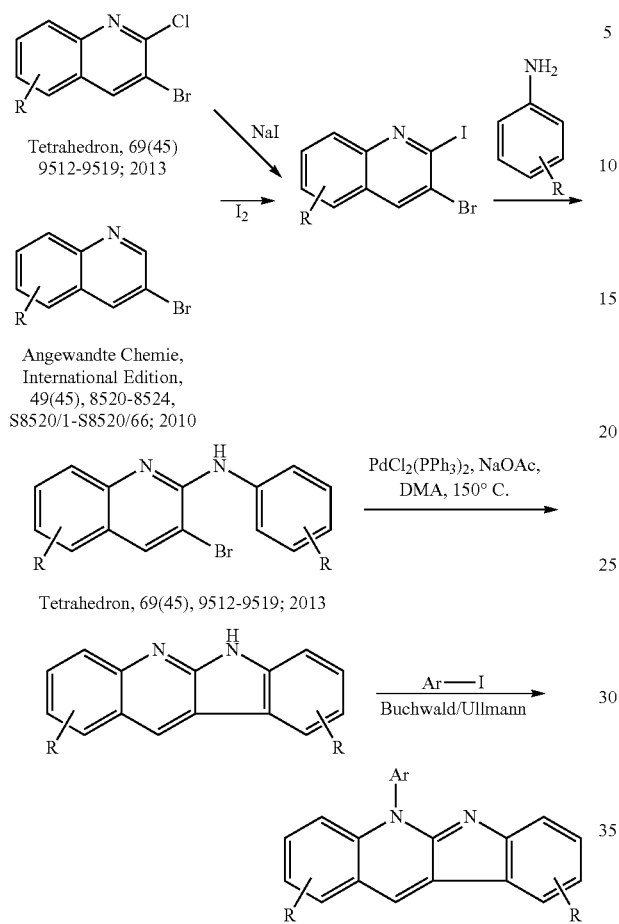

Tetrahedron, 69(45) 9512-9519; 2013

Angewandte Chemie, International Edition, 49(45), 8520-8524, S8520/1-S8520/66; 2010

Tetrahedron, 69(45), 9512-9519; 2013

The synthesis of compounds of formula (4) can be conducted as shown in Scheme 2 or 3. For instance, the base skeleton of the compounds of the formula (4) can be formed by reaction of an optionally substituted indole with benzyl azide, followed by oxidation to give the corresponding heteroaromatic system, as shown in Scheme 2. In a last step, by a Buchwald or Ullmann coupling with an aryl or heteroaryl bromide or iodide, the Ar group is introduced. Alternatively, the synthesis can be effected by a cyclization reaction with phenylhydrazinium chloride, as shown in Scheme 3, where the Ar group here is already introduced with the starting compound.

Scheme 2 (the literature reference relates to the synthesis of the base skeleton without the Ar group):

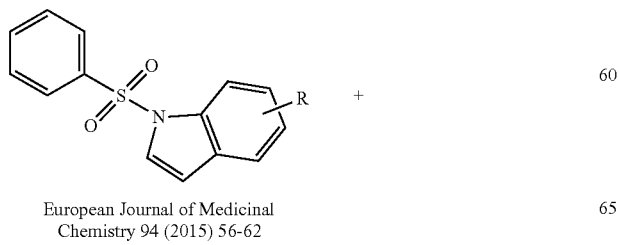

European Journal of Medicinal Chemistry 94 (2015) 56-62

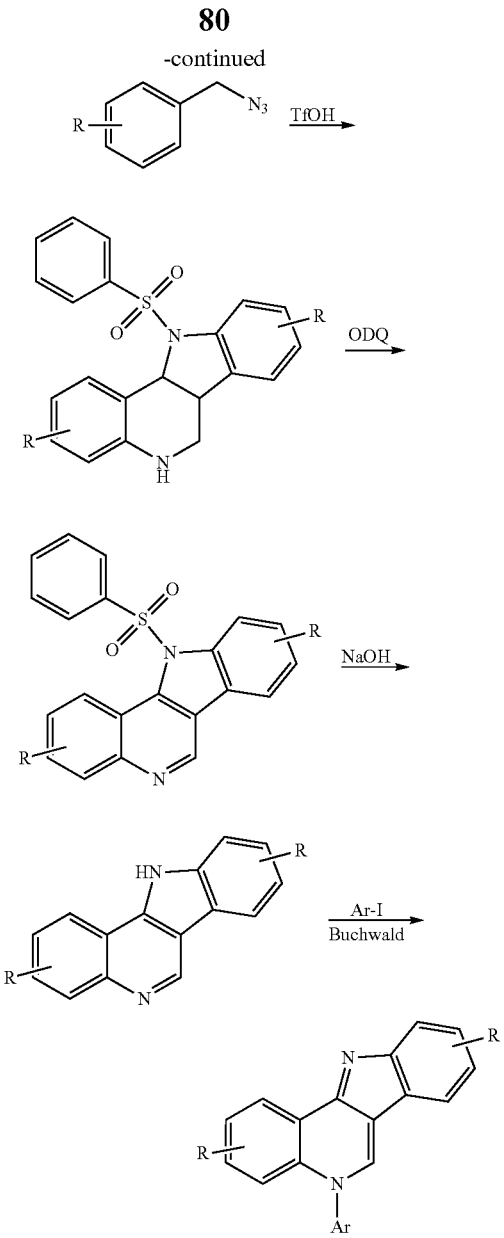

Scheme 3

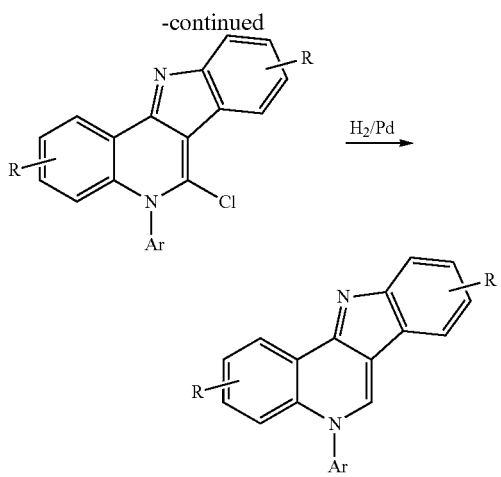

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blacker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for fluorescent or phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole blocker layer and/or in a hole transport layer and/or in an exciton blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439 and the as yet unpublished application EP16179378.1. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below,

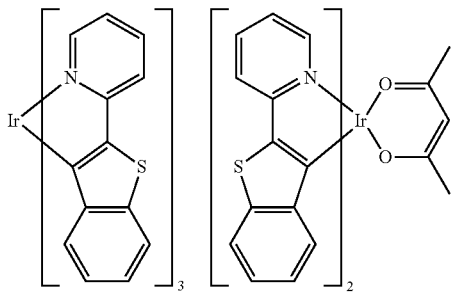

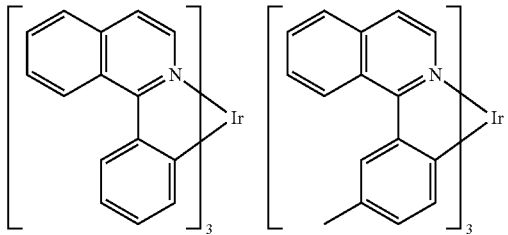

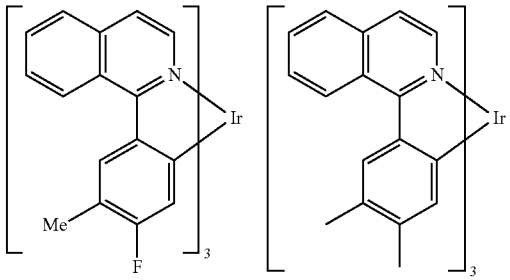

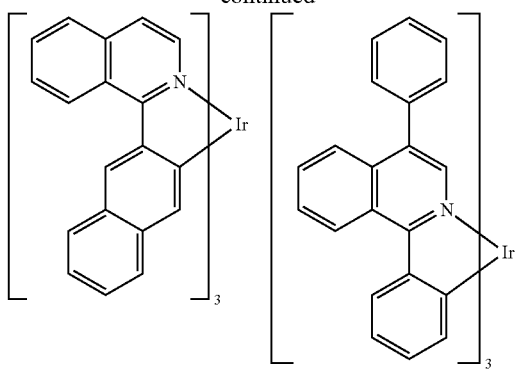
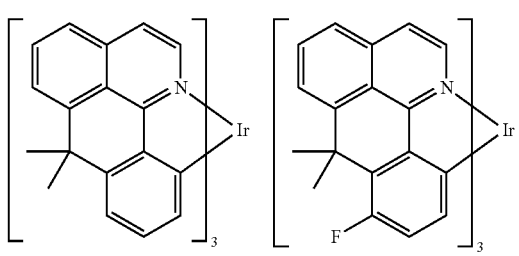
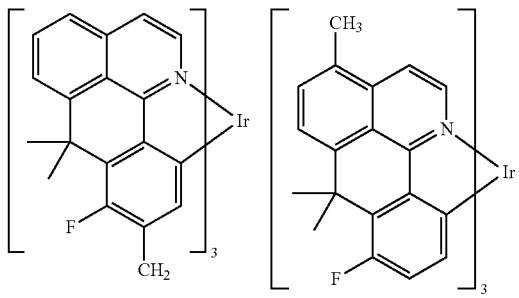
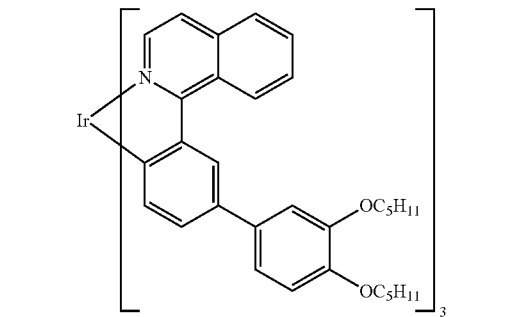
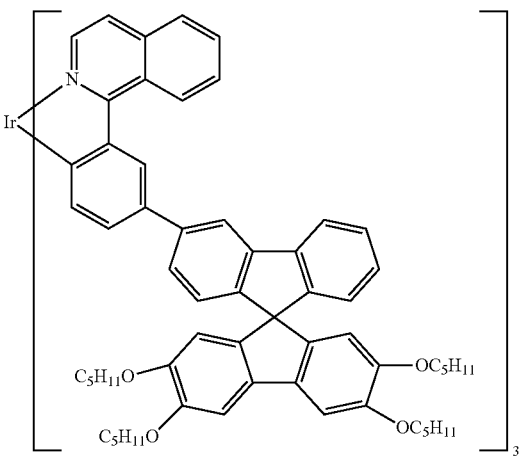

87
-continued
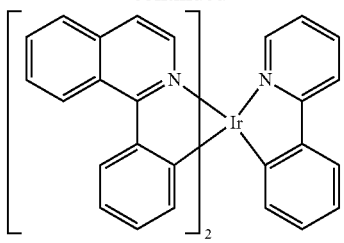
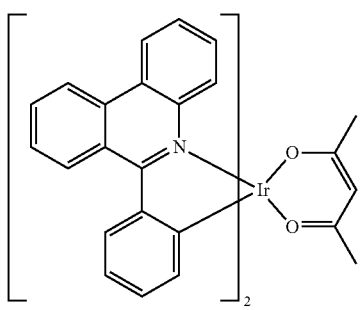
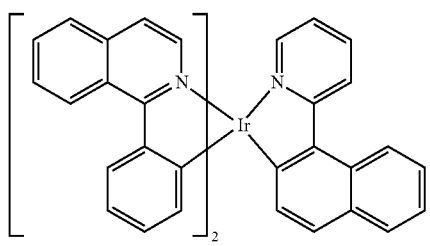
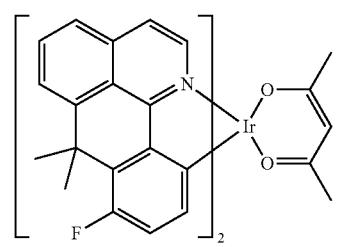
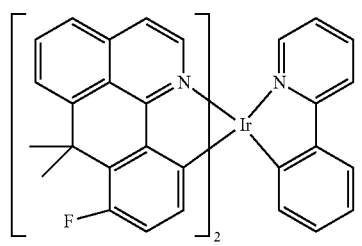
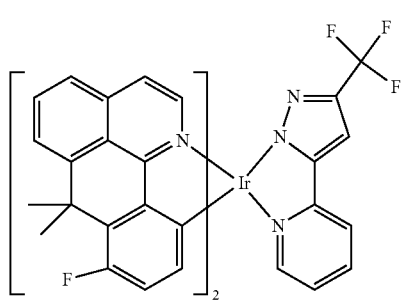
88
-continued
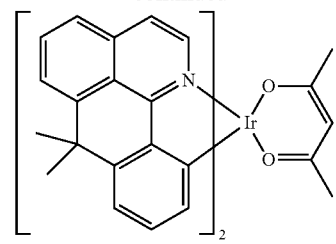
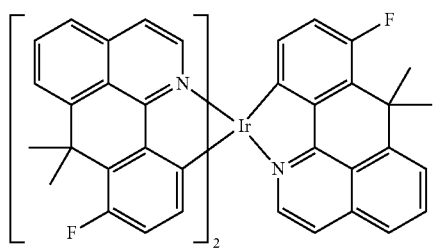
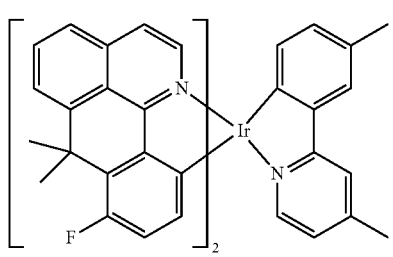
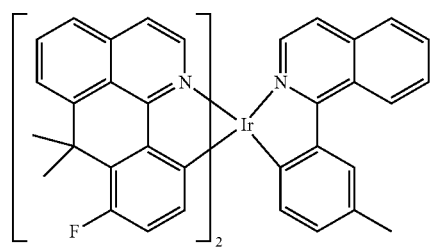
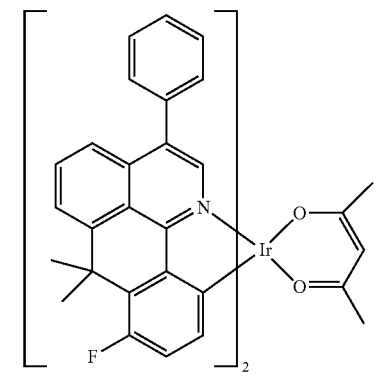
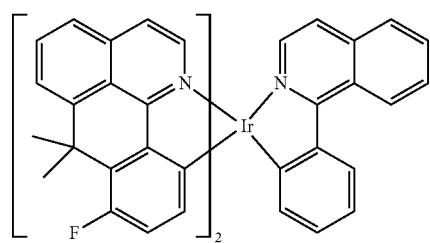

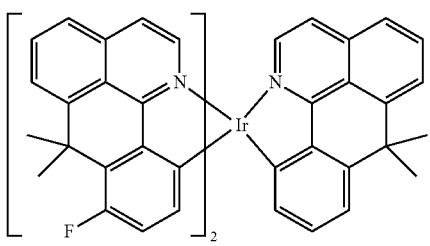
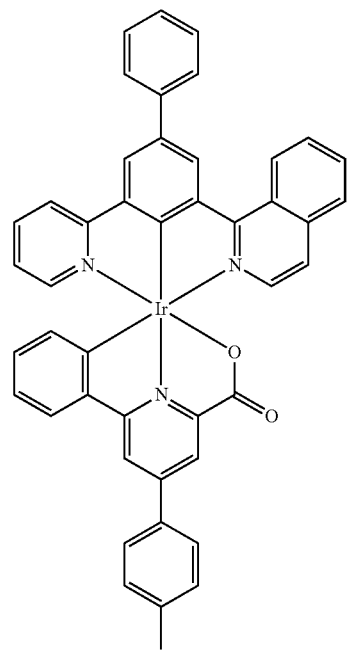
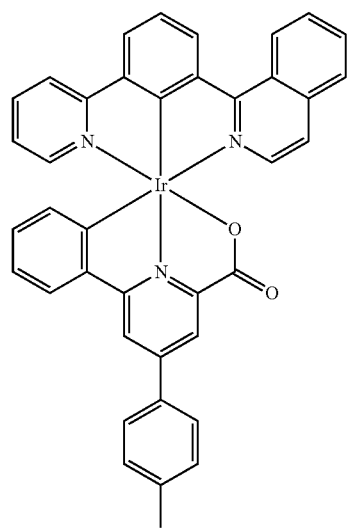
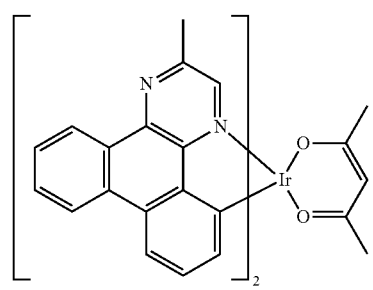
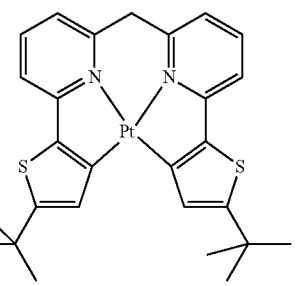
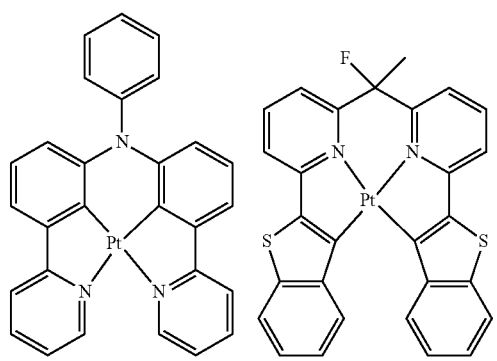
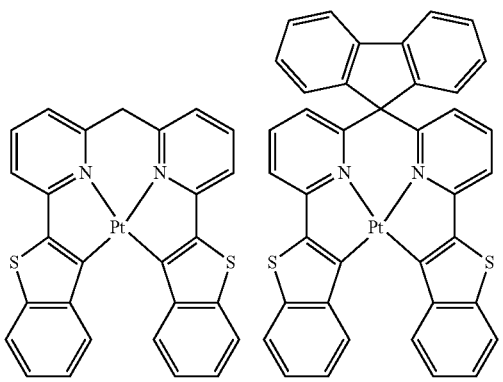

91
-continued
92
-continued
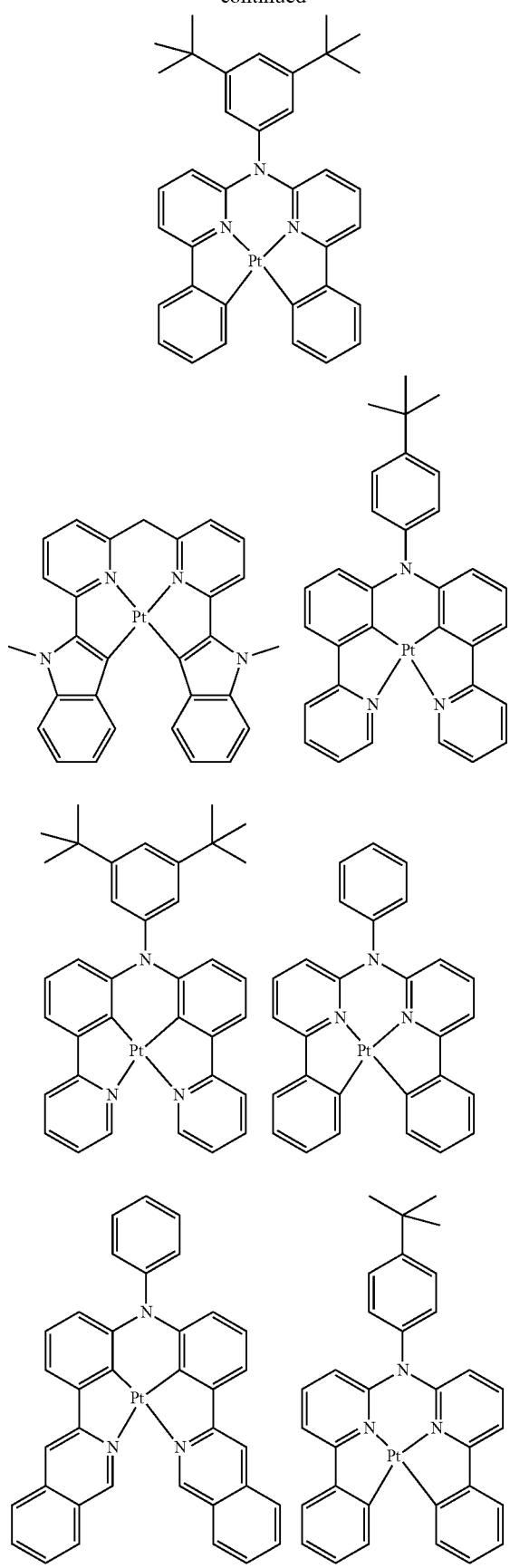
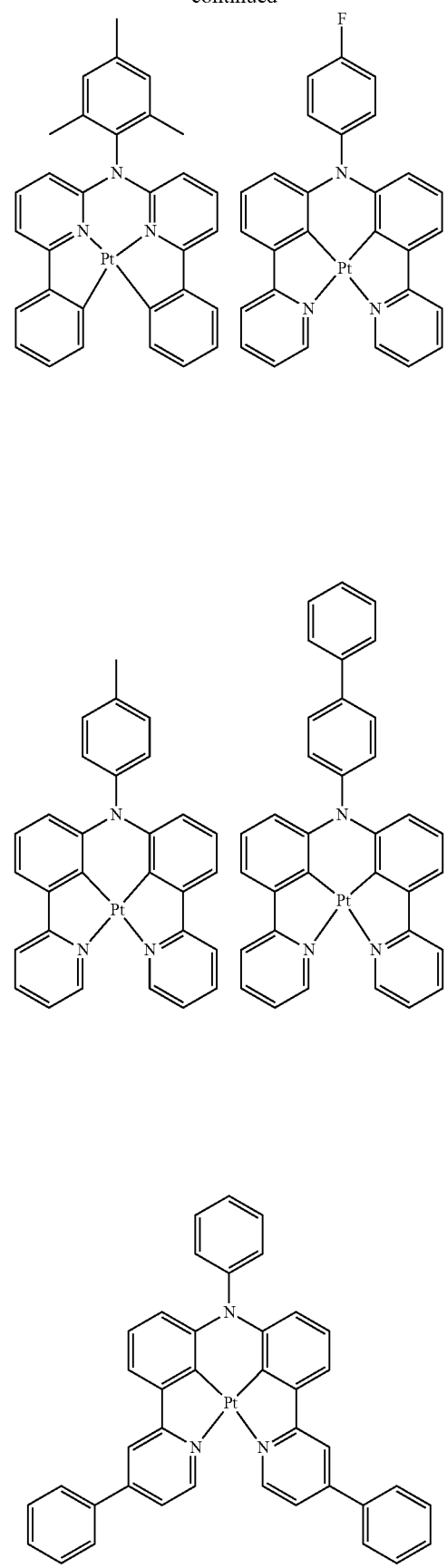

93
-continued
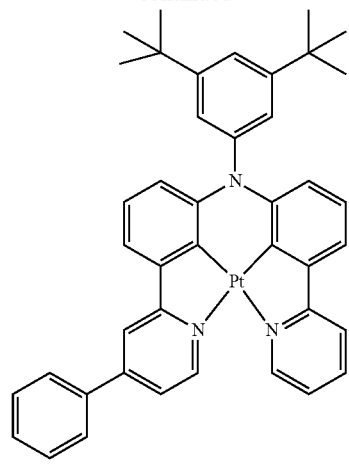
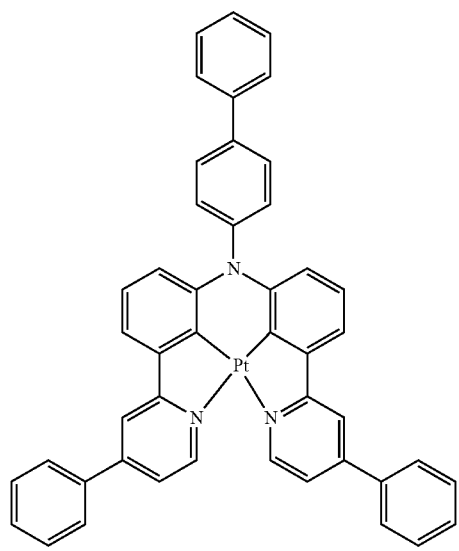
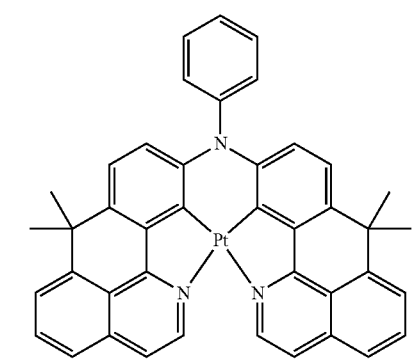
94
-continued
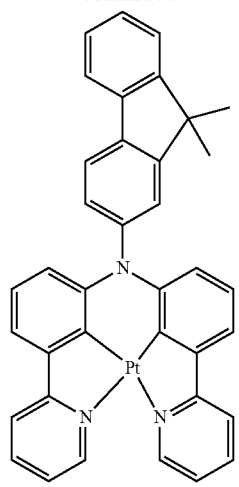
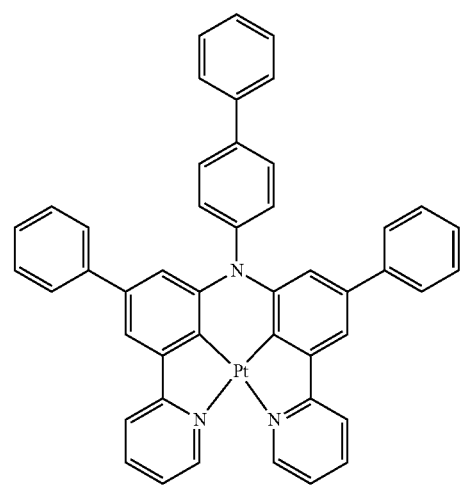
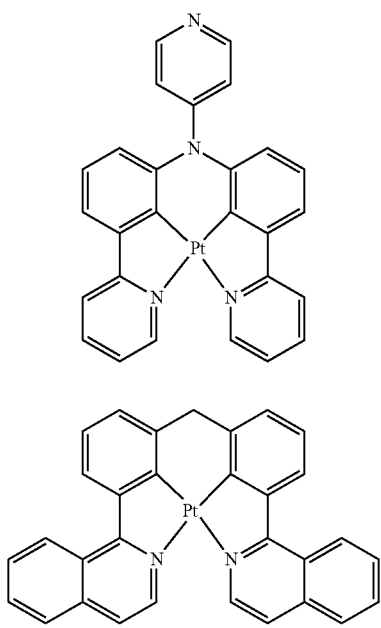

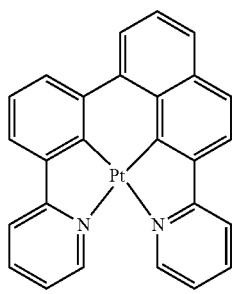
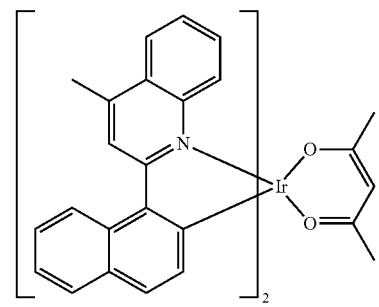
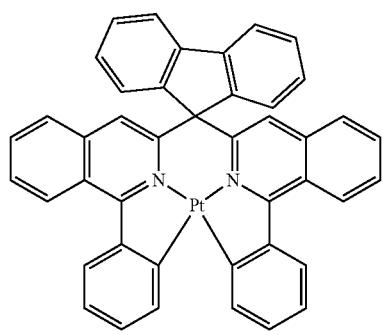
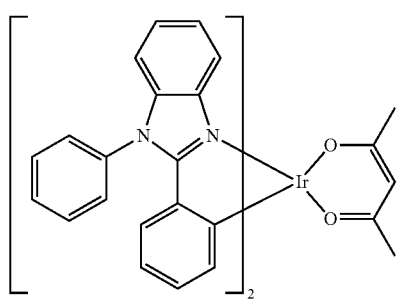
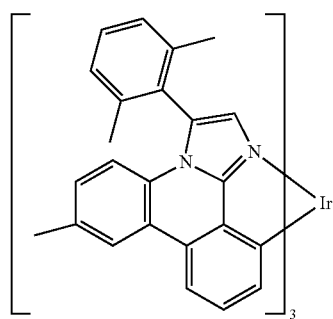
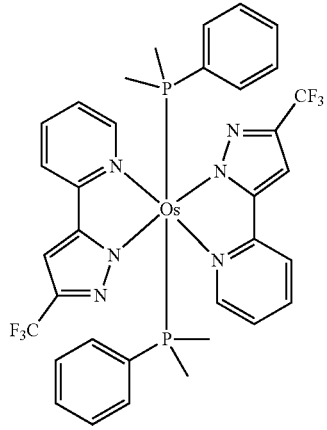
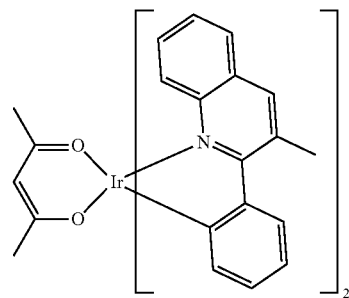
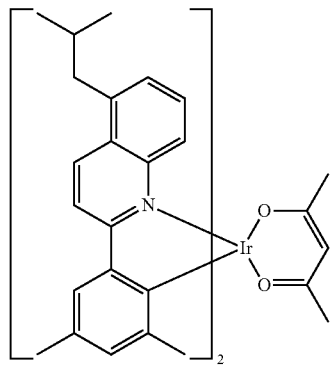
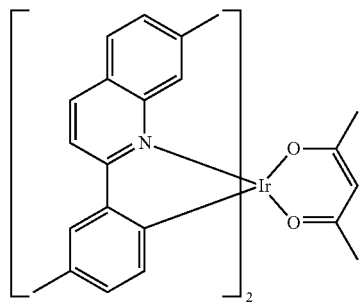
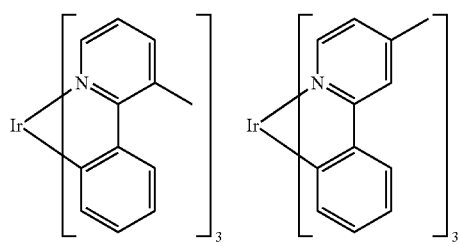

97
-continued
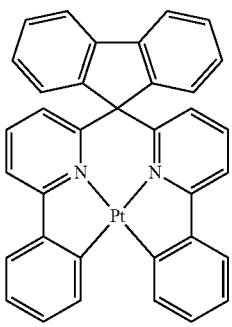
98
-continued
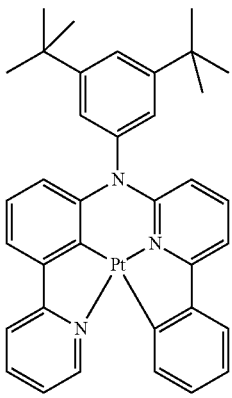
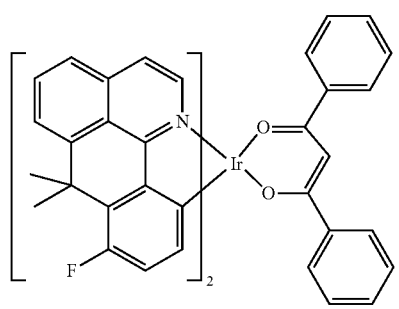
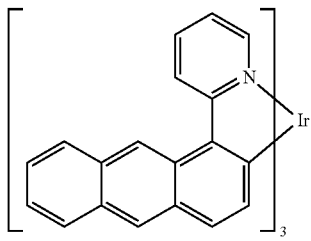
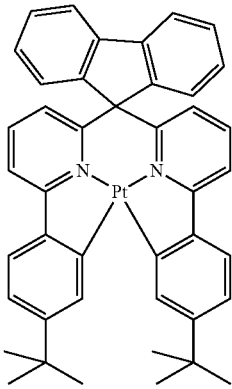
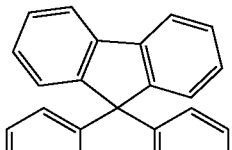
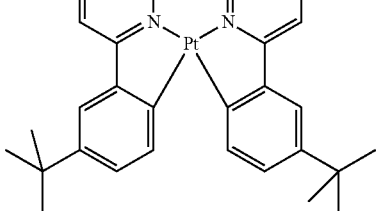

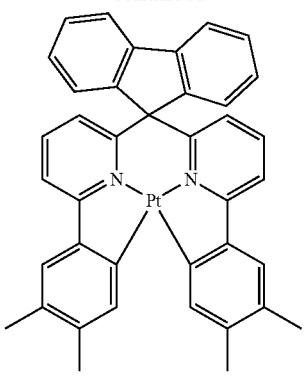
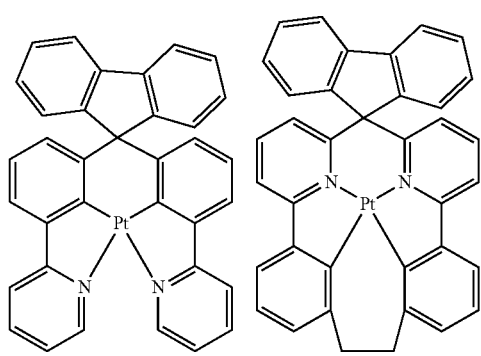
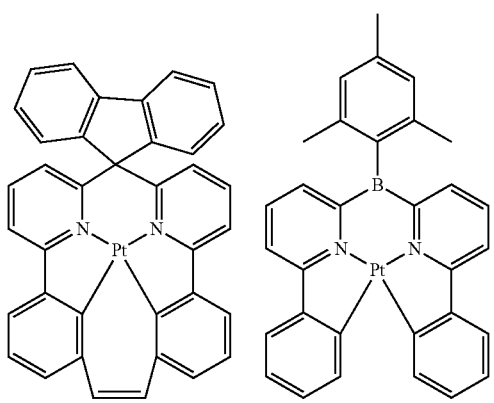
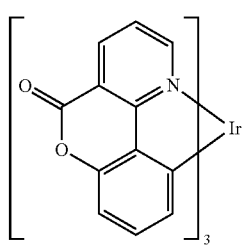
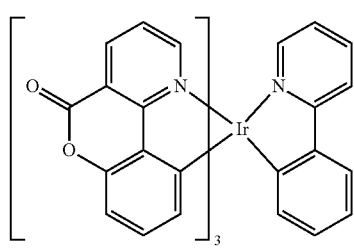
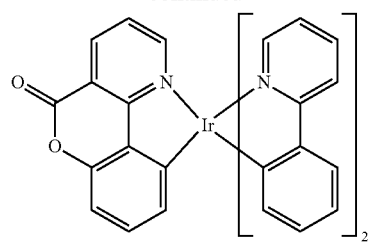
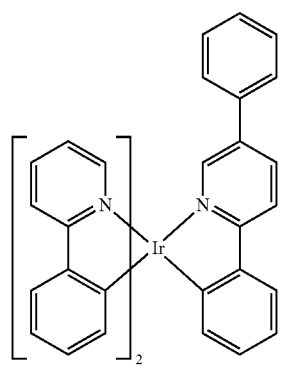
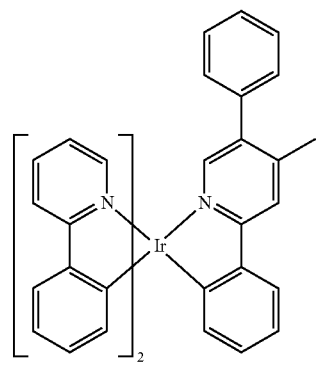
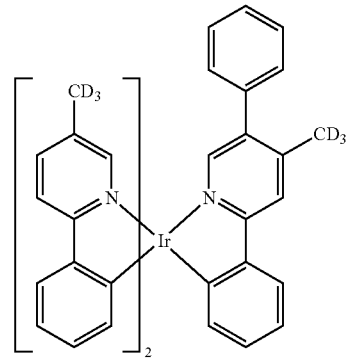
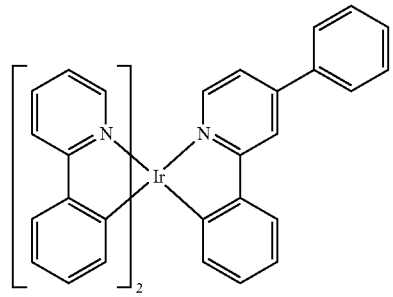

101
-continued
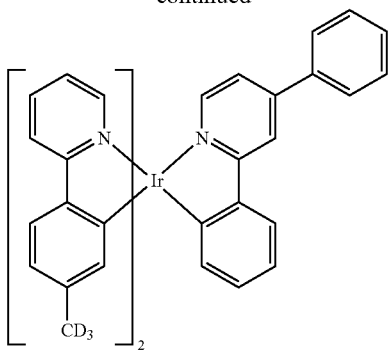
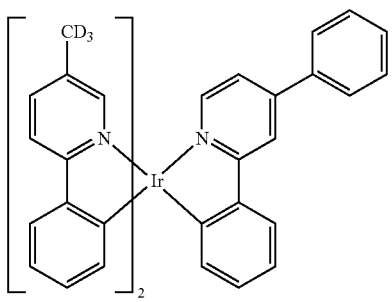
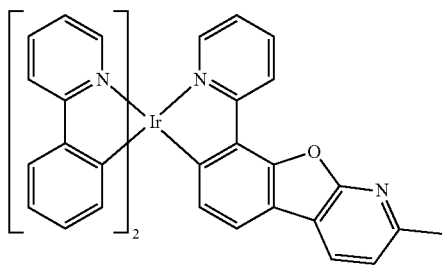
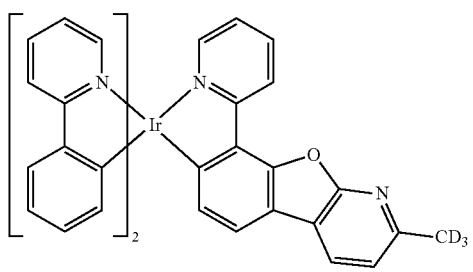
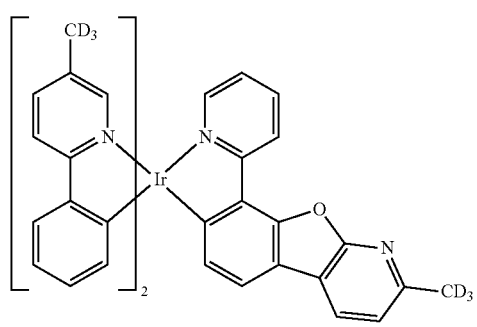
102
-continued
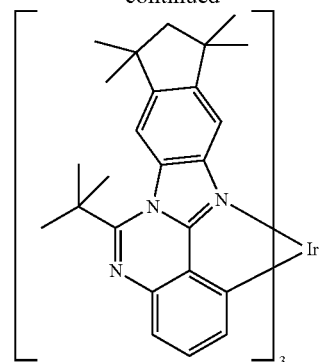
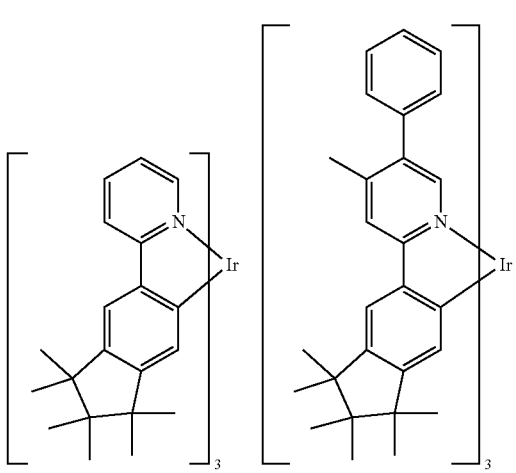
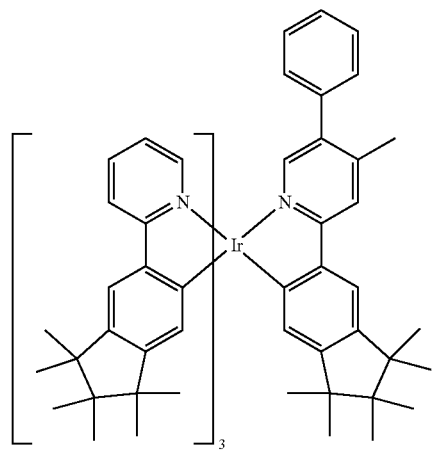
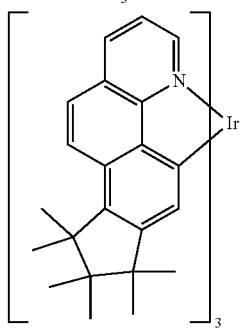

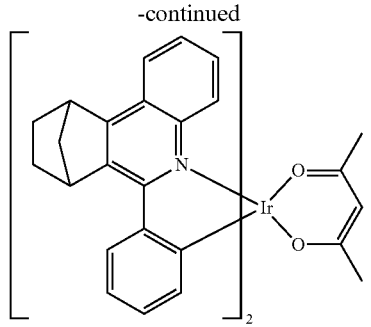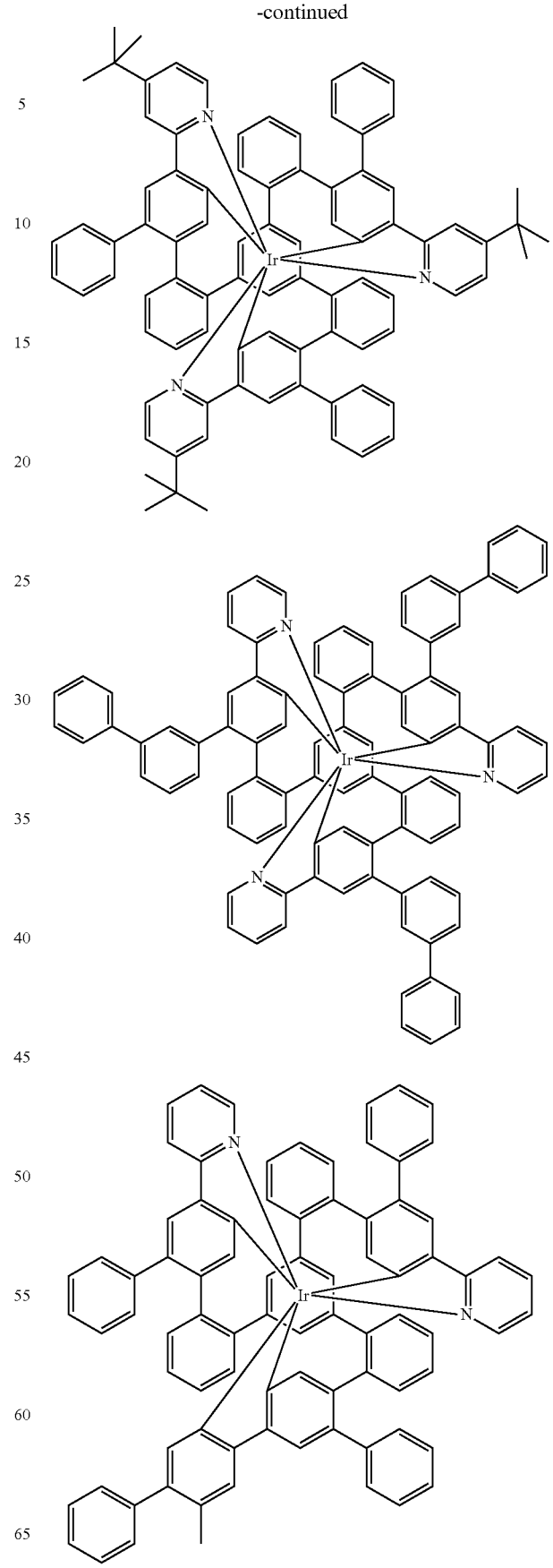

-continued

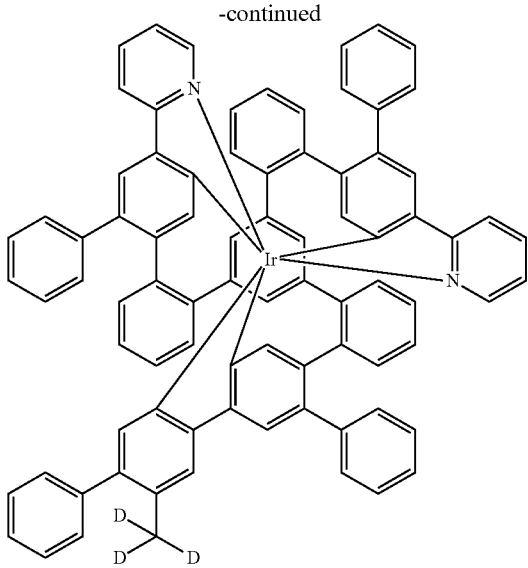

The compounds of the invention are especially also suitable as matrix materials for phosphorescent emitters in organic electroluminescent devices, as described, for example, in WO 98/24271, US 2011/0248247 and US 2012/0223633. In these multicolour display components, an additional blue emission layer is applied by vapour deposition over the full area to all pixels, including those having a colour other than blue. It has been found that, surprisingly, the compounds of the invention, when they are used as matrix materials for the red and/or green pixels, still lead to very good emission together with the blue emission layer applied by vapour deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapour deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:

1. The compounds of the invention, used as matrix material for phosphorescent emitters, lead to long lifetimes.
2. The compounds of the invention lead to high efficiencies. This is especially true when the compounds are used as matrix material for a phosphorescent emitter.
3. The compounds of the invention lead to low operating voltages. This is especially true when the compounds are used as matrix material for a phosphorescent emitter.

These abovementioned advantages are not accompanied by a deterioration in the further electronic properties.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere. The solvents and reagents can be purchased from ALDRICH or ABCR. The numbers given for the reactants known from the literature that are not commercially available are the corresponding CAS numbers.

107 a) 7-(9-Phenyl-9H-carbazol-3-yl)-10H-10,11-diazabenzo[b]fluorene

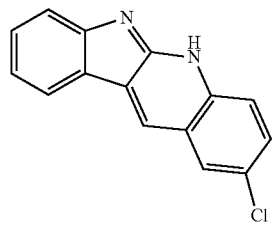

[450380-62-8]

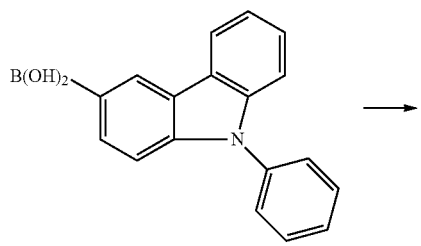

108

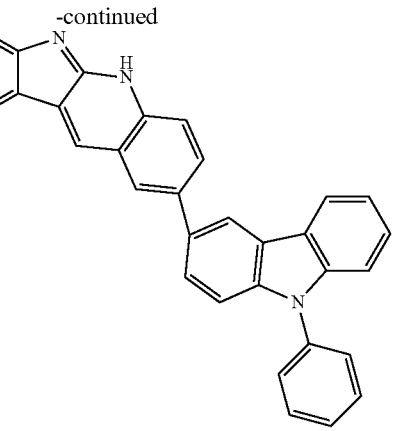

38.7 g (155 mmol) of 7-chloro-10H-10,11-diazabenzo[b]fluorene, 50 g (172 mmol) of N-phenylcarbazole-3-boronic acid and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness.

The following compounds can be prepared in an analogous manner:

| | Reactant 1 | Reactant 2 |
|---|---|---|
| 1a | 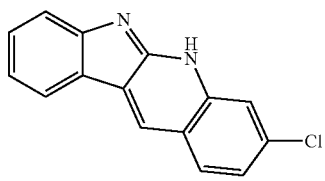<br>[1150313-11-3] | 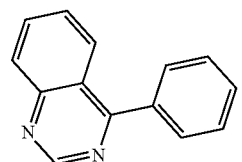<br>[1642121-58-1] |
| 2a | 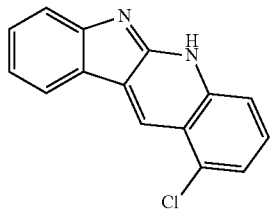<br>[1369774-03-7] | 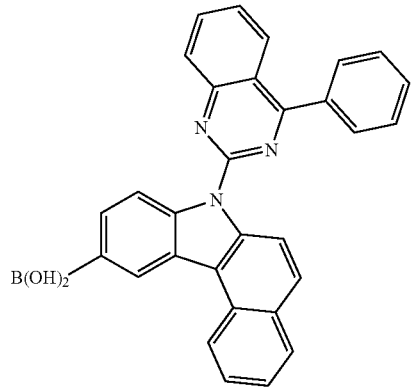<br>[1365548-86-2] |

-continued
| | | | |
|---|---|---|---|
| 3a | 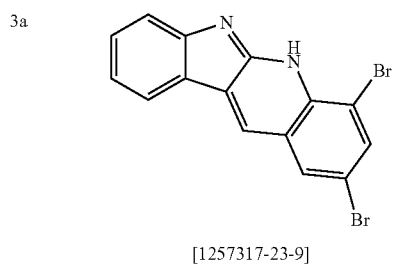 [1257317-23-9] | | 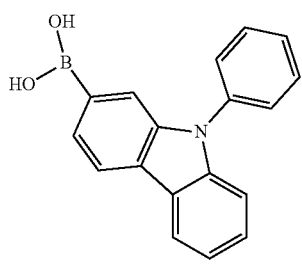 [1001911-63-2] |
| 4a | 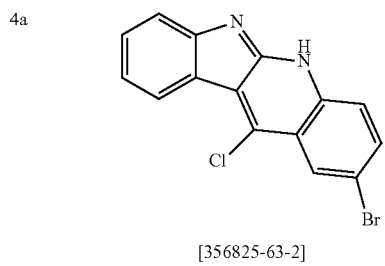 [356825-63-2] | | 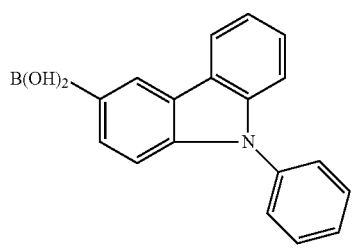 [SMILES: OB(O)c1ccc2c(c1)c1ccccc1n2-c1ccccc1] |
| 5a | 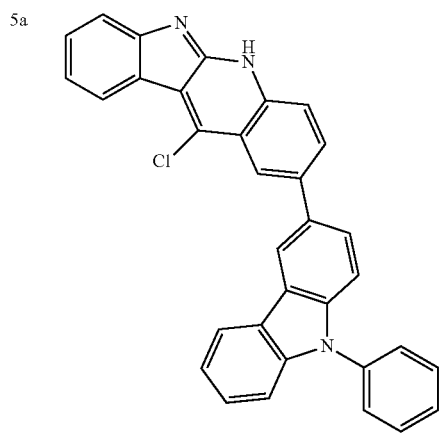 | | 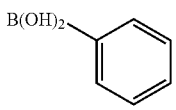 |
| 6a | 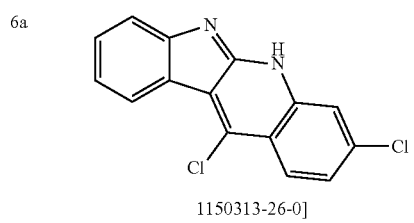 1150313-26-0] | | 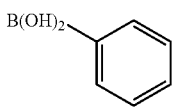 |
| 7a | 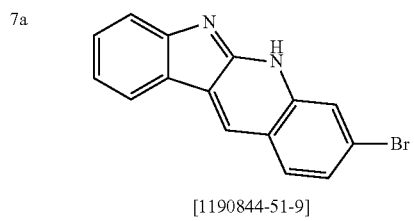 [1190844-51-9] | | 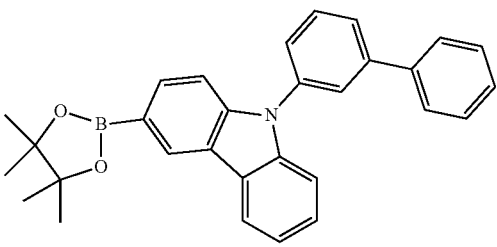 [1416814-68-0] |

| | | | |
|---|---|---|---|
| 8a | 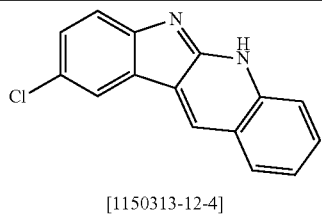<br>[1150313-12-4] | 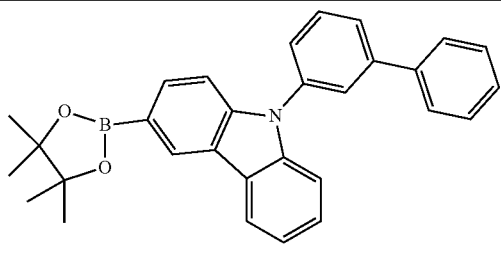<br>[1416814-68-0] | |
| 9a | 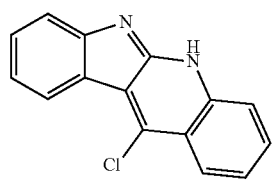<br>[108832-19-5] | 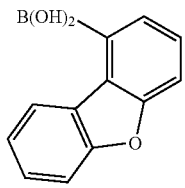 | |
| 10a | 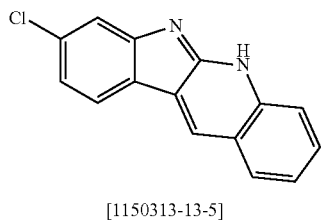 [SMILES: Clc1ccc2c3cc4ccccc4[nH]c-3nc2c1]<br>[1150313-13-5] | 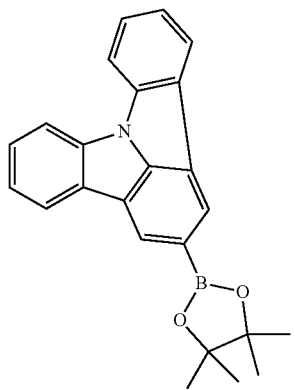<br>[1369369-44-7] | |
| 11a | 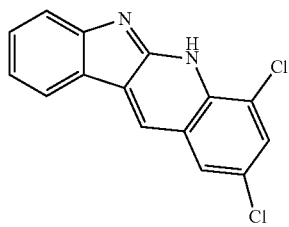<br>[450380-64-0] | 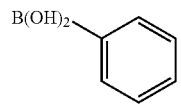 | |

| | |
|---|---|
| 12a 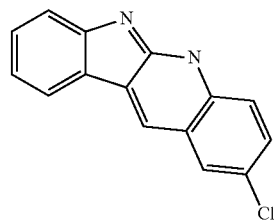 [450380-62-8] | 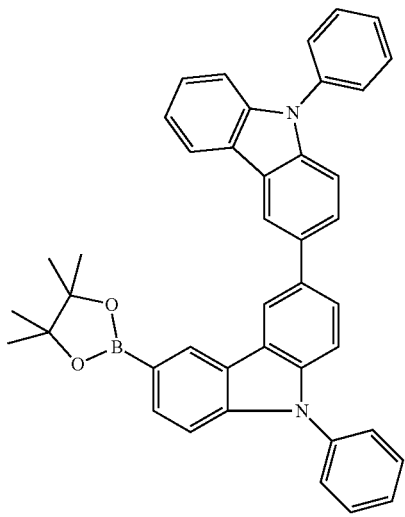 [1572537-61-1] |
| Product | |
| 1a 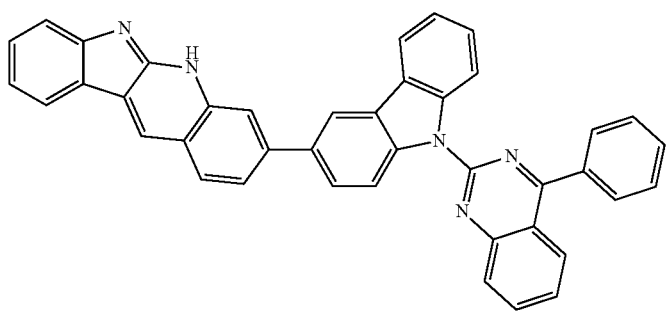 [SMILES: c1ccc(-c2nc(-n3c4ccccc4c4cc(-c5ccc6cc7c8ccccc8nc-7[nH]c6c5)ccc43)nc3ccccc23)cc1] | |
| 2a 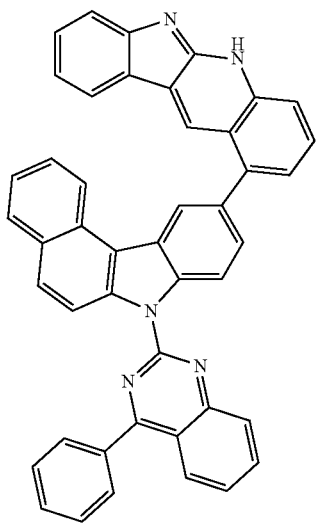 [SMILES: c1ccc(-c2nc(-n3c4ccc(-c5cccc6[nH]c7nc8ccccc8c-7cc56)cc4c4c5ccccc5ccc43)nc3ccccc23)cc1] | |

-continued
3a
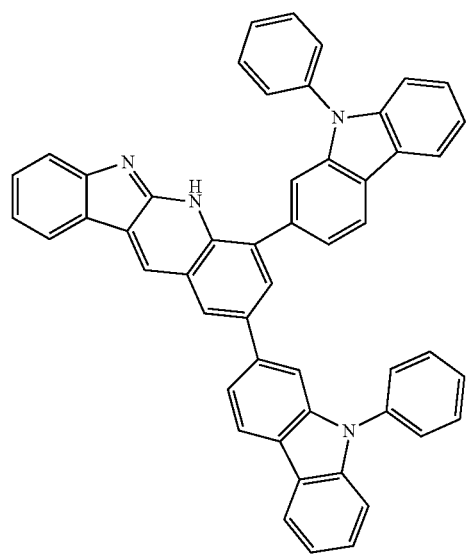 [SMILES: c1ccc(-n2c3ccccc3c3ccc(-c4cc(-c5ccc6c7ccccc7n(-c7ccccc7)c6c5)c5[nH]c6nc7ccccc7c-6cc5c4)cc32)cc1]
4a
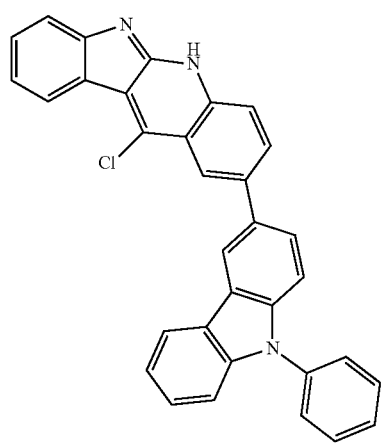 [SMILES: Clc1c2c3ccccc3nc-2[nH]c2ccc(-c3ccc4c(c3)c3ccccc3n4-c3ccccc3)cc12]
5a
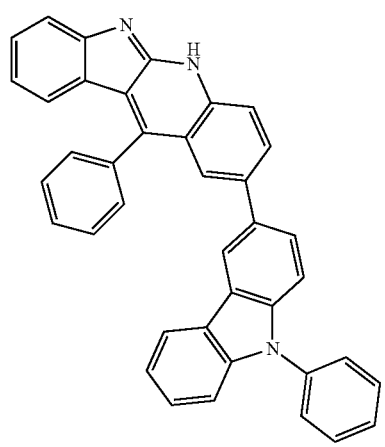 [SMILES: c1ccc(-c2c3c4ccccc4nc-3[nH]c3ccc(-c4ccc5c(c4)c4ccccc4n5-c4ccccc4)cc23)cc1]

-continued
6a 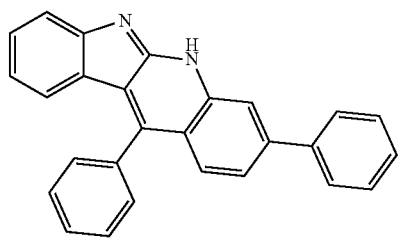 [SMILES: c1ccc(-c2ccc3c(-c4ccccc4)c4c5ccccc5nc-4[nH]c3c2)cc1]
7a 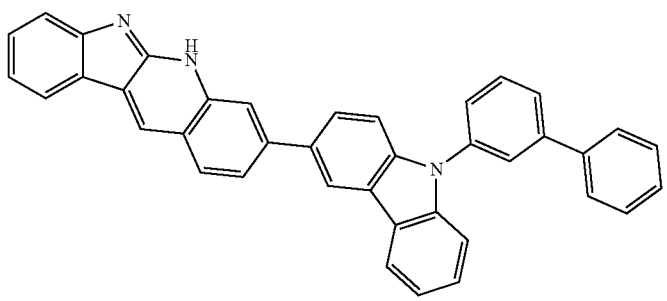 [SMILES: c1ccc(-c2cccc(-n3c4ccccc4c4cc(-c5ccc6cc7c8ccccc8nc-7[nH]c6c5)ccc43)c2)cc1]
8a 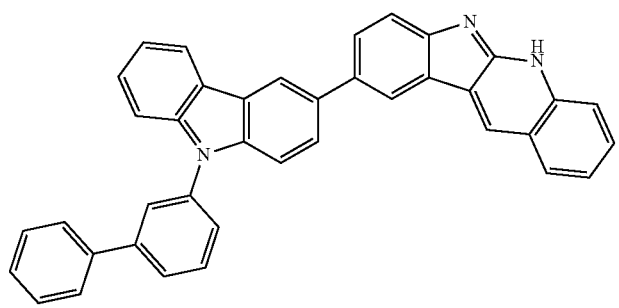
9a 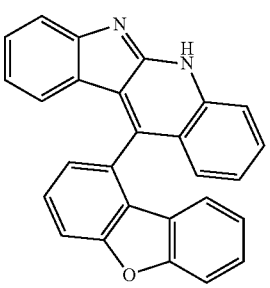 [SMILES: c1ccc2c3c(-c4cccc5oc6ccccc6c45)c4ccccc4[nH]c-3nc2c1]
10a 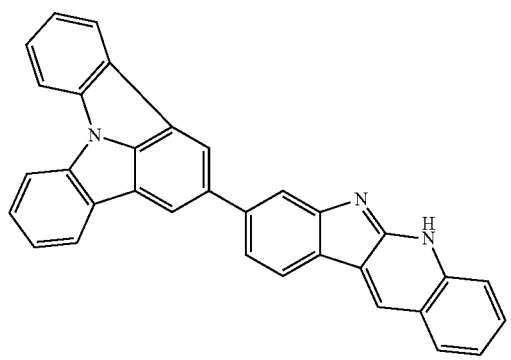 [SMILES: c1ccc2[nH]c3nc4cc(-c5cc6c7ccccc7n7c8ccccc8c(c5)c67)ccc4c-3cc2c1]

| | |
|---|---|
| 11a | 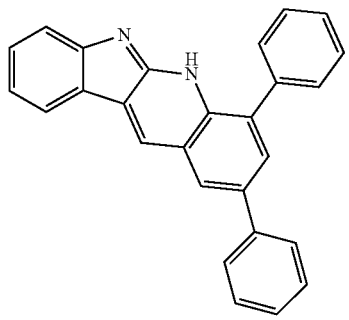 [SMILES: c1ccc(-c2cc(-c3ccccc3)c3[nH]c4nc5ccccc5c-4cc3c2)cc1] |
| 12a | 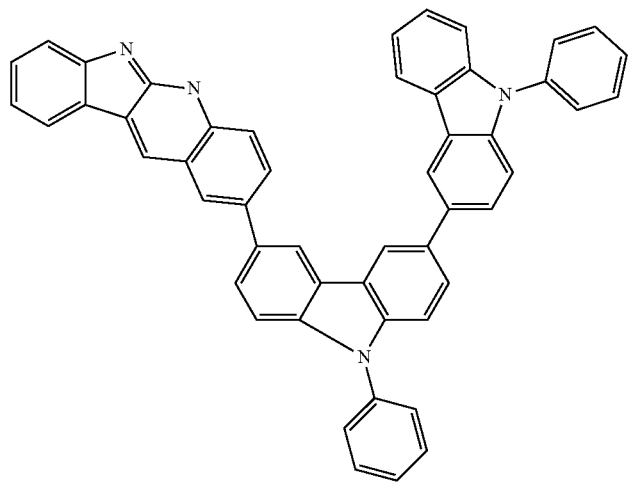 [SMILES: c1ccc(-n2c3ccccc3c3cc(-c4ccc5c(c4)c4cc(-c6ccc7[nH]c8nc9ccccc9c-8cc7c6)ccc4n5-c4ccccc4)ccc32)cc1] | b) 10-[9-(9-Phenyl-9H-carbazol-3-yl)dibenzofuran-2-yl]-10H-10,11-diazabenzo[b]fluorene

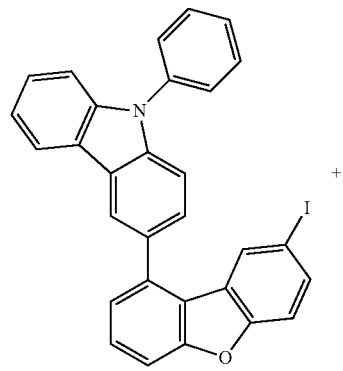

[1363317-50-3]

+

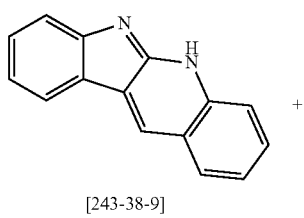

[243-38-9]

+

-continued

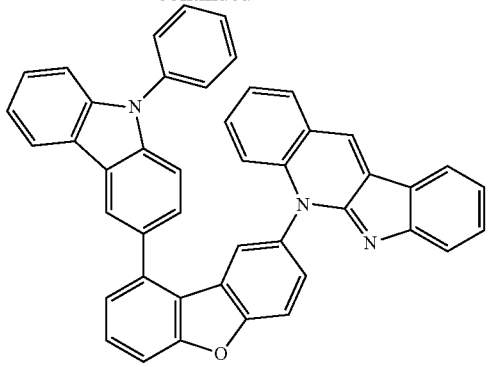

A degassed solution of 78 g (147 mmol) of 3-(8-iodo-1-dibenzofuranyl)-9-phenyl-9H-carbazole and 32 g (147 mmol) of 10H-10,11-diazabenzo[b]fluorene in 600 ml of toluene is saturated with $N_2$ for 1 h. Added to the solution thereafter are first 2.09 ml (8.6 mmol) of $P(tBu)_3$ and then 1.38 g (6.1 mmol) of palladium(II) acetate. This is followed by addition of 17.7 g (185 mmol) of NaOtBu in the solid state. The reaction mixture is heated under reflux for 1 h. After cooling to room temperature, 500 ml of water are added cautiously The aqueous phase is washed with 3×50 ml of toluene, dried over $M_gSO_4$, and the solvent is removed under reduced pressure. Thereafter, the crude product is purified by chromatography using silica gel with heptane/ethyl acetate (20:2). The residue is recrystallized from toluene and finally sublimed under high vacuum (p=5×10$^{-6}$ mbar).

The following compounds can be prepared in an analogous manner:
| | Reactant 1 | Reactant 2 |
|---|---|---|
| 1b | 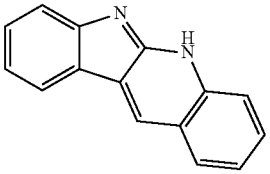 [243-38-9] | 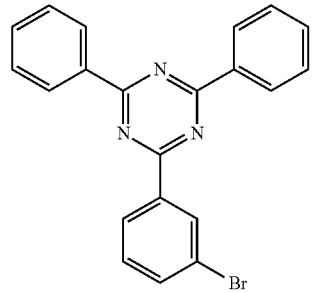 [864377-31-1] |
| 2b | 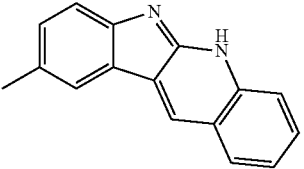 [52533-17-2] | 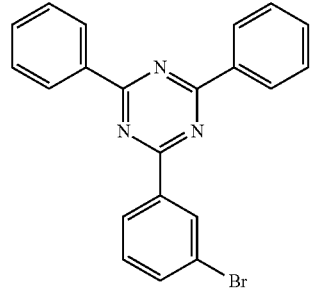 [864377-31-1] |
| 3b | 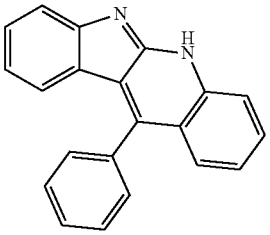 [19069-76-2] | 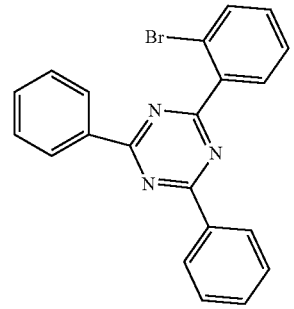 [77989-15-2] |
| 4b | 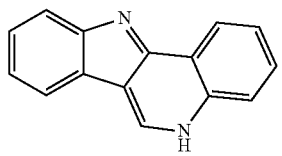 [239-08-7] | 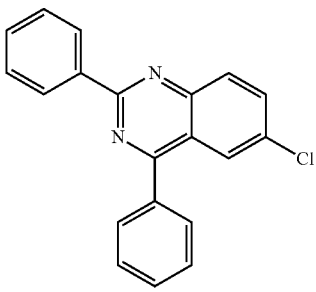 [30169-34-7] |

| | | | |
|---|---|---|---|
| 5b | 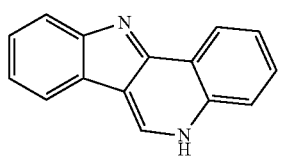
[239-08-7] | | 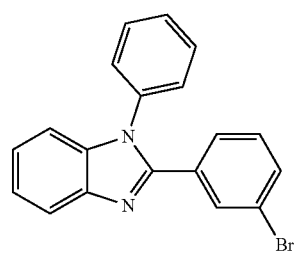
[760212-40-6] |
| 6b | 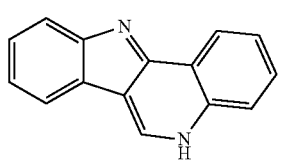
[239-08-7] | | 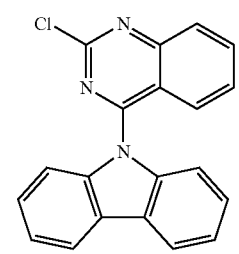
[1262866-84-1] |
| 7b | 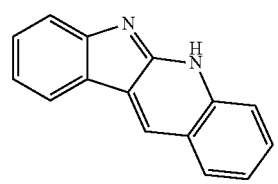
[243-38-9] | | 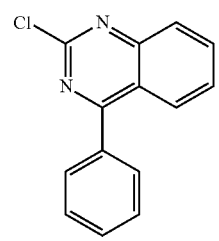
[29874-83-7] |
| 8b | 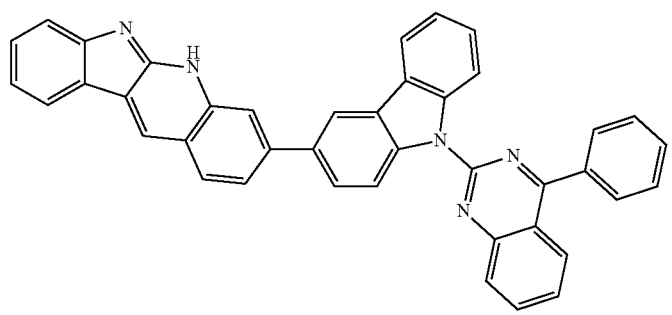 [SMILES: c1ccc(-c2nc(-n3c4ccccc4c4cc(-c5ccc6cc7c8ccccc8nc-7[nH]c6c5)ccc43)nc3ccccc23)cc1] | | 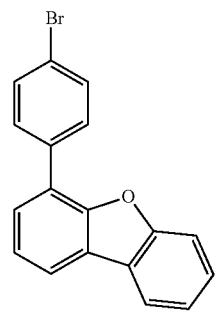
[1225053-54-2] |

9b 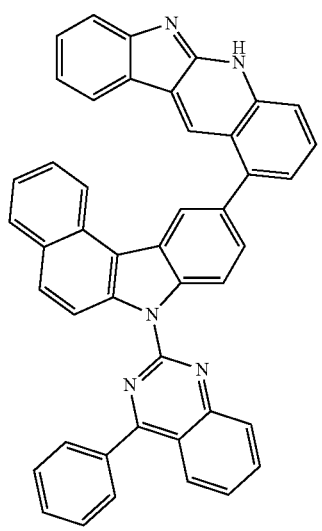 [SMILES: c1ccc(-c2nc(-n3c4ccc(-c5cccc6[nH]c7nc8ccccc8c-7cc56)cc4c4c5ccccc5ccc43)nc3ccccc23)cc1] 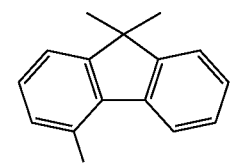
[942615-32-9]
10b 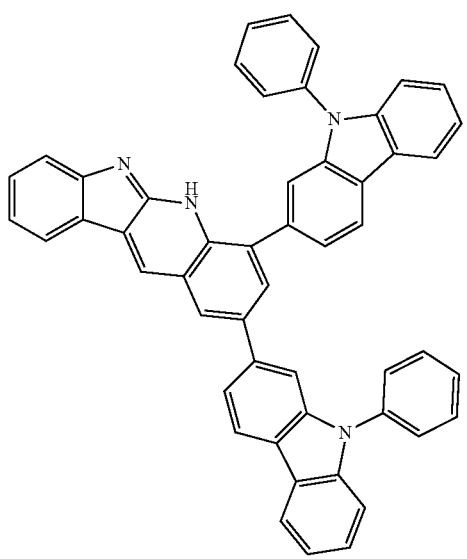 [SMILES: c1ccc(-n2c3ccccc3c3ccc(-c4cc(-c5ccc6c7ccccc7n(-c7ccccc7)c6c5)c5[nH]c6nc7ccccc7c-6cc5c4)cc32)cc1] 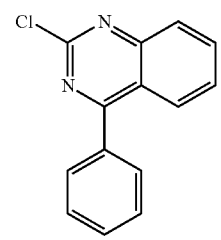
[29874-83-7]
11b 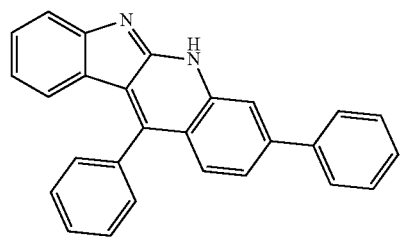 [SMILES: c1ccc(-c2ccc3c(-c4ccccc4)c4c5ccccc5nc-4[nH]c3c2)cc1] 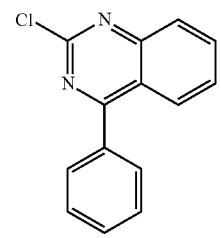
[29874-83-7]

-continued
| | | | |
|---|---|---|---|
| 12b | 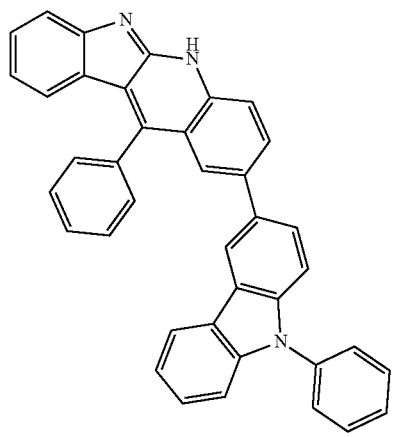 [SMILES: c1ccc(-c2c3c4ccccc4nc-3[nH]c3ccc(-c4ccc5c(c4)c4ccccc4n5-c4ccccc4)cc23)cc1] | 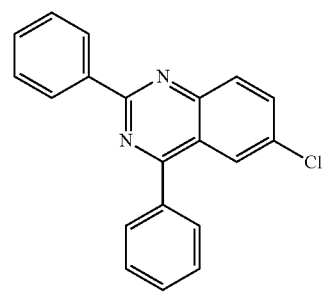
[30169-34-7] | |
| 13b | 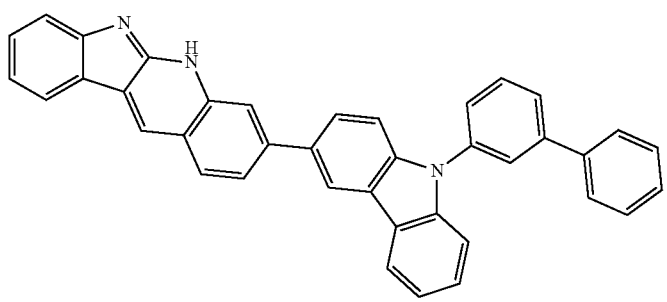 [SMILES: c1ccc(-c2cccc(-n3c4ccccc4c4cc(-c5ccc6cc7c8ccccc8nc-7[nH]c6c5)ccc43)c2)cc1] | 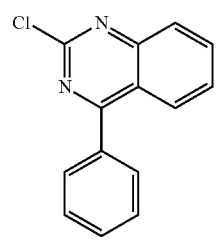
[29874-83-7] | |
| 14b | 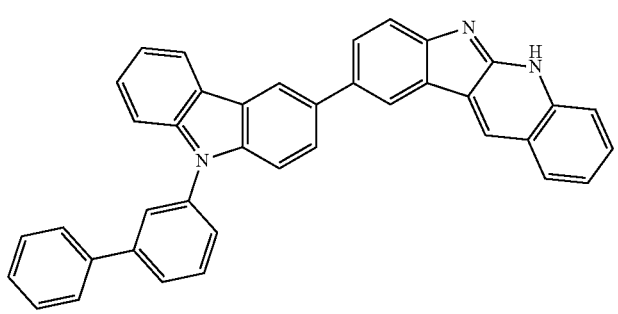 | 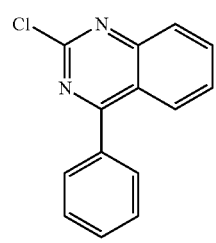
[29874-83-7] | |
| 15b | 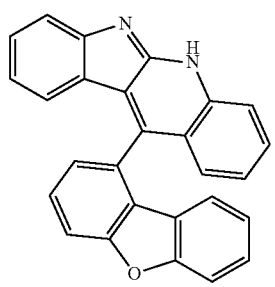 [SMILES: c1ccc2c3c(-c4cccc5oc6ccccc6c45)c4ccccc4[nH]c-3nc2c1] | 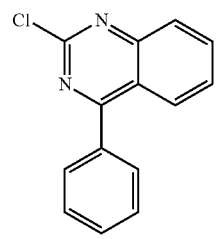
[29874-83-7] | |

-continued
16b 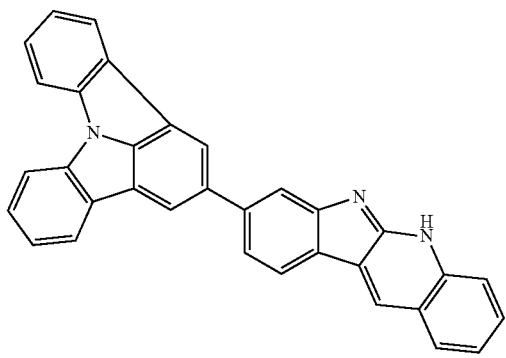 [SMILES: c1ccc2[nH]c3nc4cc(-c5cc6c7ccccc7n7c8ccccc8c(c5)c67)ccc4c-3cc2c1]
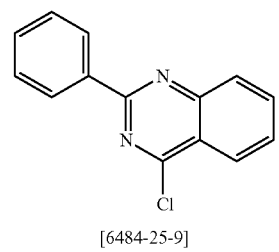 [SMILES: Clc1nc(-c2ccccc2)nc2ccccc12]
[6484-25-9]
17b 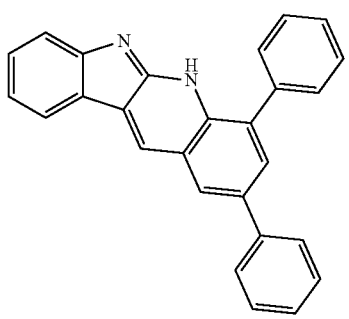 [SMILES: c1ccc(-c2cc(-c3ccccc3)c3[nH]c4nc5ccccc5c-4cc3c2)cc1]
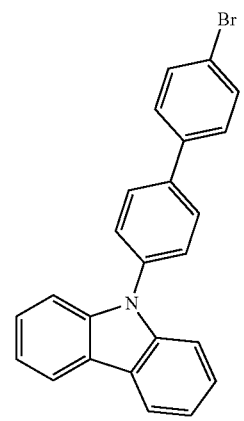
[212385-73-4]
18b 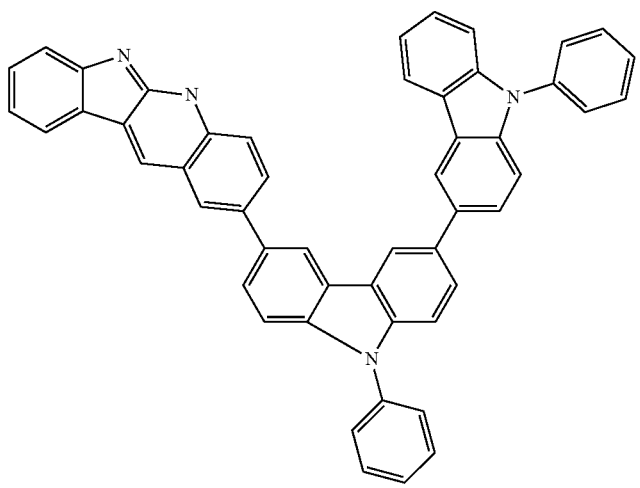 [SMILES: c1ccc(-n2c3ccccc3c3cc(-c4ccc5c(c4)c4cc(-c6ccc7[nH]c8nc9ccccc9c-8cc7c6)ccc4n5-c4ccccc4)ccc32)cc1]
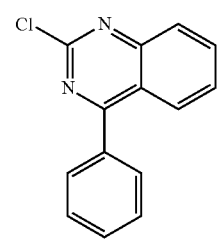
[29874-83-7]

-continued
| | Product |
|---|---|
| 1b | 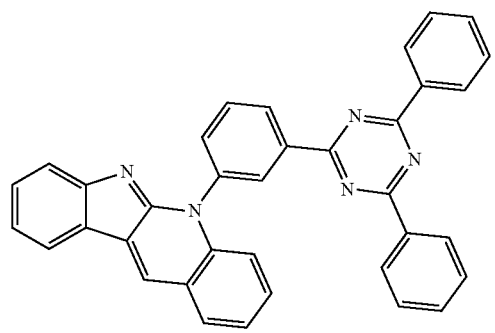 [SMILES: c1ccc(-c2nc(-c3ccccc3)nc(-c3cccc(-n4c5nc6ccccc6c-5cc5ccccc54)c3)n2)cc1] |
| 2b | 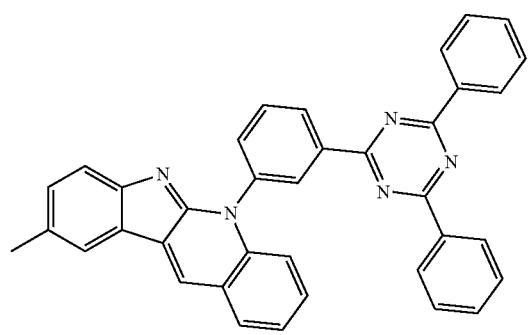 [SMILES: Cc1ccc2nc3n(-c4cccc(-c5nc(-c6ccccc6)nc(-c6ccccc6)n5)c4)c4ccccc4cc-3c2c1] |
| 3b | 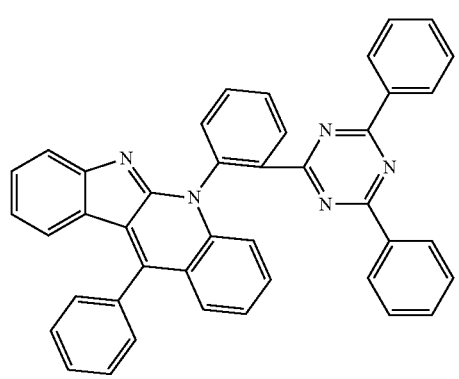 |
| | [19069-76-2] |
| 4b | 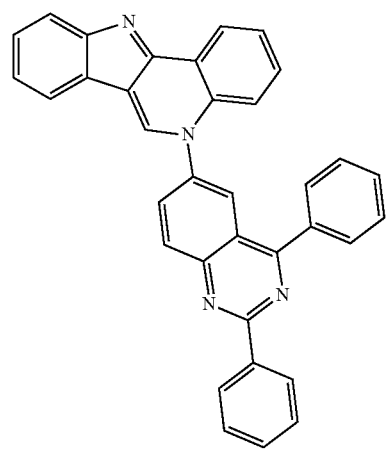 [SMILES: c1ccc(-c2nc(-c3ccccc3)c3cc(-n4cc5c6ccccc6nc-5c5ccccc54)ccc3n2)cc1] |

-continued
5b 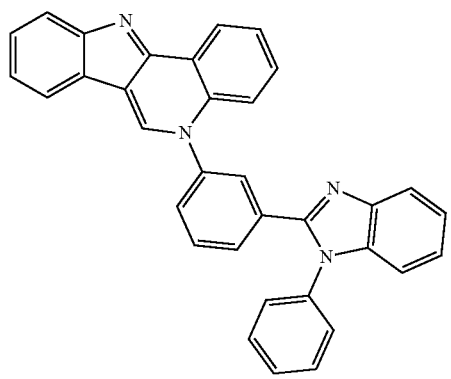 [SMILES: c1ccc(-n2c(-c3cccc(-n4cc5c6ccccc6nc-5c5ccccc54)c3)nc3ccccc32)cc1]
6b 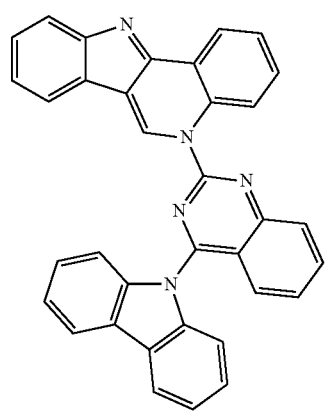 [SMILES: c1ccc2c3cn(-c4nc(-n5c6ccccc6c6ccccc65)c5ccccc5n4)c4ccccc4c-3nc2c1]
7b 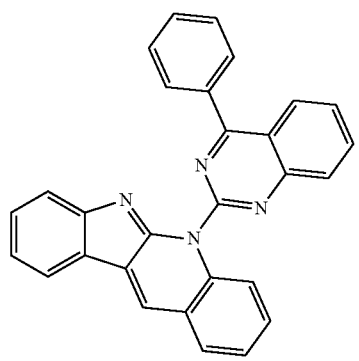 [SMILES: c1ccc(-c2nc(-n3c4nc5ccccc5c-4cc4ccccc43)nc3ccccc23)cc1]

-continued
8b
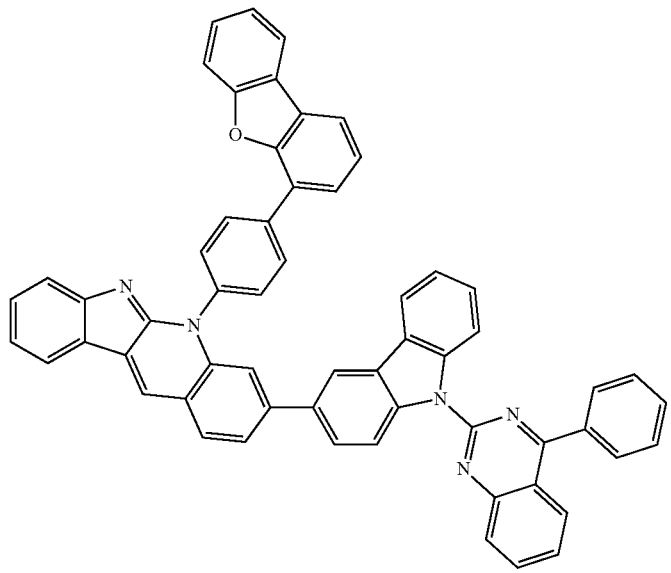 [SMILES: c1ccc(-c2nc(-n3c4ccccc4c4cc(-c5ccc6cc7c8ccccc8nc-7n(-c7ccc(-c8cccc9c8oc8ccccc89)cc7)c6c5)ccc43)nc3ccccc23)cc1]
9b
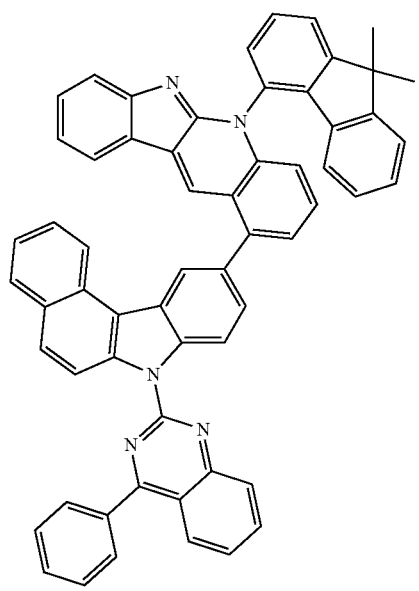 [SMILES: CC1(C)c2ccccc2-c2c(-n3c4nc5ccccc5c-4cc4c(-c5ccc6c(c5)c5c7ccccc7ccc5n6-c5nc(-c6ccccc6)c6ccccc6n5)cccc43)cccc21]

10b
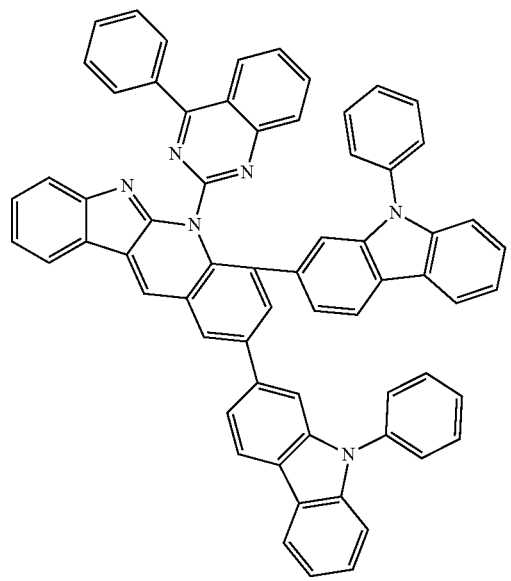 [SMILES: c1ccc(-c2nc(-n3c4nc5ccccc5c-4cc4cc(-c5ccc6c7ccccc7n(-c7ccccc7)c6c5)cc(-c5ccc6c7ccccc7n(-c7ccccc7)c6c5)c43)nc3ccccc23)cc1]
11b
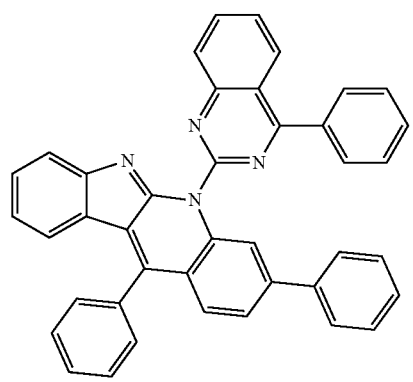 [SMILES: c1ccc(-c2ccc3c(-c4ccccc4)c4c5ccccc5nc-4n(-c4nc(-c5ccccc5)c5ccccc5n4)c3c2)cc1]
12b
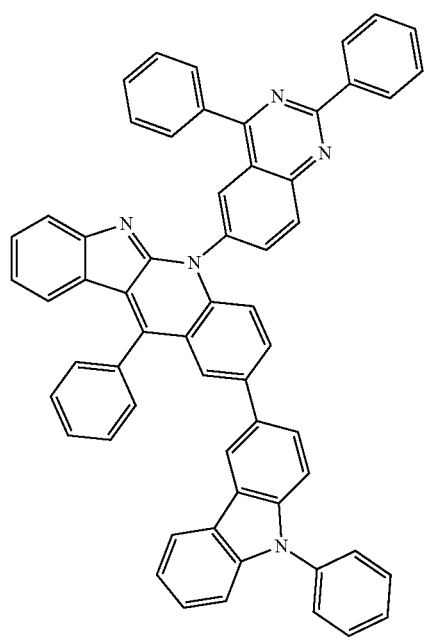 [SMILES: c1ccc(-c2nc(-c3ccccc3)c3cc(-n4c5nc6ccccc6c-5c(-c5ccccc5)c5cc(-c6ccc7c(c6)c6ccccc6n7-c6ccccc6)ccc54)ccc3n2)cc1]

13b
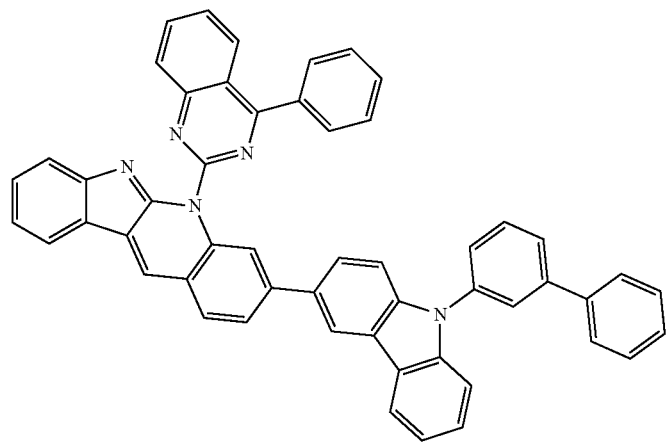 [SMILES: c1ccc(-c2cccc(-n3c4ccccc4c4cc(-c5ccc6cc7c8ccccc8nc-7n(-c7nc(-c8ccccc8)c8ccccc8n7)c6c5)ccc43)c2)cc1]
14b
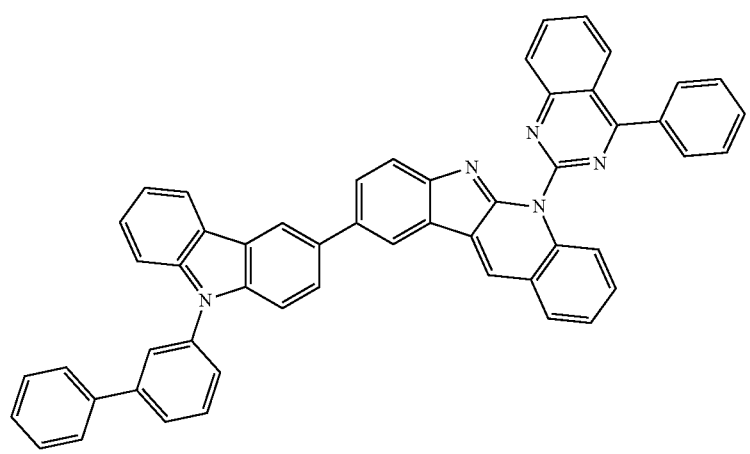
15b
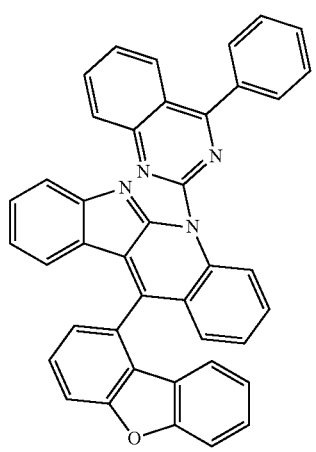 [SMILES: c1ccc(-c2nc(-n3c4nc5ccccc5c-4c(-c4cccc5oc6ccccc6c45)c4ccccc43)nc3ccccc23)cc1]

-continued
16b
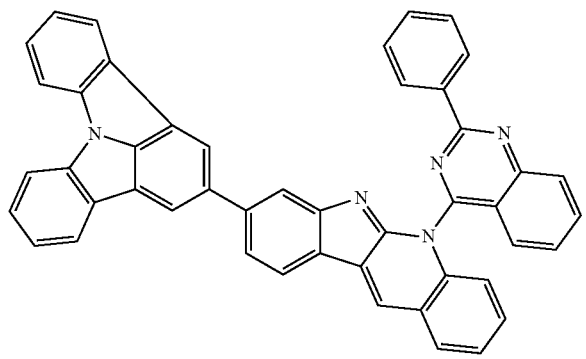 [SMILES: c1ccc(-c2nc(-n3c4nc5cc(-c6cc7c8ccccc8n8c9ccccc9c(c6)c78)ccc5c-4cc4ccccc43)c3ccccc3n2)cc1]
17b
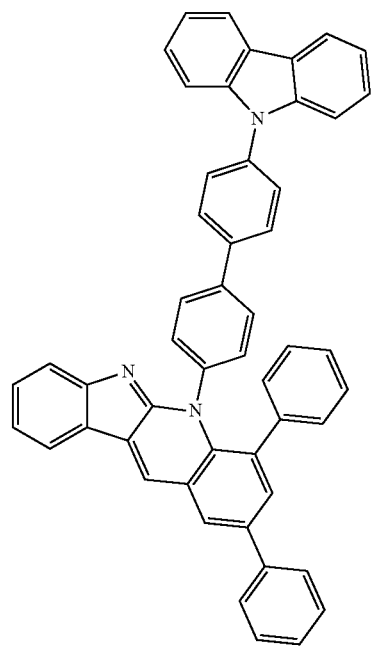 [SMILES: c1ccc(-c2cc(-c3ccccc3)c3c(c2)cc2c4ccccc4nc-2n3-c2ccc(-c3ccc(-n4c5ccccc5c5ccccc54)cc3)cc2)cc1]
18b
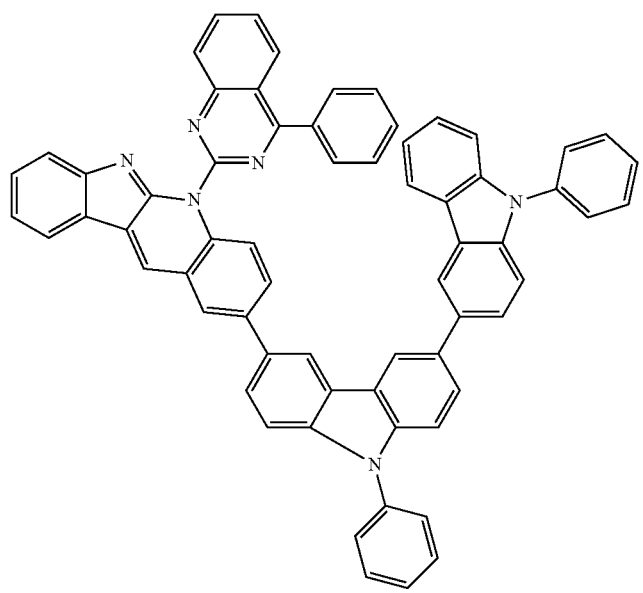 [SMILES: c1ccc(-c2nc(-n3c4nc5ccccc5c-4cc4cc(-c5ccc6c(c5)c5cc(-c7ccc8c(c7)c7ccccc7n8-c7ccccc7)ccc5n6-c5ccccc5)ccc43)nc3ccccc23)cc1]

Production of the OLEDs

Examples I1 to I6 which follow (see Table 1) present the use of the materials of the invention in OLEDs.

Pretreatment for Examples I1-I6:

Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blacker layer (EBL)/emission layer (EML)/ optional hole blacker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 2.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC2:EG1:TER (55%:35%:10%) mean here that the material IC2 is present in the layer in a proportion by volume of 55%, EG1 in a proportion by volume of 35% and TER in a proportion by volume of 10%. Analogously, the electron transport layer may also consist of a mixture of two materials.

The OLEDs are characterized in a standard manner. The electroluminescence spectra are determined at a luminance of 1000 cd/m$^2$, and the CIE 1931 x and y colour coordinates are calculated therefrom.

Use of Mixtures of the Invention in OLEDs

The materials of the invention can be used in the emission layer in phosphorescent red OLEDs. The inventive compounds EG1 to EG5 are used in Examples 11 to 16 as matrix material in the emission layer. The colour coordinates of the electroluminescence spectra of the OLEDs from these experiments are CIEx=0.67 and CIEy=0.33. The materials are thus suitable for use in the emission layer of red OLEDs.

In addition, the materials of the invention can be used successfully in the hole blacker layer (HBL). This is shown in Example 16. Here too, the colour coordinates of the spectrum of the OLED are CIEx=0.67 and CIEy=0.33.

TABLE 2

Structural formulae of the materials for the OLEDs

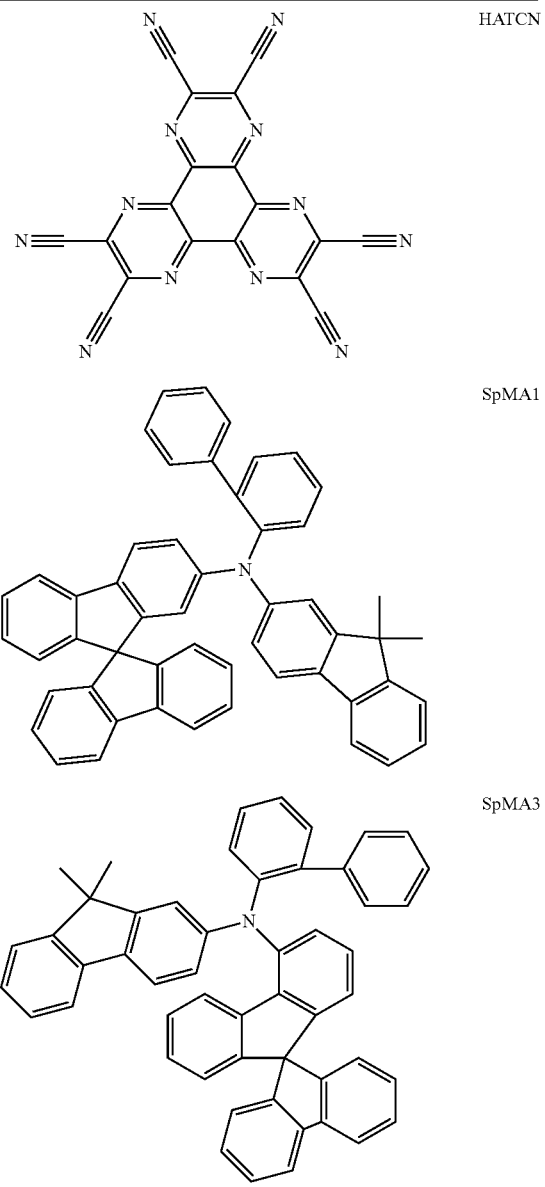

TABLE 1

Structure of the OLEDs

| Ex.1 | HL thickness | HTL thickness | EBL thickness | EML thickness | HBL thickness | ETL thickness |
|---|---|---|---|---|---|---|
| I1 | HATCN 5 nm | SpMA1 125 nm | SpMA3 10 nm | IC2:EG1:TER (50%:45%:5%) 40 nm | — | ST2:LiQ (50%:50%) 35 nm |
| I2 | HATCN 5 nm | SpMA1 125 nm | SpMA3 10 nm | IC2:EG2:TER (50%:45%:5%) 40 nm | — | ST2:LiQ (50%:50%) 35 nm |
| I3 | HATCN 5 nm | SpMA1 125 nm | SpMA3 10 nm | IC2:EG3:TER (50%:45%:5%) 40 nm | — | ST2:LiQ (50%:50%) 35 nm |
| I4 | HATCN 5 nm | SpMA1 125 nm | SpMA3 10 nm | EG4:TER (95%:5%) 40 nm | — | ST2:LiQ (50%:50%) 35 nm |
| I5 | HATCN 5 nm | SpMA1 125 nm | SpMA3 10 nm | IC1:EG5:TER (30%:65%:5%) 40 nm | — | ST2:LiQ (50%:50%) 35 nm |
| I6 | HATCN 5 nm | SpMA1 125 nm | SpMA3 10 nm | EG4:TER (95%:5%) 40 nm | EG2 5 nm | ST2:LiQ (50%:50%) 30 nm |

TABLE 2-continued
Structural formulae of the materials for the OLEDs
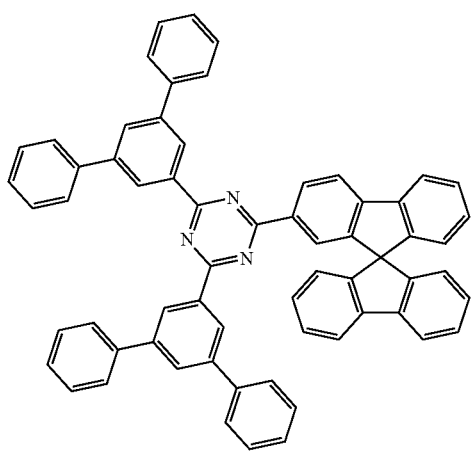 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
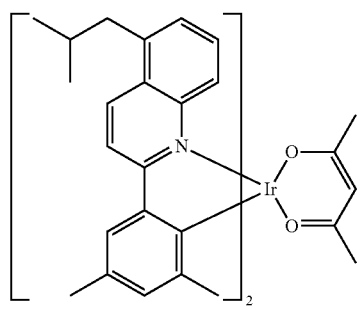
TER
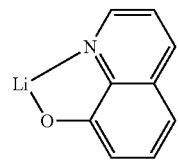
LiQ
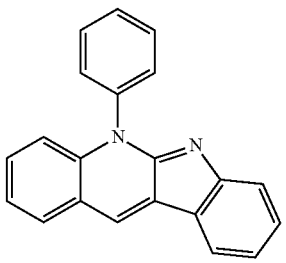 [SMILES: c1ccc(-n2c3nc4ccccc4c-3cc3ccccc32)cc1]
EG1
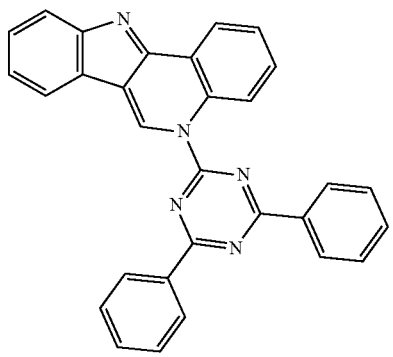 [SMILES: c1ccc(-c2nc(-c3ccccc3)nc(-n3cc4c5ccccc5nc-4c4ccccc43)n2)cc1]
EG2
TABLE 2-continued
Structural formulae of the materials for the OLEDs
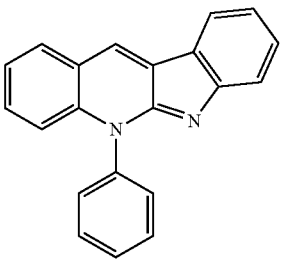 [SMILES: c1ccc(-n2c3nc4ccccc4c-3cc3ccccc32)cc1]
EG3
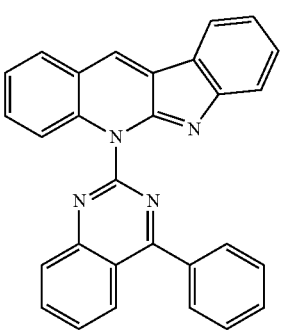 [SMILES: c1ccc(-c2nc(-n3c4nc5ccccc5c-4cc4ccccc43)nc3ccccc23)cc1]
EG4
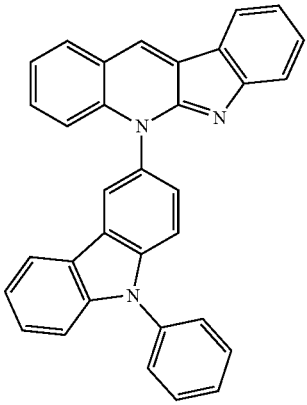 [SMILES: c1ccc(-n2c3ccccc3c3cc(-n4c5nc6ccccc6c-5cc5ccccc54)ccc32)cc1]
EG5
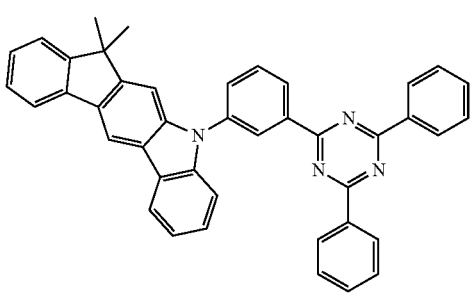 [SMILES: CC1(C)c2ccccc2-c2cc3c4ccccc4n(-c4cccc(-c5nc(-c6ccccc6)nc(-c6ccccc6)n5)c4)c3cc21]
IC1

TABLE 2-continued

Structural formulae of the materials for the OLEDs

IC2

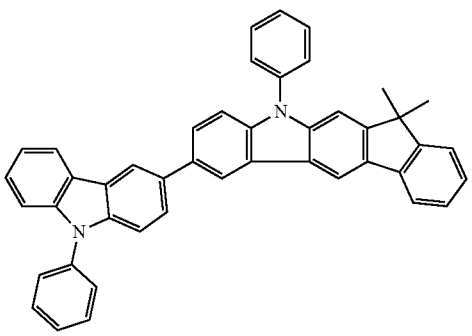 [SMILES: CC1(C)c2ccccc2-c2cc3c4cc(-c5ccc6c(c5)c5ccccc5n6-c5ccccc5)ccc4n(-c4ccccc4)c3cc21]

The invention claimed is:

1. A compound of formula (3)

Formula (3)

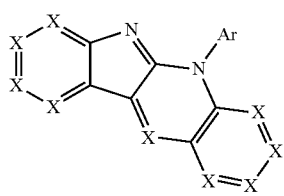

wherein X is the same or different at each instance and is CR or N;

Ar is an aromatic or heteroaromatic ring system which has 5 to 40 aromatic ring atoms and may be substituted by one or more R radicals, or is a group of the formula —Ar⁴—N(Ar²)(Ar³) where Ar², Ar³ and Ar⁴ are the same or different at each instance and are an aromatic or heteroaromatic ring system which has 5 to 24 aromatic ring atoms and may be substituted in each case by one or more R¹ radicals;

R is the same or different at each instance and is H, D, F, Cl, Br, I, N(Ar')₂, N(R¹)₂, CN, NO₂, OR¹, SR¹, COOR¹, C(=O)N(R¹)₂, Si(R¹)₃, B(OR¹)₂, C(=O)R¹, P(=O)(R¹)₂, S(=O)R¹, S(=O)₂R¹, OSO₂R¹, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R¹ radicals, where one or more nonadjacent CH₂ groups may be replaced by Si(R¹)₂, C=O, NR¹, O, S or CONR¹, or an aromatic or heteroaromatic ring system which has 5 to 60 aromatic ring atoms, preferably 5 to 40 aromatic ring atoms, and may be substituted in each case by one or more R¹ radicals; at the same time, two R radicals together may also form a ring system, or is a group of the formula —Ar⁴—N(Ar²)(Ar³) where Ar², Ar³ and Ar⁴ are the same or different at each instance and are an aromatic or heteroaromatic ring system which has 5 to 24 aromatic ring atoms and may be substituted in each case by one or more R¹ radicals;

Ar' is the same or different at each instance and is an aromatic or heteroaromatic ring system which has 5 to 40 aromatic ring atoms and may be substituted by one or more R¹ radicals or is a group of the formula —Ar⁴—N(Ar²)(Ar³) where Ar², Ar³ and Ar⁴ are the same or different at each instance and are an aromatic or heteroaromatic ring system which has 5 to 24 aromatic ring atoms and may be substituted in each case by one or more R¹ radicals;

R¹ is the same or different at each instance and is H, D, F, Cl, Br, I, N(R²)₂, CN, NO₂, OR², SR², Si(R²)₃, B(OR²)₂, C(=O)R², P(=O)(R²)₂, S(=O)R², S(=O)₂R², OSO₂R², a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R² radicals, where one or more nonadjacent CH₂ groups may be replaced by Si(R²)₂, C=O, NR², O, S or CONR², or an aromatic or heteroaromatic ring system which has 5 to 40 aromatic ring atoms and may be substituted in each case by one or more R² radicals; at the same time, two or more R¹ radicals together may form a ring system;

R² is the same or different at each instance and is H, D, F or an aliphatic, aromatic or heteroaromatic organic radical, especially a hydrocarbyl radical, having 1 to 20 carbon atoms, in which one or more hydrogen atoms may also be replaced by F;

where the following compounds are excluded from the invention:

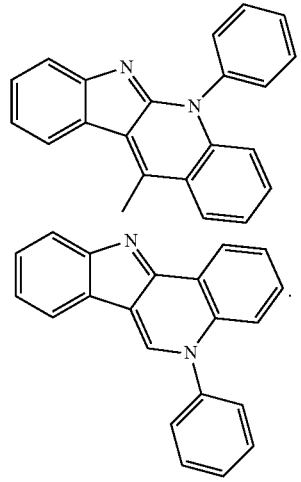

2. The compound according to claim 1, wherein all symbols X are CR or in that one symbol X is N and the remaining symbols X are CR.

3. The compound according to claim 1, selected from the compounds of the formulae (3a) to (3c)

Formula (3a)

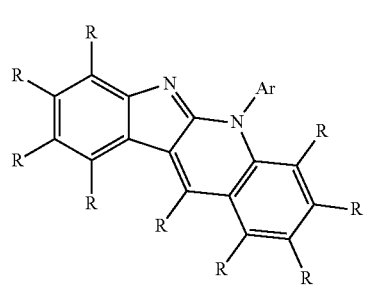

Formula (3b)

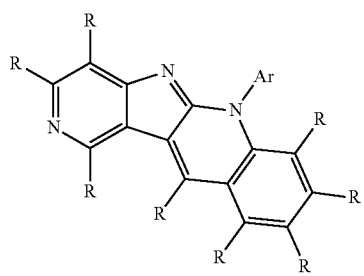

Formula (3c)

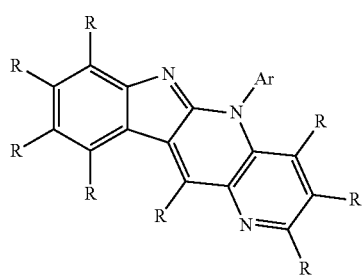

where the symbols used have the definitions given in claim 1.

4. The compound according to claim 1, characterized in that all R radicals bonded to the base skeleton are hydrogen, or in that one, two or three R radicals bonded to the base skeleton are a group other than hydrogen.

5. The compound according to claim 1, selected from the compounds of the formulae (3a-1) to (3a-12)

Formula (3a-1)

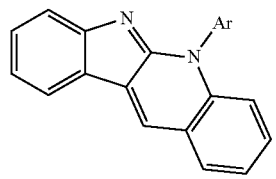

Formula (3a-2)

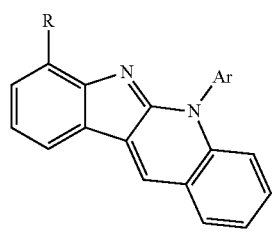

Formula (3a-3)

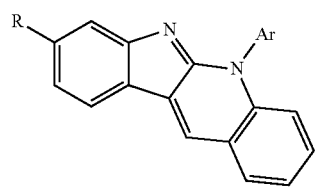

Formula (3a-4)

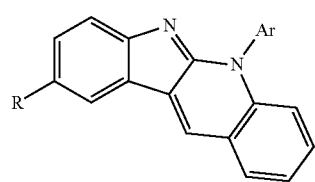

Formula (3a-5)

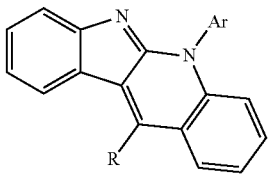

Formula (3a-6)

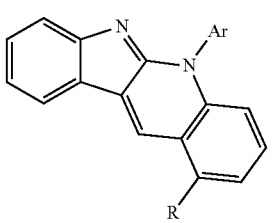

Formula (3a-7)

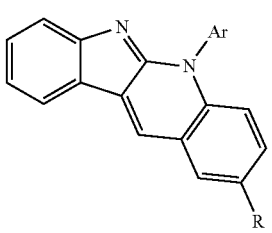

Formula (3a-8)

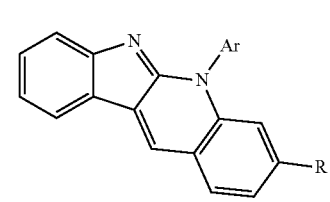

Formula (3a-9)

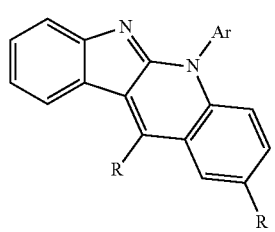

Formula (3a-10)

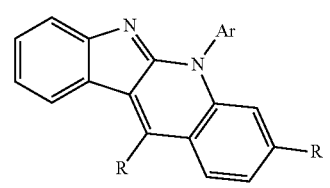

Formula (3a-11)

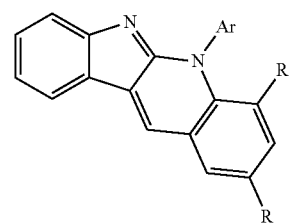

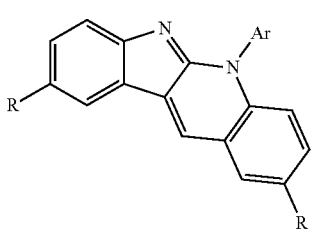

Formula (3a-12)

where the symbols used have the definitions given in claim 1 and R is not hydrogen.

6. The compound according to claim 1, wherein Ar is an aromatic or heteroaromatic ring system which has 6 to 24 aromatic ring atoms and may be substituted by one or more R radicals.

7. The compound according to claim 1, wherein Ar is selected from the group consisting of phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals.

8. The compound according to claim 1, wherein R is the same or different at each instance and is selected from the group consisting of H, D, F, $N(Ar')_2$, CN, $OR^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^1$ radicals, but is preferably unsubstituted, and where one or more nonadjacent $CH_2$ groups may be replaced by 0, or an aromatic or heteroaromatic ring system which has 6 to 30 aromatic ring atoms and may be substituted in each case by one or more $R^1$ radicals; at the same time, two R radicals together may also form a ring system.

9. The compound according to claim 1, wherein R or Ar', when they are an aromatic or heteroaromatic ring system, are the same or different at each instance and are selected from the group consisting of phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more $R^1$ radicals.

10. The compound according to claim 1, wherein at least one of the Ar, R or Ar' groups is $Ar^4$—$N(Ar^2)(Ar^3)$.

11. A formulation comprising at least one compound according to claim 1 and at least one solvent and/or at least one further organic or inorganic compound.

12. A method comprising providing the compound according to claim 1 and including the compound in an electronic device.

13. Electronic device comprising at least one compound according to claim 1.

14. Electronic device according to claim 13 which is an organic electroluminescent device, characterized in that the compound is used in an emitting layer as matrix material and/or in an electron transport layer and/or in a hole blocker layer and/or in a hole transport layer and/or in an exciton blocker layer.

* * * * *